United States Patent [19]

*Hudson et al.

[11] Patent Number: 6,159,740
[45] Date of Patent: *Dec. 12, 2000

[54] METHOD AND APPARATUS FOR SCREENING OBSCURED OR PARTIALLY OBSCURED CELLS

[75] Inventors: James Carey Hudson; Thomas Russell; Carlos M. Rodriguez, all of Miami; Wallace H. Coulter, Miami Springs, all of Fla.

[73] Assignee: Coulter Corporation, Miami, Fla.

[*] Notice: This patent is subject to a terminal disclaimer.

[21] Appl. No.: 07/525,231

[22] Filed: May 17, 1990

Related U.S. Application Data

[63] Continuation-in-part of application No. 07/339,156, Apr. 14, 1989, abandoned, which is a continuation-in-part of application No. 07/285,856, Dec. 16, 1988, abandoned, which is a continuation-in-part of application No. 07/025,345, Mar. 13, 1987, abandoned.

[51] Int. Cl.[7] .......................... G01N 33/50; G01N 33/53; G01N 33/80
[52] U.S. Cl. ...................... 436/63; 435/7.24; 435/287.2; 436/149
[58] Field of Search ................. 435/7.24, 30, 34, 435/39–40, 291, 974, 287.2; 436/63, 149

[56] References Cited

U.S. PATENT DOCUMENTS

| | | | |
|---|---|---|---|
| 3,970,518 | 7/1976 | Giaever | 435/29 |
| 4,076,419 | 2/1978 | Kleker | 436/63 |
| 4,105,598 | 8/1978 | Yen et al. | 435/7.24 |
| 4,452,773 | 6/1984 | Molday | 436/530 |
| 4,499,052 | 2/1985 | Fulwyler | 436/63 |
| 4,599,307 | 7/1986 | Saunders et al. | 436/63 |
| 4,677,061 | 6/1987 | Rose et al. | 435/34 |
| 4,727,020 | 2/1988 | Recktenwald | 435/34 |
| 4,745,071 | 5/1988 | Lapicola et al. | 436/63 |
| 4,747,685 | 5/1988 | Suzuki | 435/34 |
| 4,751,179 | 6/1988 | Ledis et al. | 435/39 |
| 4,801,549 | 1/1989 | Cremins et al. | 436/63 |
| 4,828,984 | 5/1989 | Schwartz | 435/7.24 |
| 4,851,329 | 7/1989 | Cohen et al. | 435/7.24 |
| 4,876,189 | 10/1989 | Schetters et al. | 435/7.24 |

OTHER PUBLICATIONS

Leif et al, Development of Instrumentation and Fluorochromes for Automated Multiparameter Analysis of Cells, Clin Chem v.23 No. 8 p. 1492–1498 1977.

*Primary Examiner*—Jan Ludlow
*Attorney, Agent, or Firm*—John T. Winburn; Anibal Jose Cortina; Mitchell E. Alter

[57] ABSTRACT

A method and apparatus for performing screening of obscured or partially obscured cells to enumerate one or more cell population subsets. For example, a whole blood sample or portion thereof is screened to provide the desired analysis of one or more white blood cell population subsets in the sample. A white blood cell population including the obscured subset of interest is first counted, along with a standard population. The standard population can be one of the total number of white blood cell populations, a second white blood cell population which does not obscure the shifted or non-shifted sensed characteristic of the subset of interest, an artificial population formed by microspheres which also do not obscure the shifted or non-shifted sensed characteristic of the subset of interest or a white blood cell population into which the sensed characteristic of the subset will be wholly or partially shifted. The sensed characteristic of the white blood cell population subset of interest then is shifted by binding microspheres having monoclonal antibodies specific to the white blood cell population subset of interest to the cell population. The white blood cell population, and the standard population then are again counted and compared to the original counts to obtain an enumeration of the white blood cell population subset of interest.

32 Claims, 52 Drawing Sheets

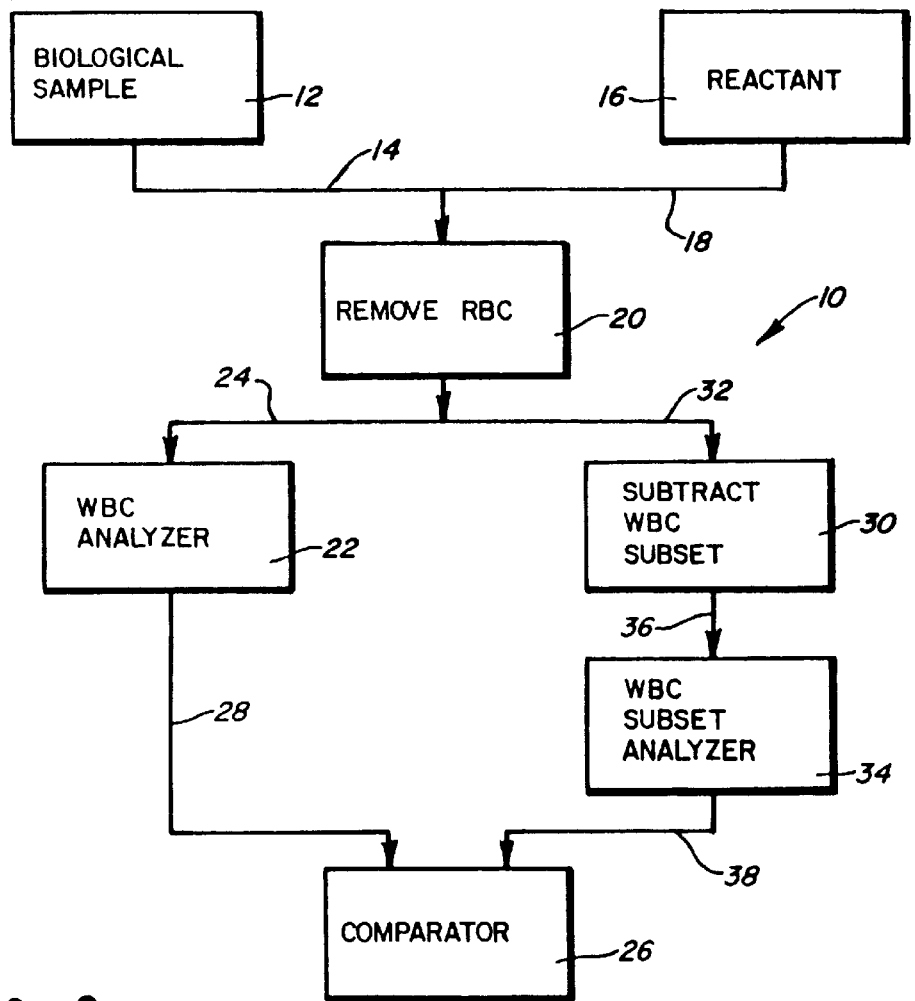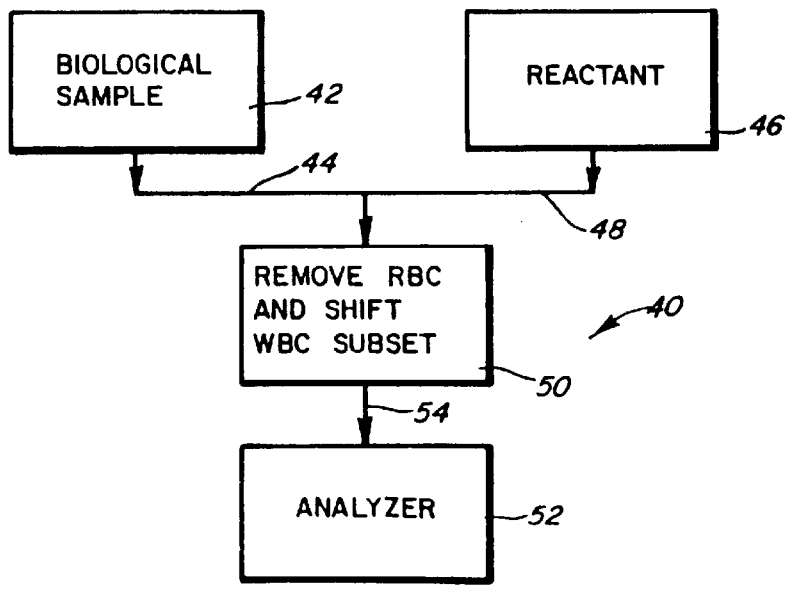

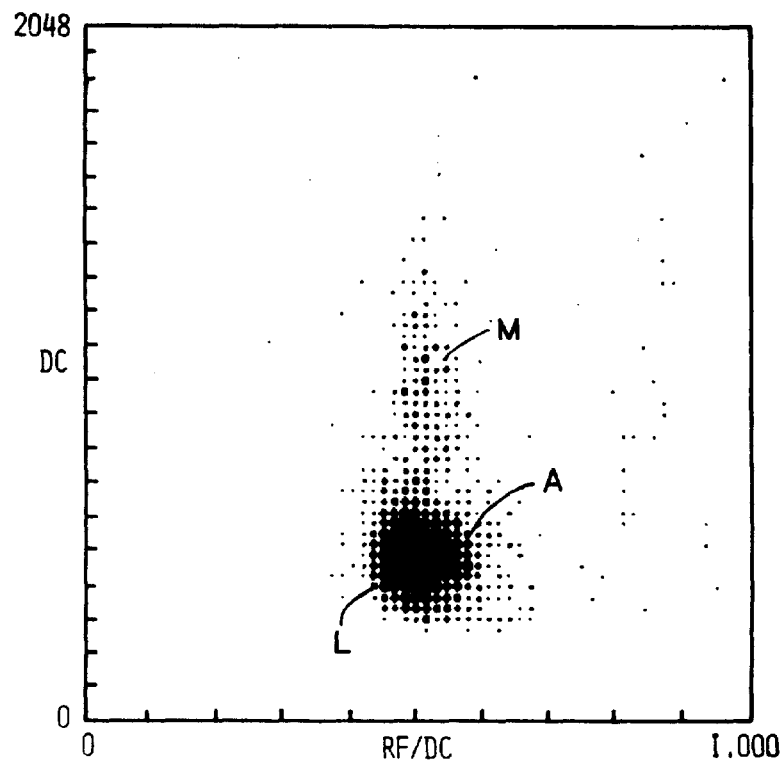
FIG. 17A
FIG. 17B
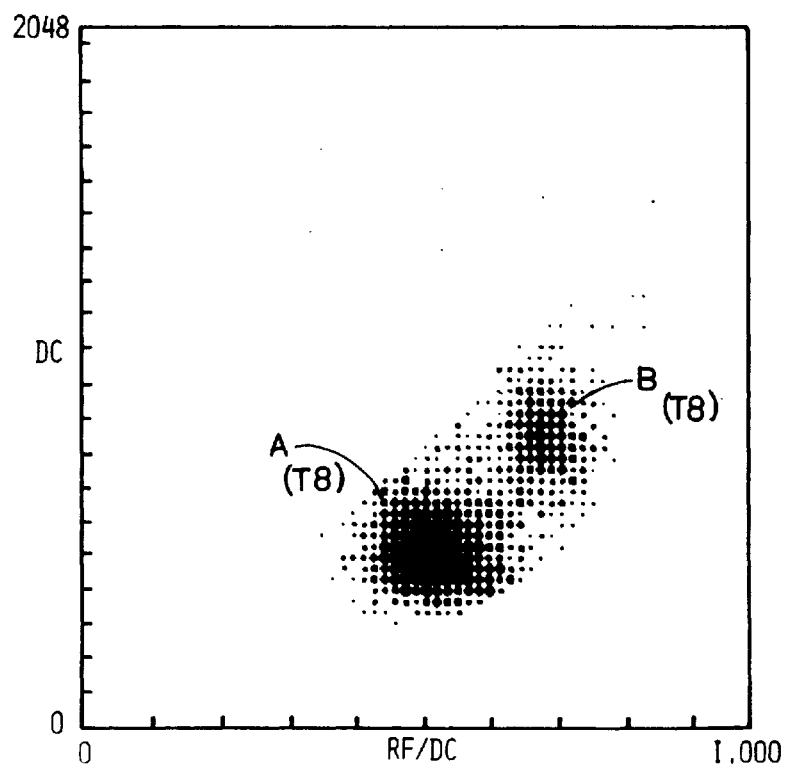

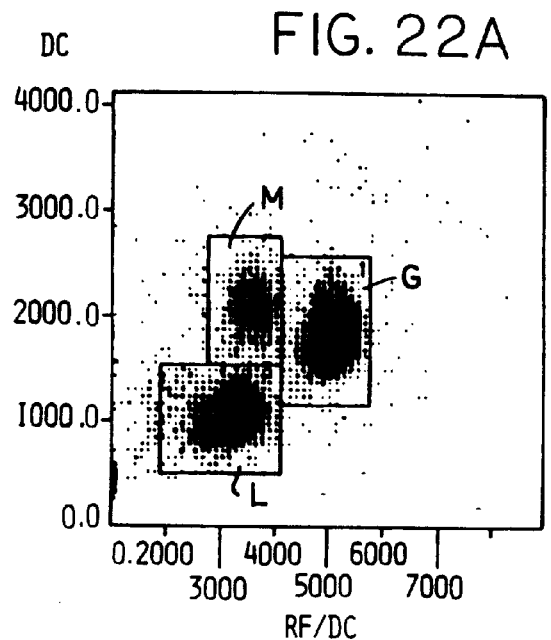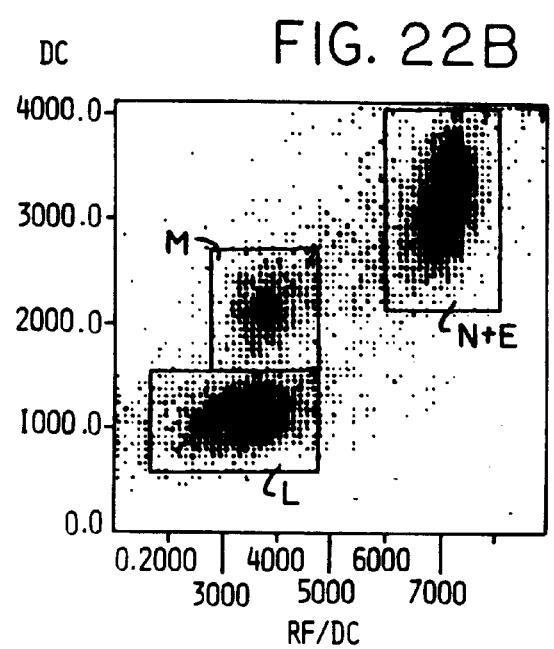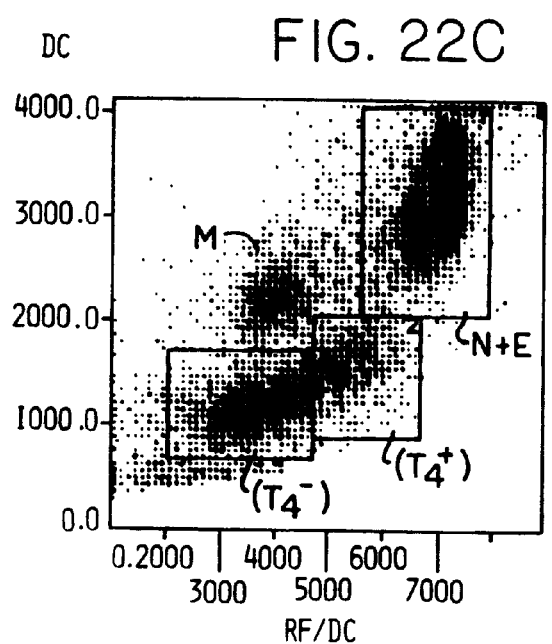

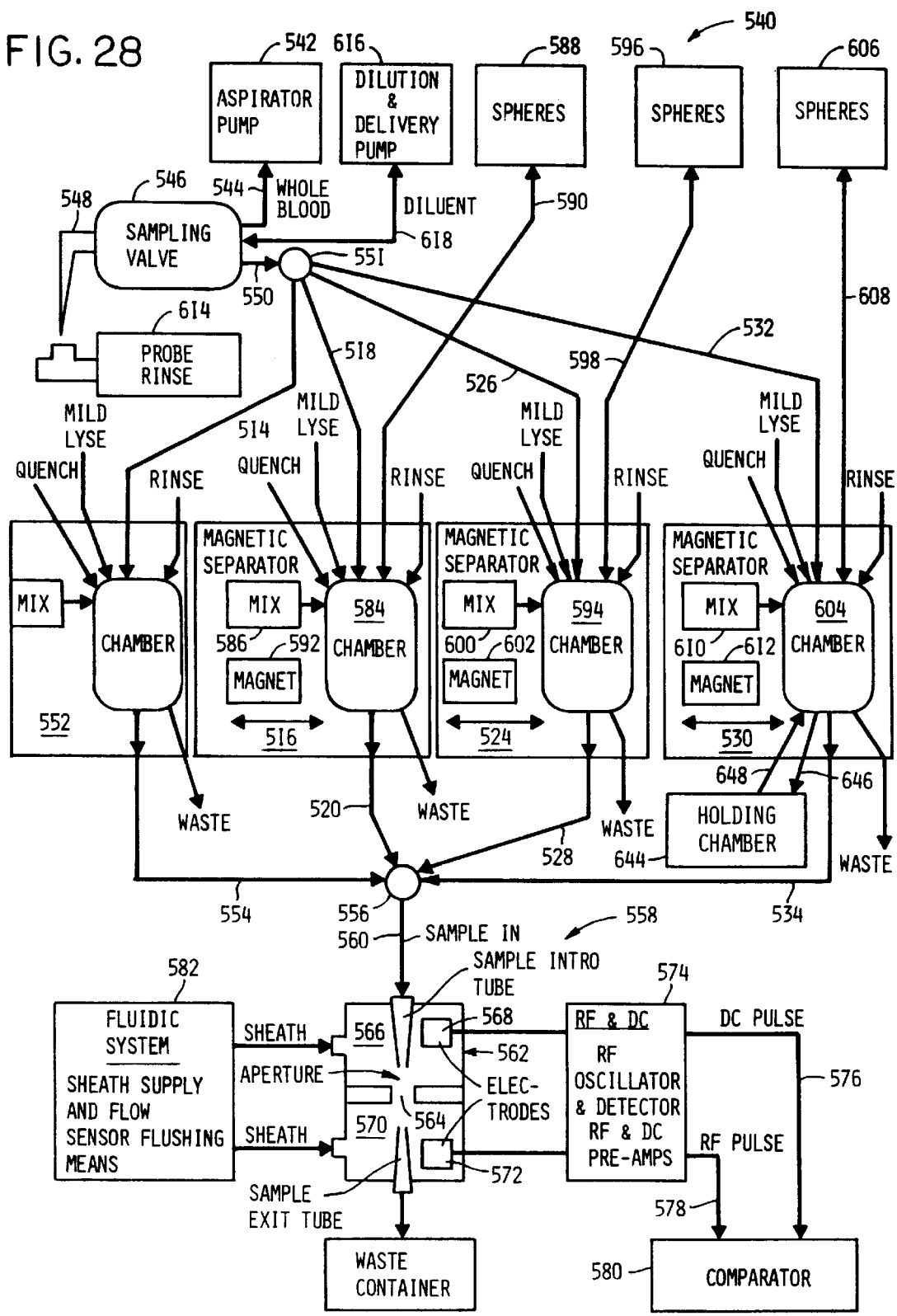

METHOD AND APPARATUS FOR SCREENING OBSCURED OR PARTIALLY OBSCURED CELLS

CROSS REFERENCE TO RELATED APPLICATIONS

This application is a continuation-in-part of applications, U.S. Ser. No. 07/339,156, filed Apr. 14, 1989, now abandoned, which is a continuation-in-part of U.S. Ser. No. 09/285,856, filed Dec. 16, 1988, now abandoned which in turn is a continuation-in-part of U.S. Ser. No. 07/025,345, filed Mar. 13, 1987, now abandoned in favor of continuation application U.S. Ser. No. 587,646, now U.S. Pat. No. 5,223,398 filed Sep. 20, 1990, the disclosures of which are incorporated herein by reference.

BACKGROUND OF THE INVENTION

This invention relates generally to a method and apparatus for screening cells which are obscured or are partially obscured by another cell population, which cells express selected characteristics for research, diagnostic or industrial purposes. More particularly, the invention is directed to an analysis of the obscured cells by utilizing microspheres having specific monoclonal antibodies bound thereto to move the sensed characteristics of the obscured cells from one cell population to another.

This invention relates generally to an automated analyzer and methods of using same for screening biological cells or formed bodies for the enumeration of populations which express selected characteristics for research, diagnostic, medical or industrial purposes. More particularly, the automated analyzers and methods embodying the invention enable multiple part classifications of cells and formed bodies, functional phenotyping of cells and formed bodies, typing of leukemic, lymphoma and solid tumor cells, among others, using a unique combination of electronic and optical technology and the specificity of selective biological molecules, such as antibodies, for such screening and selective enumeration of the cells and formed bodies.

Automation of routine complete blood cell (CBC) analysis of human peripheral blood by an automated blood cell counter was successfully achieved by the COULTER COUNTERS@ Model A of Coulter Electronics, Inc. of Hialeah, Fla. The electronic particle sensing system principle of that instrument is disclosed in U.S. Pat. No. 2,656,508 issued Oct. 20, 1953 to Wallace H. Coulter. The use of optical sensing means or lasers, which can be troublesome and expensive are avoided by particle analyzing instrumentation solely operated on this Coulter electronic sensing principle.

This Coulter sensing principle was developed and expanded into more sophisticated instrumentation such as the COULTER COUNTER@ Model S types of instruments which enabled CBC parameters, absolute cell counts, platelet count and morphology, red blood cell (RBC) morphology, interpretation of normal and abnormal blood specimens by specific computer programs.

The Coulter electronic particle sensing principle employs an aperture sensing circuit using a direct current (DC) aperture supply. Such particle sensors are simple in structure, extremely rugged and reliable as attested to by the substantially universal acceptance of the COULTER COUNTER@ automated analyzer in clinical laboratories in the United States and throughout the rest of the World. An improvement in this basic aperture sensing circuit was disclosed in U.S. Pat. No. 3,502,974 issued in 1970 to Wallace Coulter and Walter Hogg. In addition to the standard direct current aperture supply, a high frequency aperture current was applied which enabled the sensing of an additional parameter for classification purposes. The high frequency aperture current produced a signal which is the function of the blood cell's internal conductivity as well as its volume. The signal produced simultaneously by the direct current aperture circuit is a conventional DC amplitude signal which provides an indication primarily of cell volume. The radio frequency amplitude is divided by the direct current pulse amplitude employing a high speed divider circuit to obtain a quotient which is a function of cell volume and internal resistance, conveniently referred to as "opacity". This principle is further described in U.S. Pat. No. 3,502,973 also issued to Wallace Coulter and Walter Hogg, in 1970. This parameter has applicability in cell classification systems. Either a single or a pair of separate apertures could be utilized for this purpose.

Classification of different populations is accomplished by collating the data of the signal pairs as they are produced; one, a measure of particle volume and the other a measure of cell internal resistivity or opacity. A convenient form of presenting this data is by two-dimensional plots referred to as scatterplots or scattergrams. Such plots are well described in *Flow Cytometry and Sorting*, page 371; edited by Melamed Melaney, and Medelsohn, 1979, John Wiley & Sons, New York, N.Y.

FIG. 5A is one example of a data plot of a sample of normal blood. Each dot represents an individual cell. The height above the baseline represents the relative volume of the cell. The distance of the dot to the right of the vertical baseline represents the relative opacity. A plot of normal white blood cells (WBC) (with the red blood cells removed) shows three clusters of dots representing three distinct populations which are a consequence of their intrinsic differences in size and internal composition. If desired, with suitable circuitry, these populations can be enumerated to obtain the numbers of each. The cells are classified on the basis of these inherent differences.

Initial applications of the Coulter electronic particle sensing principle was to perform red blood cell counts and then, more sophisticated determinations of other red blood cell parameters. By removing red blood cells from whole peripheral blood, analysis of the white blood cell populations could be undertaken so long as the red blood cell removal did not significantly impair properties of the remaining white blood cell populations sought to be measured. Red blood cell lysing reagents were developed for this purpose which, though useful and widely applied, were not entirely satisfactory in all respects for subsequent white blood cell determinations.

Previous methods of flow analysis of leukocytes using DC volume alone or light scatter at various angles have shown three clusters of leukocytes corresponding to lymphocytes, monocytes and granulocytes which included the neutrophil, basophil and eosinophil populations. A rough but useful estimation of eosinophil concentration can be made on some samples. The fifth major population is relatively too small for this approach. The eosinophils also have been observed as a distinct cluster using special fluorescence techniques.

These fluorescent techniques were utilized in flow cytometry instruments such as the EPICS@ flow cytometer available from the Coulter Corporation. Such instruments employed the principle of cells moving in a columnar stream bounded by a sheath flow such that cells lined up in single file and passed individually through a laser beam. Light scatter and/or fluorescence signals from the cells were then utilized in classifying cell populations. Staining cells with absorptive or fluorescent dyes made additional cell population classifications possible. The development of instrumentation and fluorochromes for automated multiparameter analysis is further described by R. C. Leif, et al. in Clinical Chemistry, Vol. 23, pp. 1492–98 (1977). These developments expanded the number of simultaneous population classifications of leukocytes to four, namely lymphocytes, monocytes, eosinophils and "granulocytes" (neutrophils and basophils).

A more recent analytical hematology instrument has utilized light scattering techniques together with peroxidase enzyme staining (absorptive dye) of cells to produce a five part leukocyte differential. Moreover, dyes in combination with specific reacting biological molecules, such as monoclonal antibodies, have increased the number of leukocyte classifications possible to include functional subdivisions.

An improved single automated instrument and methods of using the same is disclosed in a first parent application, U.S. Ser. No. 025,345, filed Mar. 13, 1987, now abandoned in favor of continuation application U.S. Ser. No. 587,646, now U.S. Pat. No. 5,223,398 filed Sep. 20, 1990, entitled *AUTOMATED ANALYZER AND METHOD FOR SCREENING CELLS OR FORMED BODIES FOR ENUMERATION OF POPULATIONS EXPRESSING SELECTED CHARACTERISTICS*. This parent application combines the application of electronic sensing aperture principles, the specificity of selected biological molecules for identifying and/or enumerating defined populations of cells or formed bodies and microscopic particle technology. The automated analyzer can be used together with a special lysing reagent and/or antibodies coupled to microscopic microspheres or supports of varying composition.

A second parent application, U.S. Ser. No. 285,856, filed Dec. 16, 1988, entitled *METHOD AND APPARATUS FOR SCREENING CELLS OR FORMED BODIES WITH POPULATIONS EXPRESSING SELECTED CHARACTERISTICS*, discloses the screening of direct subsets from whole blood samples or portions thereof.

A third parent application, U.S. Ser. No. 339,156, filed Apr. 14, 1989, entitled *METHOD AND APPARATUS FOR SCREENING CELLS OR FORMED BODIES WITH POPULATIONS EXPRESSING SELECTED CHARACTERISTICS UTILIZING AT LEAST ONE SENSING PARAMETER* discloses multipart or five part white blood cell differentials, lymphocyte subsets and overlapping determinations performed from a whole blood sample or from a sample with the red blood cells and/or populations of the white blood cells removed by elimination of populations and/or subsets thereof with one or more light or electronic parameters. Each of the parent and co-pending applications referred to herein now are commonly assigned.

Selectively attaching microscopic particles makes possible the modification of the parameter(s) responsible for the original location of at least one of the populations. The bulk addition of microscopic particles to selected target populations where this addition affects the measured volume and/or opacity results in shifting the location of the dots representing a population.

Antibodies of known specificity are employed in coating microscopic particles. This coating gives the particle the capacity to selectively attach to certain cells which express the antigen the antibody is specific for. These coated or tagged cells are a combination of particles and cell which behave like a new entity. Their parameters of opacity, volume, or both opacity and volume may be considered to represent the sum of the effects of both the cell and the particles on the signals obtained. If the characteristics of the components are different, the new entity will move to a new position in accordance with the net effect. The new location, in contrast with the former position of the cell alone, should allow a classification of such new entity or group of new entities. If the particles attached to the cells are magnetic, then, of course, according to current practice, the new entities can be captured by the use of a magnet. If mixed rapidly, unexpected results including complete capture of a population without adversely affecting the properties of the cells under study occur.

Only three distinct populations of cells can be readily identified and enumerated from a blood sample by utilizing their inherent and unique properties of DC volume and opacity parameters heretofore stated. Additional steps such as improved lysing systems, must be taken to enable the detection and enumeration of more populations. Of course, these additional populations represent subpopulations of the three basic ones referred to as lymphocytes, monocytes and granulocytes. The steps performed in accordance with the parent application demonstrate how subpopulations of these basic three populations are obtained.

Employing such simple aperture sensing techniques in combination with two or more biological particles, one can produce a unique and new position of the dot cluster representing a given population. This selective movement of populations on the dot plot or scattergram is reproducible and can be used to classify a population separate from the basic three populations.

The original and inherent combination of DC volume and opacity sensing techniques can be modified through the attachment of microscopic particles to selected individual cells. The selectivity is given the particles by the nature or specificity of the biological molecules, antibodies among others, employed as the coating on their surfaces. A population of cells alone, having no particles on their surface, may occupy a dot plot position no different from other populations or subpopulations, and, henceforth, not be distinguishable from one another. The addition of particles having a selective attraction to a specific population of cells which one seeks to identify, enumerate, and study is possible using this approach. The selective addition of a sufficient mass of selective particles to a distinct population of interest results in the shifting of that population's dot plot location as a result of the new and unique combination of mass, volume and opacity.

The separation of specific cell populations is accomplished without materially affecting the properties of remaining cell populations. For example, the removal of erythrocytes or red blood cells (RBC's) from whole blood in accordance with this invention permits the measurement of T4 and/or T8 lymphocytes not otherwise possible with heretofore available chemical RBC lysing reagents. Ratios of the number of T4 versus T8 cells have been used to indicate immune deficiencies consistent with severe viral infections including the AIDS virus among others. The presence of specific receptors on the surface of cells can be used to classify a population into subsets, whose enumeration permits the detection of the onset of disease. For example, in the predominant forms of leukemia there is a sharp rise in peripheral blood lymphocytes. If the subpopulation of lymphocytes which is rapidly proliferating bears the T11 receptor, the patient is at risk of immune abnormalities.

Further, if the subpopulation of T1 positive lymphocytes is T4 receptor bearing, then the patient is classified as that leukemia common in Japan. These cells are defined as "overlapping" since the cells include at least two receptors or antigens of interest. Overlapping can be a significant parameter in diagnosis and treatment. An example of overlapping populations in a normal whole blood sample is the CD2 and CD8 subset populations. Another example of an abnormal overlapping of populations is found in CLL (chronic lymphocytic leukemia). In the CLL disease state, the CD5 and CD20 subset populations overlap. Moreover, if the T4 receptor subpopulations expanding is 2H4 positive, then the patient will not only demonstrate a tendency of multiple infections but acute leukemia as well for the T11, T4, 2H4 positive cell is the inducer of suppression and functionally inhibits the patient's ability to make antibodies. Therein the patient is subject to multiple infections and must be treated for both leukemia and immune deficiency. K. Takatsuki, et al., GANN monograph on Cancer Research 28:13–22, 1982; C. Morimoto, et al., Coulter Japan Symposium, 1984; C. Morimoto, et al., Immunology 134 (3):1508–1515, 1985; C. Morimoto, et al., New England Journal of Medicine 316(2):67–71, 1987. The invention also applies to analyses of formed body suspensions such as bacteria and viruses among others.

The method and apparatus embodying the invention can be utilized with a variety of immunological reactions, such as immunological reactions involving reacting agents and formed bodies or cells. The invention also applies to analyses of formed body suspensions such as some bacteria and viruses among others. As utilized herein, cells are defined as animal or plant cells, including cellular bacteria, fungi, which are identifiable separately or in aggregates. Cells are the least structural aggregate of living matter capable of functioning as an independent unit. For example, cells can be human RBC and WBC populations, cancer or other abnormal cells from tissue or from blood samples. Formed bodies are defined as some bacteria and viruses. The invention can be utilized in diagnosing and monitoring patients. The invention specifically can be utilized to eliminate or shift populations to analyze populations or subpopulations which cannot otherwise easily be identified. The cells and formed bodies suitably tagged or labeled reasonably can be expected to be sensed by the method and apparatus of the invention in the same manner as the human blood cell examples.

Although the term "reactant" has been utilized in the parent application to define lysing agents and monoclonal antibodies, reactants can include various agents which detect and react with one or more specific molecules which are on the surface of a cell or formed body. Some examples are given below:

| Reactant | Specific Molecule |
| --- | --- |
| Antibody | Antigen |
| Drug | Drug Receptor |
| Hormone | Hormone Receptor |
| Growth Factor | Growth Factor Receptor |

The reactants couple or bind to the specific molecule(s) on the cells. These reactants do form part of a chemical reaction; however, the reactants are not necessarily chemically altered.

This invention provides a single versatile analyzer and methods of using same which combines a minimum of electronic and/or light particle sensing technology and the specificity of selective biological molecules to enable a major advancement in the field of automated analyzers for clinical laboratory use, and for industrial applications. The detection of multiple leukocyte subpopulations, and their relationship to one another in human peripheral blood is important in medical research and the diagnosis of human diseases. Such data are useful as a screening tool for identifying and classifying diseases, such as leukemia. Abnormal situations identified by implementation of the invention herein provides diagnostically relevant information in areas of study not limited only to detection of leukocyte populations as will be apparent from the specification and drawings hereof.

One of the most valuable features of this invention is that it employs the single rugged Coulter sensing operation. It is stable and does not require the complexity and expense of complex optical systems but can utilize light sensing if desired. The circuitry required for the addition of the RF generator and detector is economical, compact and reliable. A single aperture is all that is required, but the addition of a second or even a third aperture can enable a greater sample throughput rate economically.

SUMMARY OF THE INVENTION

The invention provides a method and apparatus for performing screening of obscured or partially obscured cells to enumerate one or more obscured cells such as white blood cell population subsets. The obscured or white blood cell population subset is enumerated by identifying selected characteristics expressed by the cells of interest.

A whole blood sample or portion thereof can be screened to provide the desired analysis of one or more obscured cells such as white blood cell population subsets in the sample. For example purposes, the white blood cell population is described in detail. A white blood cell population including the obscured subset of interest is first counted, along with a standard population. The standard population can be one of the total number of white blood cell populations, a second white blood cell population which does not obscure the shifted or non-shifted sensed characteristic of the subset of interest, an artificial population formed by microspheres which also do not obscure the shifted or non-shifted sensed characteristic of the subset of interest or a white blood cell population into which the sensed characteristic of the subset will be wholly or partially shifted. The sensed characteristic of the white blood cell population subset of interest then is shifted by binding microspheres having monoclonal antibodies specific to the white blood cell population subset to the cell population. The white blood cell population, and the standard population then again are counted and compared to the original counts to obtain an enumeration of the white blood cell population subset of interest.

BRIEF DESCRIPTION OF THE DRAWINGS

FIGS. 1–13 describe the embodiments disclosed in first parent application Ser. No. 025,345;

FIG. 1 is a schematic block diagram of one cell population analyzer embodiment of the parent application;

FIG. 2 is a schematic block diagram of a second analyzer embodiment of the parent application;

FIG. 3 is one specific analyzer embodiment of the parent application corresponding to FIGS. 1 and 2;

FIG. 4 is a schematic block diagram of another analyzer embodiment of the parent application;

FIG. 6 is a schematic block diagram of a further analyzer embodiment of the parent application;

FIG. 7 is a schematic block diagram of a still further analyzer embodiment of the parent application;

FIG. 12 is a schematic block diagram of a yet still further analyzer embodiment of the parent application;

FIG. 13 is a scattergram of one set of results utilizing a prototype analyzer system similar to that illustrated with respect to FIG. 12;

FIGS. 14–26D describe the embodiments disclosed in the second parent application Ser. No. 285,856;

FIG. 14 is a schematic block diagram of one WBC population subset analyzer embodiment of the parent application;

FIG. 15 is another schematic block diagram of a WBC population subset analyzer embodiment of the parent application;

FIG. 16 is one specific analyzer embodiment of the parent application corresponding to FIGS. 14 and 15;

FIGS. 17A and 17B are a scattergram of one set of results utilizing a prototype analyzer system similar to that illustrated with respect to FIGS. 3 and 16;

FIG. 22A is a scattergram similar to the scattergram of FIG. 18A,

FIG. 22B is a scattergram illustrating shifting of the E and N populations and

FIG. 22C is a scattergram illustrating shifting of the E, N and CD4 populations;

FIGS. 26A–D are scattergrams of the same populations illustrated on different parameter scattergrams;

FIGS. 27–46 describe the embodiments of the third parent application Ser. No. 339,156;

FIG. 27 is a schematic block diagram of one single sensing parameter multipart WBC population subset analyzer embodiment of the parent application;

FIG. 28 is one specific analyzer embodiment of the parent application corresponding to FIG. 27;

FIGS. 33–36 are scattergrams of results illustrating the use of a single light sensitive parameter;

FIG. 37 is a schematic block diagram of a WBC population subset analysis for enhancing small or obscure populations;

FIG. 44 is a schematic block diagram of a WBC subset population analyzing embodiment of the invention for determining overlapping classification of cells;

FIG. 47 is a schematic block diagram of one white blood cell population subset analyzer of the present invention;

FIGS. 49–60 are scattergrams of results utilizing the methodology of the present invention to analyze obscured or partially obscured white blood cell population subsets.

DESCRIPTION OF THE PREFERRED EMBODIMENTS

Figure 3:
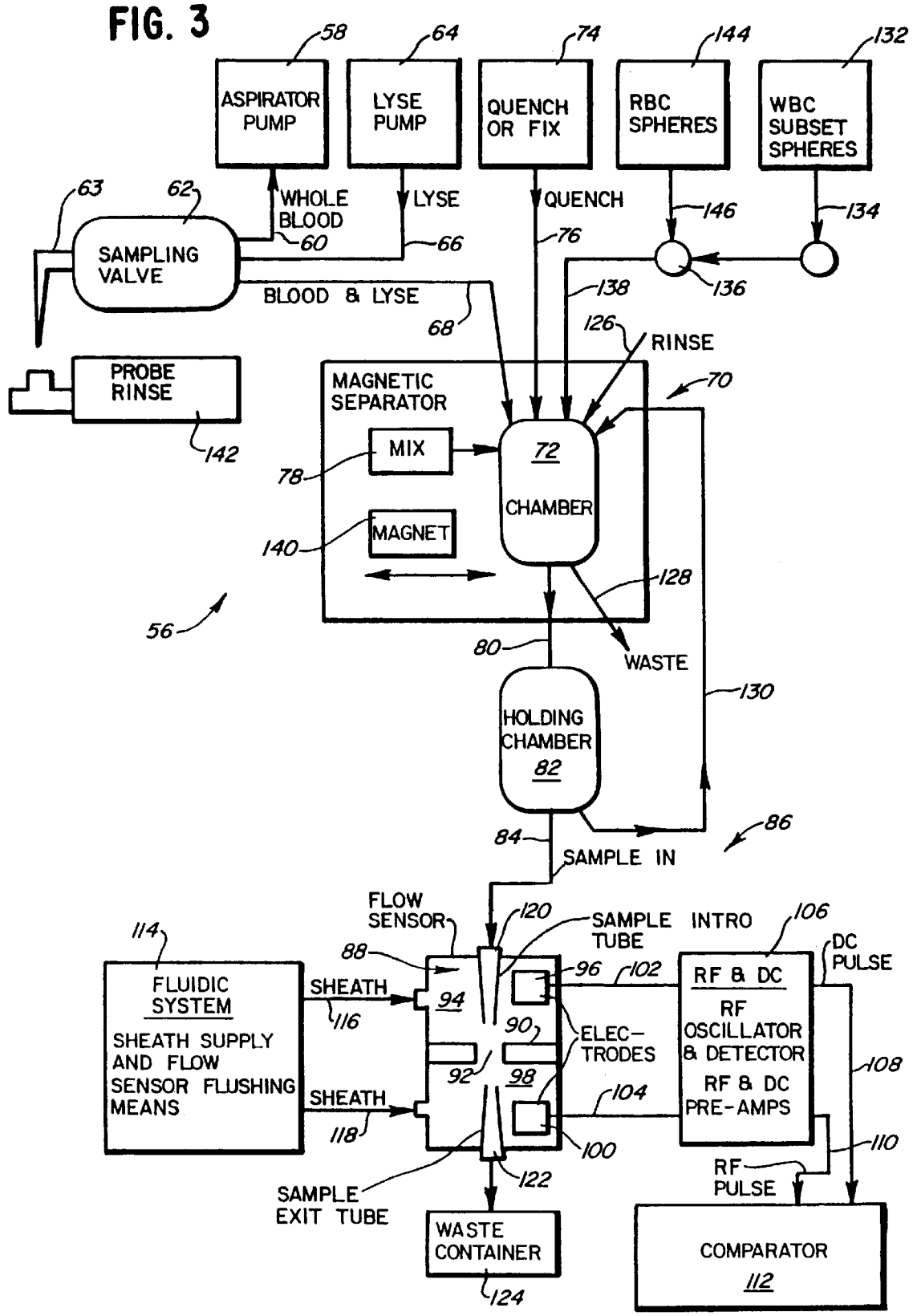

FIGS. 1–13 describe the embodiments of the first parent application, Ser. No. 025,345.

Referring to FIG. 1, a first embodiment of a cell population analyzing method and apparatus of the parent application, Ser. No. 025,345, is designated generally by the reference numeral 10. The analyzer 10 includes a biological sample 12 which contains at least a first set of viable biological cells (not illustrated), such as in or from a whole blood sample. The cells of the biological sample 12 are to be involved in a biological reaction in a quantitative and/or qualitative determination or analysis. The sample 12 can include a buffer into which the cells are added.

The sample 12 is combined via a line 14 with at least one reactant 16 via a line 18. The red blood cells (RBC) then are removed from the mixture by a functionally designated RBC removing station 20. The RBC's can be removed from the mixture by the station 20 in a number of ways. The RBC's can be lysed by a lyse in the reactant 16. One such preferential lyse and a quench which can be utilized therewith is disclosed in Ser. No. 130,911, filed Dec. 10, 1987, now abandoned in favor of continuation application U.S. Ser. No.

611,378, filed Nov. 13, 1990, now abandoned entitled *METHOD AND REAGENT SYSTEM FOR ISOLATION, IDENTIFICATION AND/OR ANALYSIS OF LEUKOCYTES FROM WHOLE BLOOD SAMPLES*, which is a CIP of Ser. No. 025,303, filed Mar. 13, 1987, now abandoned in favor of continuation application U.S. Ser. No. 317,147, filed Feb. 28, 1989, now abandoned of the same title, which are incorporated herein by reference. The reactant 16 can be or include a plurality of magnetic microspheres with an antibody specific to the RBC's bound to the microspheres (not illustrated). In this example, the particular red blood cell specific antibody utilized is disclosed in application Ser. No. 799,489, filed Nov. 19, 1985, now U.S. Pat. No. 4,752,563, entitled *MONOCLONAL ANTIBODY FOR RECOVERY OF LEUKOCYTES IN HUMAN PERIPHERAL BLOOD AND METHOD OF RECOVERY EMPLOYING SAID MONOCLONAL ANTIBODY*, which is incorporated herein by reference. The reactant 16 also can include a buffer in addition to or in place of the sample buffer. The reactant 16 further can be a combination of the preferential RBC lyse and the RBC specific microspheres.

Once the RBC's substantially are removed from the mixture, a portion of the mixture is fed into a white blood cell (WBC) analyzer 22 via a line 24. The WBC analyzer 22 at least counts the number of WBC's in the mixture. The WBC analyzer 22 also can measure one or more volume or opacity parameters of the WBC's. The results from the analyzer 22 are fed to a comparator 26 via a line 28.

A second portion of the RBC deleted mixture is fed to a WBC subset subtracting station 30 via a line 32. The WBC's can be subtracted from the mixture in a number of ways. Microspheres with a monoclonal antibody specific to one of the WBC subsets bound thereto can be added to the mixture. Non-magnetic microspheres can be bound to the WBC's to change or shift the resultant opacity or volume parameters of the cells. Magnetic microspheres also can be bound to the WBC's which then can be removed from the mixture by a magnetic field.

The mixture with the WBC subset population removed or with one or more parameters changed then is fed to a WBC subset analyzer 34 via a line 36. The analyzer 34 can be identical to the analyzer 22. The results of the analyzer 34 are then fed to the comparator 26 via a line 38. The comparator 26 then can compare the WBC results from the analyzer 22 with the modified results from the analyzer 34 to determine at least one characteristic of the selected white blood cell population, such as the number of cells in a particular range.

Referring to FIG. 2, a second embodiment of a cell population analyzing method and apparatus embodying the parent application is designated generally by the reference numeral 40. The analyzer 40 includes a biological sample 42 which again contains at least a first set of viable biological cells (not illustrated), such as in or from a whole blood sample. The cells of the biological sample 42 are to be involved in a biological reaction in a quantitative and/or qualitative determination or analysis. The sample 42 again can include a buffer into which the cells are added.

The sample 42 is combined via a line 44 with at least one reactant 46 via a line 48. In the analyzer 40, the RBC's are removed from the mixture and simultaneously at least one characteristic of at least one WBC subset is changed or shifted by a functionally designated RBC removing and WBC shifting station 50. As stated above, the RBC's can be removed from the mixture by the station in a number of ways, previously enumerated with respect to the station 20. Simultaneously, in the same mixture portion, the WBC's are bound to, generally non-magnetic, microspheres to change or shift the resultant opacity and/or volume parameters of the cells.

The mixture with the RBC's removed and the WBC subset population shifted then is fed to an analyzer 52 via a line 54. The analyzer 52 can be substantially identical to the analyzer 22. The analyzer 40 thus provides a fast, direct analysis of at least one characteristic of a selected WBC population or WBC subset.

One specific embodiment of an analyzer instrument embodying the parent application and which can accomplish the analyzing methods of the first and second analyzers 10 and 40, is designated generally by the reference numeral 56 in FIG. 3.

In the instrument 56, only one specific enumeration is illustrated, which can be varied in almost endless detail in accordance with the principles of the parent application. Further, the instrument 56 is shown in generally functional detail and the specific embodiments can be structurally implemented in many known ways.

The instrument 56 includes an aspirator pumping mechanism 58 which is utilized to draw the biological sample of interest, for example the sample 12 or 42 into the instrument 56. The aspirator 58 is coupled via a line 60 to a sampling valve 62, which can be coupled to a sample probe 63. A lyse pump 64 can include the lyse, such as part of the reactant 18 or 46 and is also coupled to the valve 62 via a line 66. The valve 62 and the pump 58 can aspirate the biological sample 12 or 42 along with the lyse via the pump 64 when appropriate.

The reactant mixture or the biological sample itself, then is fed via a discharge line 68 into a mixing apparatus 70. The mixer 70 includes a mixing chamber 72 into which the sample or reactant is fed. At this point the operation of the analyzer 10 and 40 differ and hence will be described separately.

In the case of the analyzer 10, if the RBC's have been lysed by the lyse from the pump 64, then when the reaction is completed a quench or fix is supplied from a station 74 via a line 76. The reaction can be assisted by mixing the lyse and the sample in the chamber 72 as illustrated functionally at 78.

Specific details of an appropriate mixing apparatus 70, which can be utilized herein are disclosed in Ser. No. 025,337, filed Mar. 13, 1987, now abandoned in favor of continuation application U.S. Ser. No. 517,309, filed May 1, 1990, now U.S. Pat. No. 5,238,812 entitled *METHOD AND APPARATUS FOR RAPID MIXING OF SMALL VOLUMES FOR ENHANCING BIOLOGICAL REACTIONS*, which is incorporated herein by reference. By utilizing the mixer 70 the reactions are greatly enhanced in speed without significantly damaging the properties of interest of the cells, such as, can occur by raising the reaction temperature. Further, the reactions generally are completed in significantly less than a minute, generally on the order of fifteen seconds or less. This allows a rapid analysis of the automatic high volume analyzer instrument 56.

The quenched reactant with the RBC's removed by the lyse (as from the station 20) then is fed via a line 80 to a holding chamber 82, which in this case will hold a second portion of the mixture. A first portion of the mixture will be fed from the chamber 82 via a line 84 to a WBC analyzer 86 (i.e., analyzer 22). The analyzer 86 can be of many physical types in accordance with the counting and sizing techniques described by Wallace H. Coulter in U.S. Pat. No. 2,656,508 and embodied in the numerous commercial blood cell counters of the assignee, Coulter Electronics, Inc.

The analyzer 86, in general, includes a flow sensor or sensing chamber 88. The chamber 88 includes a transducer 90 which has an aperture 92 therethrough. The chamber 88 includes a first portion 94 which has a first electrode 96 in contact with the fluid therein.

The chamber portion 94 and the electrode 96 communicate through the aperture 92 with a second chamber portion 98 having a second electrode 100 therein. The electrodes 96 and 100 are coupled via reactive leads 102 and 104 to an RF/DC source and sensing circuit 106. The circuit 106 couples both a DC, or low frequency current or signal, and a high frequency signal between the electrodes 96 and 100.

The low frequency signal is utilized to sense the amplitude of a signal pulse caused by a cell passing through the aperture 92. The high frequency signal is utilized to obtain the electrical opacity of the same cell passing through the aperture 92.

The measuring of the electrical opacity of cells was described by Wallace H. Coulter and Walter R. Hogg in U.S. Pat. No. 3,502,974 and several patents and publications of the assignee, Coulter Electronics, Inc., since that patent. One specific circuit which can be utilized herein is disclosed in Case 168,008, entitled *PARTICLE ANALYZER FOR MEASURING THE RESISTANCE AND REACTANCE OF A PARTICLE*, filed Oct. 21, 1986, now U.S. Ser. No. 921,654, now U.S. Pat. No. 4,791,355, which is incorporated herein by reference.

The signals generated by the circuit 106 from the sensed cells are coupled via a DC signal lead 108 and an RF signal lead 110 to a comparator 112 (like the comparator 26). The comparator 112 can hold the signal generated from the first portion, i.e., those without the WBC subset subtracted, for a comparison with the results from the second portion to be described.

The analyzer 86 can include a sheath flow to focus the cells in the sensor 88, in the well known manner. The sheath flow can be provided by a fluidic system 114, coupled to the sensor 88 by a pair of lines 116 and 118 in a known manner. The sample reaction mixture can be fed into the sensor 88 via an introduction tube 120 and can be fed from the sensor 88 via an exit tube 122 into a waste container 124.

While the first portion of the mixture was being analyzed in the analyzer 86, the second portion is held in the chamber 82, while the mixer 72 is cleaned or flushed via a rinse line 126 and exhausted through a waste line 128. Once the chamber 72 is cleaned, the second portion is fed back into the chamber 72 via a line 130. Like the station 30, the WBC subset now is subtracted by adding the WBC microspheres from a station 132 via a line 134, a valve 136 and a chamber line 138.

The WBC microspheres are mixed with the second portion by the mixing mechanism 78. If the WBC microspheres are non-magnetic, the reaction mixture with the bound WBC microspheres is fed via the line 80, the chamber 82 and the line 84 into the analyzer 86 (i.e., the analyzer 34), wherein the second portion is analyzed like the first portion and the results then are compared in the comparator 112 (i.e., the comparator 26). At least one of the WBC subset cell parameters is changed in the second portion, such as the cell opacity by the WBC subset bound microspheres to provide the changed results which then can be analyzed.

If the WBC microspheres are magnetic, then the WBC subset bound thereto are removed by a magnetic field during and/or after the mixing process by a magnetic field or magnet 140. The field can be provided by electromagnetic means or by the magnet 140 being physically moved with respect to the chamber 72 to capture the magnetically bound WBC subset. The second portion without the bound WBC subset then is fed via the line 80, the chamber 82 and line 84 to the analyzer 86 in the manner previously described to obtain the analysis (like the analyzer 34).

The instrument 56 then is prepared to take the next sample for the next analysis. The probe 63 can be cleaned by a probe rinse mechanism 142 and the lines and chamber 72 and 82 can be flushed in a conventional manner. Each analysis of the succeeding sample mixture is obtained in a rapid and automatic fashion. The period between the analysis of succeeding sample mixtures can be on the order of minutes or less.

In operating the analyzer instrument 56, like the analyzer 40, the reaction mixture with the RBC lyse/reactant 46 and the sample 42 is mixed in the chamber 72 along with non-magnetic WBC microspheres from the station 132, which bind to one of the WBC subsets. The quench 74 is added to the reactive mixture which then is fed via the line 80, the chamber 82 and the line 84 to the WBC analyzer 86 for analysis (i.e., like the analyzer 52).

Alternatively to the utilization of the lyse, in either of the analyzers 10 and 40, the sample 12 or 42 can be fed to the mixer 70 via the valve 62 without any lyse. In this case, the RBC's can be removed magnetically by utilizing the microspheres with the RBC specific antibody bound thereto from an RBC microsphere station 144 and fed to the valve 136 via a line 146 and hence to the chamber 70 via the line 138. Where no lyse is utilized, the bound RBC's are magnetically removed by the magnet 140 after mixing in a manner substantially identical to the magnetically bound WBC's described above.

Further, in a second case to promote the speed of the reaction, a reaction mixture of the sample with both the RBC lyse and with the RBC magnetic beads can be utilized. The reaction mixture is mixed, the lyse is quenched and the bound RBC's are magnetically removed and then the WBC's are analyzed as previously described.

Figure 4:
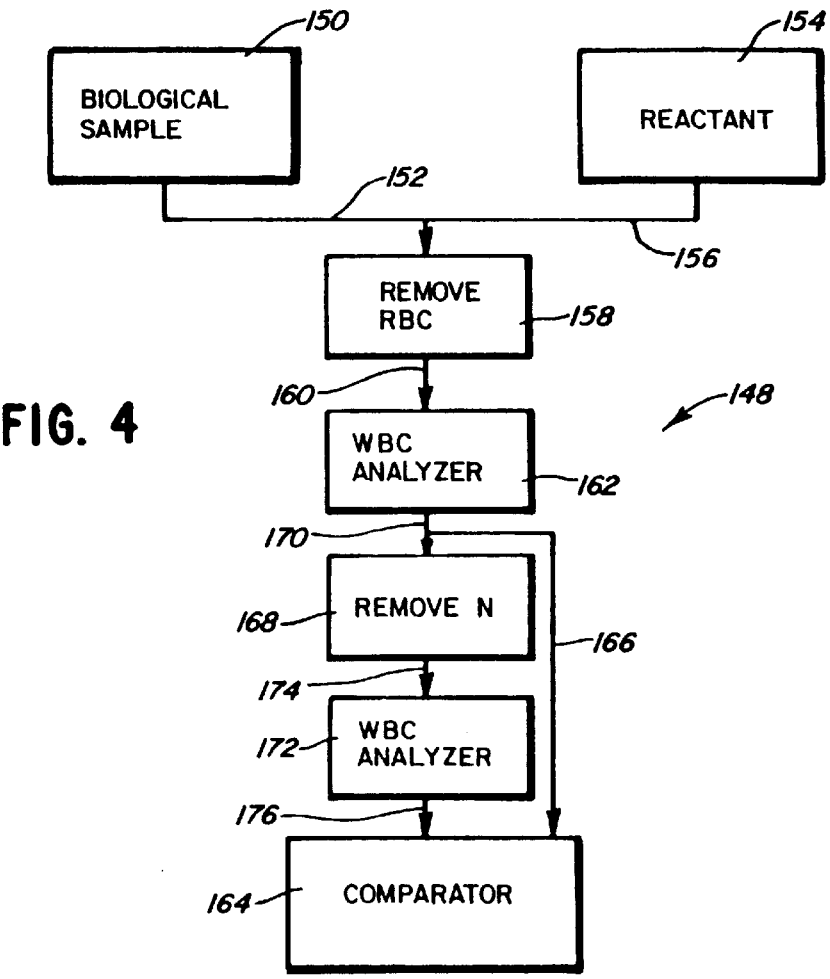

Referring now to FIG. 4, another embodiment of a cell population analyzing method and apparatus embodying the parent application is designated generally by the reference numeral 148. The analyzer 148 includes a biological sample 150 which again contains at least a first set of viable biological cells, such as in or from a whole blood sample. The sample 150 again can include a buffer into which the cells are added.

The sample 150 is combined via a line 152 with at least one reactant 154 via a line 156. The RBC's then are removed as above described by a functionally designated RBC removing station 158. The reaction mixture with the RBC's removed is fed via a line 160 into a WBC analyzer 162. The results from the analyzer 162 are fed to a comparator 164 via a line 166, providing a three-part WBC differential with results for monocytes (M), lymphocytes (L) and granulocytes (G).

The mixture then is fed to a neutrophil (N) functionally designated removal station 168 via a line 170. The N's can be removed from the mixture by shifting or changing one parameter, such as opacity, or by magnetic removal, both as described above. In this example, the particular N specific antibody utilized is disclosed is Case 168,306, *MONOCLONAL ANTIBODY SPECIFIC TO NEUTROPHILS*, filed Dec. 8, 1986, now U.S. Ser. No. 938,864, now abandoned in favor of continuation-in-part application U.S. Ser. No. 070,202, filed Jul. 6, 1987, now U.S. Pat. No. 4,931,395.

The mixture with the N's removed or shifted then is fed to another WBC analyzer 172 via a line 174. The results of the analyzer 172 are fed to the comparator 164 via a line 176. The results of the analyzer 172 are utilized to obtain a four-part WBC differential with results again for M's and L's, but now in addition since the N's are shifted or removed results for eosinophils (E) and basophils (B) are obtained. The two analytical results from the analyzers 162 and 172 then can be compared by the comparator 164 to form a five-part WBC differential. Specifically, subtracting the number of B's and E's from the number of G's results in the number of the removed N's.

Figure 5A:
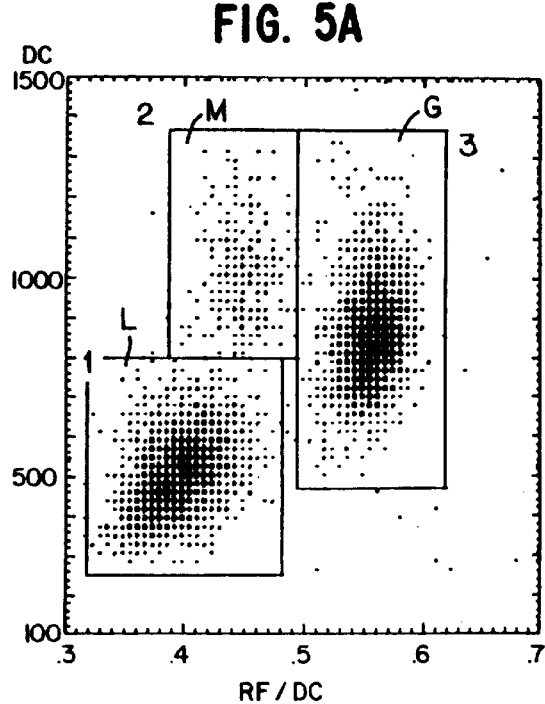
FIGS. 5A and 5B are a scattergram of one set of results utilizing a prototype analyzer system similar to that illustrated with respect to FIGS. 2 and 3.
Figure 5B:
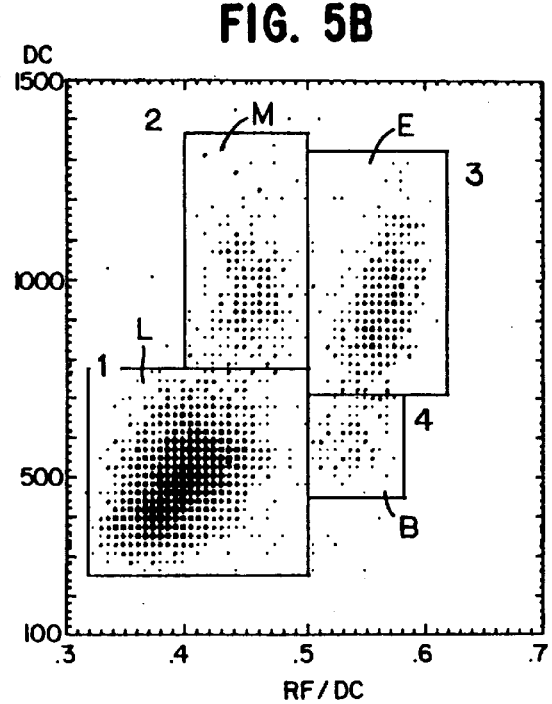

Referring now to FIGS. 5A and 5B, two sets of scattergram results are illustrated obtained from a whole blood sample utilizing a prototype analyzing method similar to the analyzer 148. The biological sample 150 was a 20 microliter sample of whole blood which was combined with 40 microliters of the magnetic microspheres with the RBC specific antibody bound thereto combined with 140 microliters of buffer solution to form the reactant 154. The reaction mixture was mixed for 15 seconds and placed in a magnetic field for 10 seconds in the station 158. The mixture with the RBC's removed was analyzed by the analyzer 162 as illustrated in the scattergram of FIG. 5A resulting in counts of L's of 45.6 (1), M's of 5.6 (2) and G's of 48.7 (3).

The mixture then is combined in the station 168 with 10 microliters of magnetic microspheres with the N specific antibody bound thereto. The mixture is mixed 30 seconds and then placed in a magnetic field for 10 seconds. The mixture with the N's then removed was fed to the analyzer 176 which resulted in the scattergram of FIG. 5B resulting in counts of L's of 81.0 (1), M's of 0.6 (2), E's of 11.0 (3) and B's of 1.8 (4). The comparator 164 then provides the five-part WBC differential of counts of 45.6 L's, 5.6 M's, 41.6 N's, 6.0 E's and 1.2 B's. This corresponds to a standard microscopic five-part WBC differential utilizing Wright stain on the sample on a slide resulting in counts of 44.0 L's, 3.4 M's, 45.0 N's, 6.1 E's and 0.4 B's.

Figure 6:
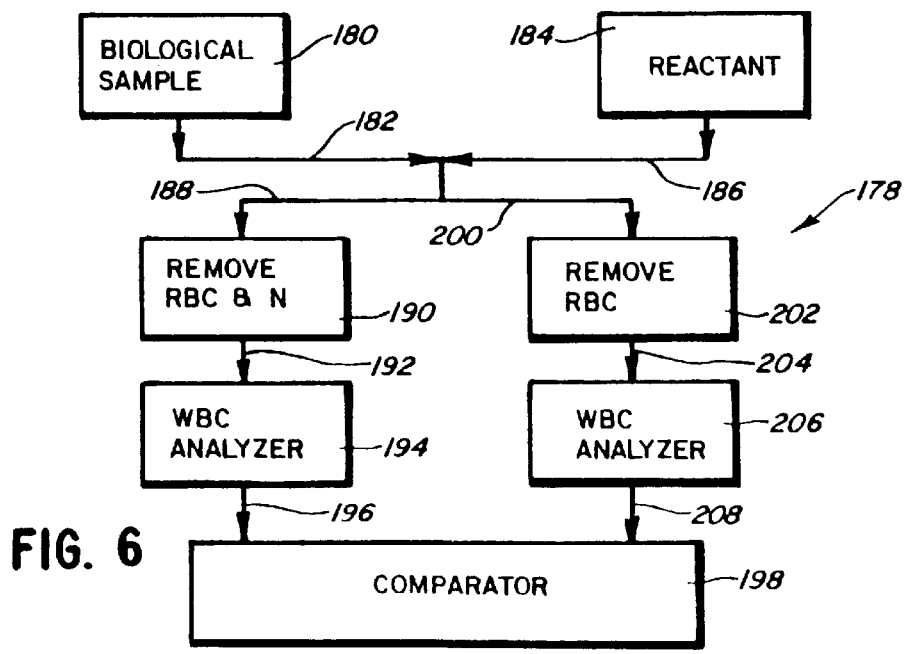

FIG. 6 illustrates a further embodiment of a cell population analyzing method and apparatus embodying the parent application, designated generally by the reference numeral 178. The analyzer 178 includes a biological sample 180 which again contains at least a first set of viable biological cells and also can include a buffer.

The sample 180 is combined via a line 182 with a reactant 184 via a line 186. Functionally illustrated, a first portion of the mixture is fed via a line 188 to a functionally designated RBC and N removing station 190. The RBC's and N's are removed or shifted as described before and the first portion is fed via a line 192 to a WBC analyzer 194.

This provides a result from the analyzer 194 which is fed via a line 196 to a comparator 198. The results includes the above-referenced four-part differential including M's, L's, E's and B's.

At the same time, a second portion of the mixture of the sample 180 and the reactant 184 is fed via a line 200 to a functionally designated RBC removal station 202. The mixture with the RBC's removed is fed via a line 204 to another WBC analyzer 206. The results of the analyzer 206 are fed to the comparator 198 via a line 208. The results of the analyzer 206 directly include the above-referenced three-part WBC differential including M's, L's and G's. the results of the analyzers 194 and 206 then are compared by the comparator 198 to provide the five-part WBC differential.

Figure 7:
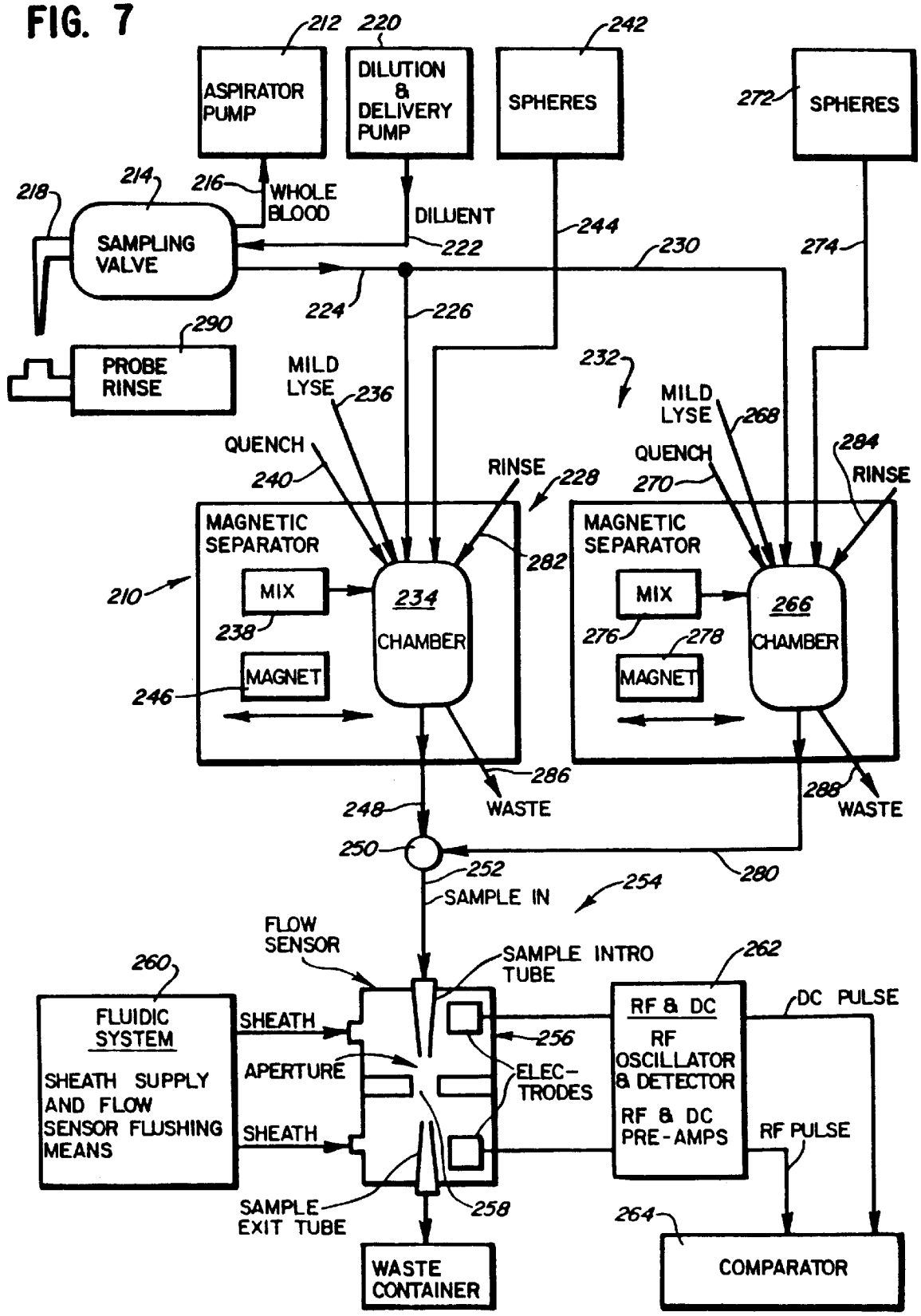

A specific analyzing instrument embodiment incorporating the method and apparatus of the analyzer 178 is designated generally by the reference numeral 210 in FIG. 7. Again, only one specific hardware enumeration has been illustrated, but like the analyzing instrument 56, the analyzing instrument 210 can be implemented in numerous configurations.

The instrument 210 includes an aspirator purging mechanism 212 which is coupled to a sampling valve 214 via a line 216. The valve 214 can include a sample probe 218 to aspirate the biological sample of interest, such as the sample 180. A diluent delivery pump 220 is coupled to the valve 214 via a line 222 to provide a diluent for the sample, such as a whole blood sample, when desired. A first portion of the mixture then is coupled via a line 224 and a line 226 to a first mixing apparatus 228. At the same time, a second portion of the mixture is fed via the line 224 and a line 230 to a second mixing apparatus 232.

The mixer 228 (comparable to the station 190) is substantially identical to the mixer 232 (comparable to the station 202) and will be described first. The mixer 228 includes a mixing chamber 234 into which the first mixture portion is fed. The mixer 228 includes all of the various options above described and can include a lyse input line 236 for the RBC lyse if desired.

If the lyse is utilized, after mixing as illustrated functionally at 238, then the quench is added via a quench line 240. At the same time, the N's are being removed by the addition of the appropriate magnetic or non-magnetic microspheres with the N specific antibody bound thereto from a source of microspheres 242 fed to the chamber 234 via a line 244. If magnetic microspheres are utilized for the N's or the RBC's, then a magnet 246 or magnetic field is utilized to remove the magnetically bound cells.

The mixed and quenched (where necessary) mixture then is fed via a line 248 through a valve 250 and a line 252 to a WBC analyzer 254 (i.e., analyzer 194). The analyzer 254 is the same as the analyzer 86 and will not be described again in such detail. Again, the analyzer 254 includes a sensing chamber 256 with an aperture 258 therein through which the mixture and cells pass. A sheath flow fluidic system 260 can be coupled to the chamber 256. The signals generated by the cells are detected by an RF/DC source and sensing circuit 262 whose outputs are fed to a comparator 264, as previously described.

Concurrently, the second mixture portion is fed into a mixing chamber 266. In the second portion, only the RBC's are removed (i.e., like the station 202) and the RBC's can be removed by the RBC lyse fed into the chamber 266 via a line 268. The lyse is mixed with the sample and then a quench is added via a quench line 270. Alternatively the RBC's can be removed by magnetic microspheres having the RBC specific antibody bound thereto from a microsphere source 272 fed into the chamber 266 via a line 274. The microspheres are mixed, functionally at 276, and then the magnetically bound RBC microspheres are removed by a magnet 278.

The RBC removed mixture then is fed via a line 280 to the valve 250 and via the line 252 to the analyzer 254 to obtain the above-mentioned results. The mixers 228 and 232 include appropriate respective rinse lines 282 and 284 and waste lines 286 and 288 and a probe rinse 290 to cleanse the instrument 210 prior to aspirating the next sample or sample for analyzing.

Figure 8A:
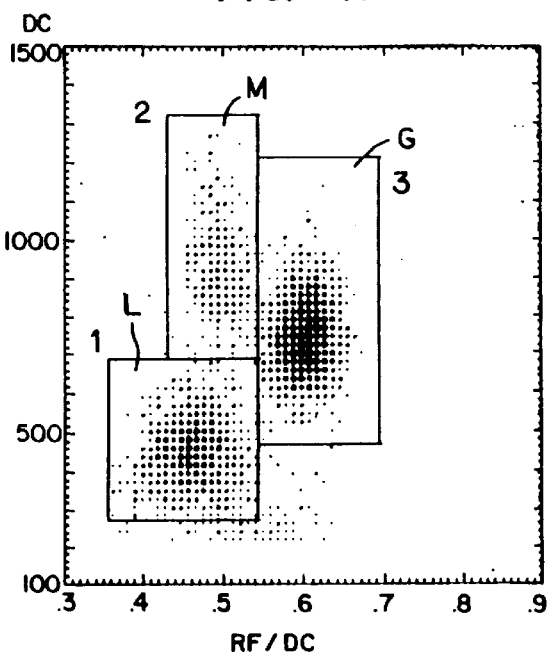
FIGS. 8A and 8B, 9A and 9B, 10A and 10B and, 11A and 11B are a scattergram of one set of results utilizing a prototype analyzer system similar to that illustrated with respect to FIGS. 6 and 7.
Figure 8B:
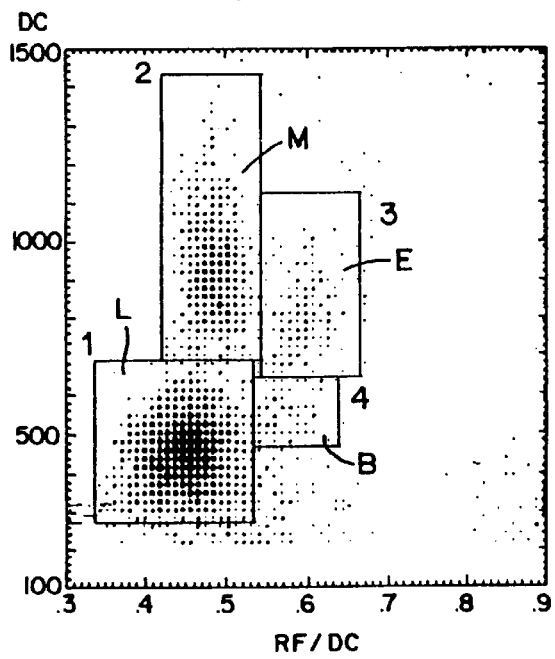

FIGS. 8A and 8B illustrate scattergram results obtained from a whole blood sample utilizing an analyzing method similar to the analyzer 178. In this example, 20 microliters of whole blood form the sample 180, while 40 microliters of magnetic microspheres with the RBC specific antibody bound thereto combined with 140 microliters of buffer solution form the reactant 184. A portion of the mixture is mixed for 20 seconds in the station 202 and then placed in a magnetic field for 10 seconds. The RBC removed mixture then is analyzed in the analyzer 206 resulting in the scattergram of FIG. 8A which provides a count of L's 29.4 (1), M's 8.1 (2) and G's 62.4 (3).

At the same time, another portion of the same mixture is combined with 10 microliters of magnetic microspheres with the N specific antibody bound thereto to remove the RBC's and N's in the station 190. The mixture is mixed for 30 seconds, then placed in a magnetic field for 10 seconds. The mixture with the N's and RBC's removed then is analyzed by the analyzer 194 resulting in the scattergram of FIG. 8B which provides a count of L's 73.5 (1), M's 21.7 (2), E's 3.4 (3) and B's 1.4 (4). The two counts are compared in the comparator 198, resulting in a five-part WBC differential count of L's 29.4, M's 8.0, N's 60.8, E's 1.2 and B's 0.6. A microscope comparison again was made resulting in counts of L's 29.4, M's 5.0, N's 65.0, E's 1.0 and B's of less than 1.0.

Figure 9A:
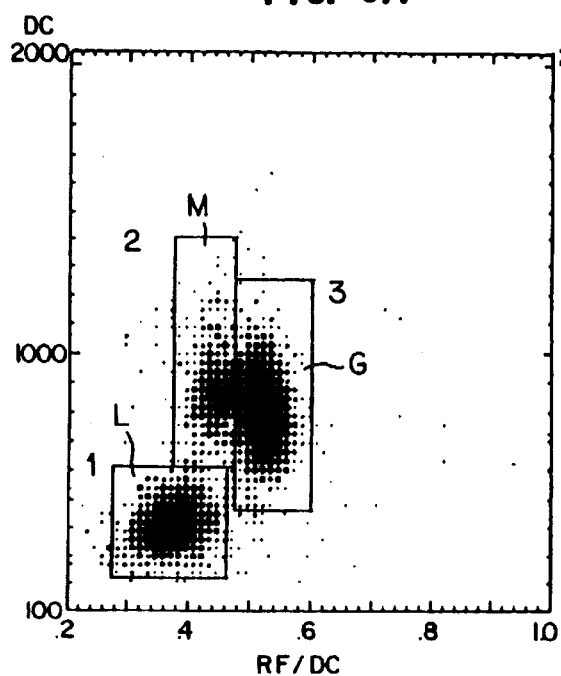
Figure 9B:
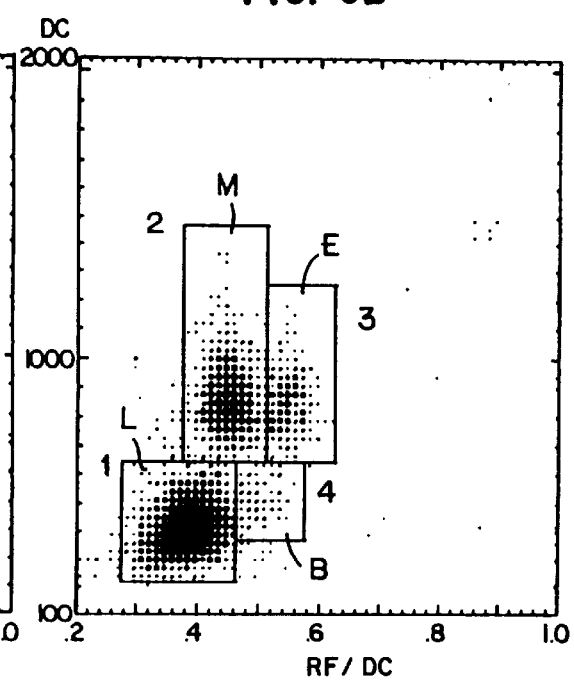

FIGS. 9A and 9B show scattergram results of a five-part WBC differential example similar to that of FIGS. 8A and 8B. A 20 microliter sample of whole blood was analyzed in the same steps described with respect to FIGS. 8A and 8B resulting in the scattergram of FIG. 9A providing a count of L's 35.4 (1), M's 14.6 (2) and G's 50.0 (3). The scattergram of FIG. 9B provides a count of L's 66.4 (1), M's 25.0 (2), E's 6.6 (3) and B's 2.0 (4). The resulting five-part WBC differential results in counts of 35.4 L's, 14.6 M's, 45.5 N's, 3.5 E's and 1.1 B's was compared to a microscope count of 36 L's, 11 M's, 49 N's, 3 E's and 1 B.

Figure 10A:
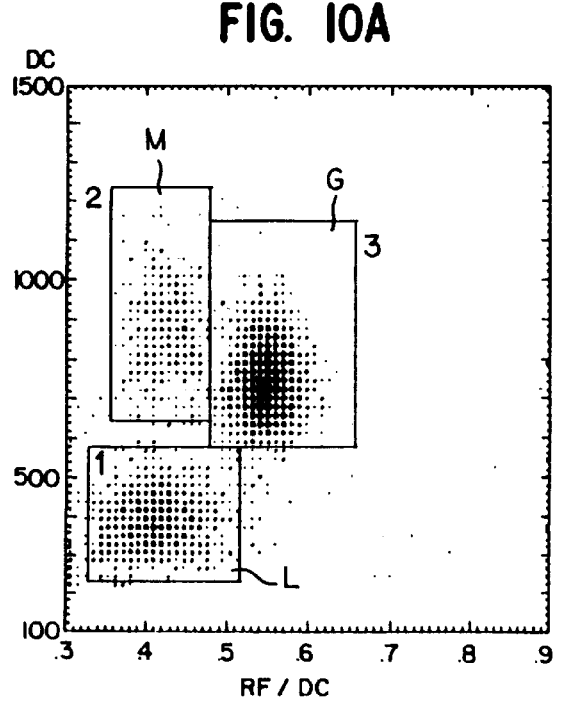
Figure 10B:
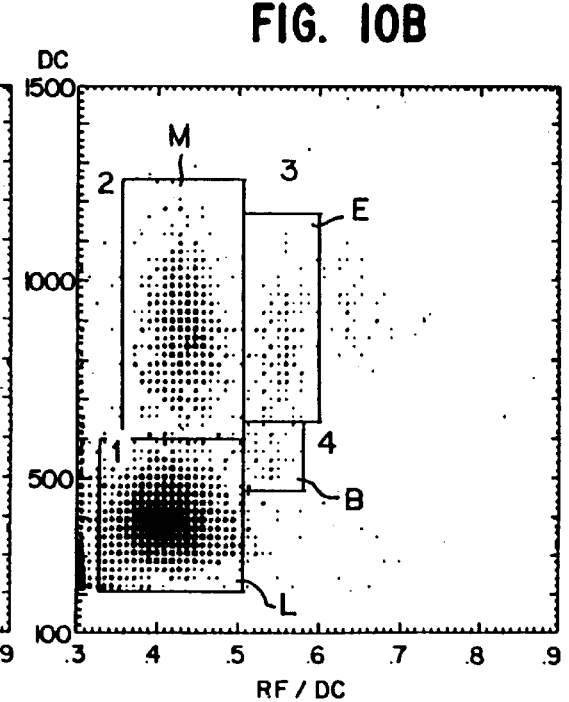

FIGS. 10A and 10B show scattergram results of a five-part WBC differential again similar to that of FIGS. 8A, 8B and 9A, 9B, however, in this example, lyse was utilized. In this example, 20 microliters of whole blood was combined with 80 microliters of buffer and 240 microliters of the RBC preferential lyse above referenced. The mixture is mixed for 6 seconds and then a quench is added. The time period is significant, because the lyse left unquenched for a period of time greater than about 10 seconds will start to affect the significant properties of the WBC's. The mixture with the RBC's removed is analyzed to provide the scattergram of FIG. 10A resulting in counts of L's 25.7 (1), M's 9.6 (2) and G's 65.0 (3).

A second portion of the mixture including a second 20 microliter sample of the whole blood is combined with 120 microliters of buffer and 10 microliters of magnetic microspheres with the N specific antibody bound thereto and mixed for 30 seconds and then placed in a magnetic field for 10 seconds. The RBC preferential lyse then is added to the N removed mixture which then is mixed for 6 seconds before it is quenched. The resulting scattergram FIG. 10B results in percentage counts of L's 74.6 (1), M's 21.6 (2), E's 2.9 (3) and B's 0.8 (4). The resulting five-part WBC differential results in percentage counts of L's 25.6, M's 9.6, N's 63.5, E's 1.06 and B's 0.3. Again a microscope comparison resulted in counts of L's 29.4, M's 5.0, N's 65.0, E's 1.0 and B's of less than 1.

Figure 11A:
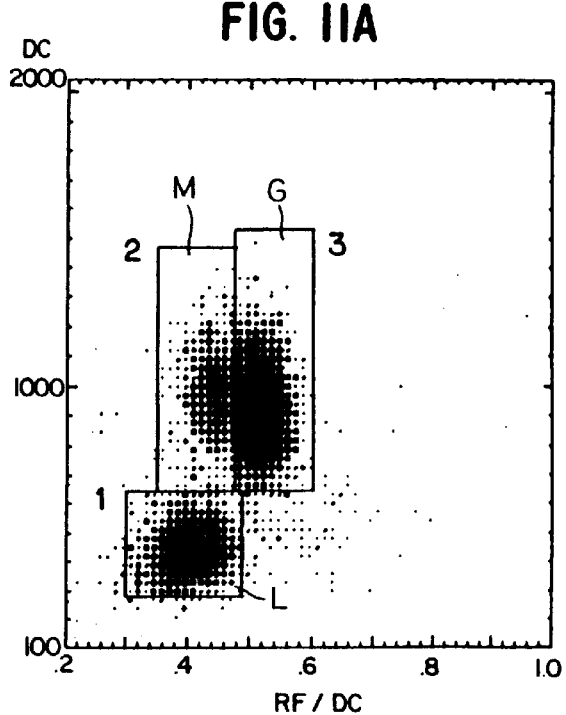
Figure 11B:
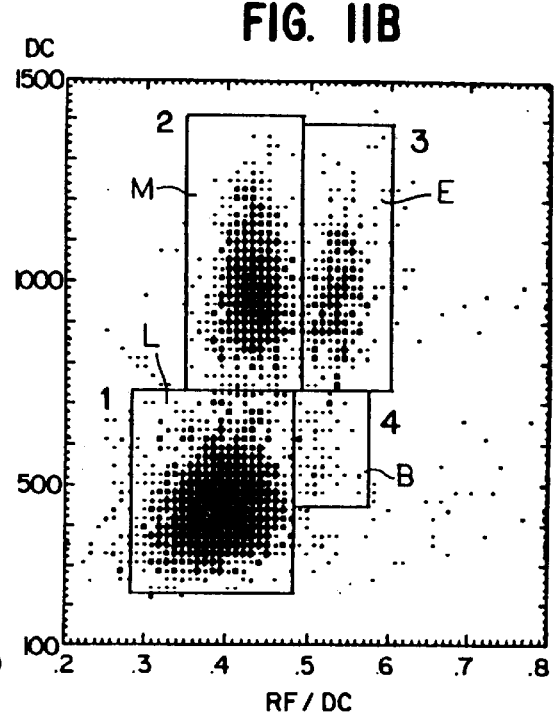

Another example of scattergram results of a five-part WBC differential similar to that of FIGS. 10A and 10B is illustrated in FIGS. 11A and 11B. A sample of whole blood had two samples simultaneously analyzed in the same steps described with a respect to FIGS. 10A and 10B. The scattergram of FIG. 11A provides a count of L's 31.9 (1), M's 17.6 (2) and G's 50.4 (3). The scattergram of FIG. 11B provides a count of L's 67.1 (1), M's 24.1 (2), E's 7.6 (3) and B's 1.2 (4). The resulting five-part WBC differential results in counts of 31.9 L's, 11.4 M's, 46.0 N's, 3.6 E's and 0.7 B's as compared to a microscope count of 36 L's, 11 M's, 49 N's, 3 E's and 1 B's.

Figure 12:
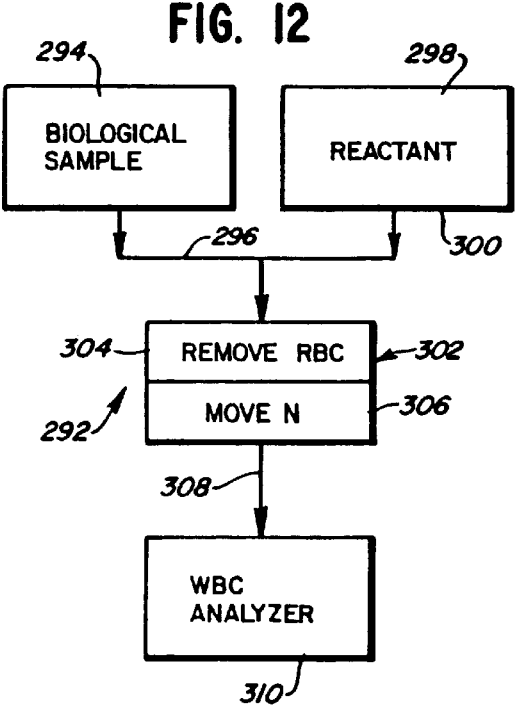

A yet still further embodiment of a cell population analyzing method and apparatus embodying the parent application is designated generally by the reference numeral 292 in FIG. 12. The analyzer 292 includes a biological sample 294, again including at least a first set of viable biological cells and including a buffer if desired.

The sample 294 is combined via a line 296 with at least one reactant 298 via a line 300. In the analyzer 292, the RBC's are removed and the N's are shifted sequentially or simultaneously in a functionally designated station 302. The RBC remove function is designated 304 and the N move or shift portion is designated 306 to indicate that the functions can be performed simultaneously or sequentially. The RBC's can be removed magnetically or with lyse or with a combination of the two as previously described. The N's are removed or shifted by adding microspheres having an N specific antibody bound thereto to the mixture.

Once the RBC's are removed and the N's are moved or shifted, then the resulting mixture is fed via a line 308 to an analyzer 310. In this case, the N's are shifted sufficiently from the patterns of the E's and B's that a five-part WBC differential of M's, L's, E's, B's and N's is directly obtained. The functions of the analyzer 292 can be performed on either of the instruments 56 and 210 or minor variations thereof.

Figure 13:
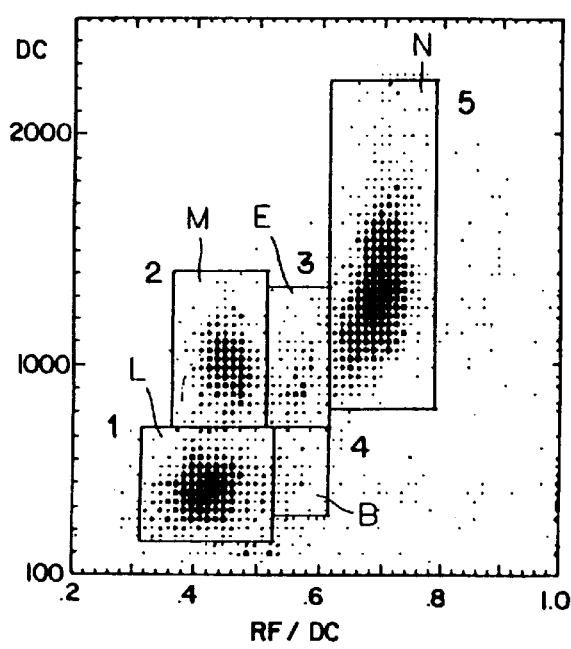

The scattergram results of one example of a direct five-part WBC differential in accordance with the analyzer 292 is illustrated in FIG. 13. In this example, the biological sample 294 is 20 microliters of a whole blood sample and the reactant 298 is 10 microliters of non-magnetic microspheres with the N specific antibody bound thereto combined with 100 microliters of buffer and mixed in the substation 306 for 30 seconds. The RBC preferential lyse, 10 microliters thereof, then is added to the mixture which is mixed in the substation 304 for 6 seconds after which the quench is added. The RBC removed and N shifted mixture then is analyzed by the analyzer 310 resulting in the scattergram of FIG. 13 which provides a direct count of 29.6 L's, 13.6 M's, 52.2 N's, 3.4 E's and 1.06 B's as compared to a microscope determination of 35 L's, 5 M's, 56 N's, 4 E's and no B's. In this particular example, the whole blood sample was also analyzed on a general cell counting instrument of Coulter Electronics, Inc., which resulted in 29 L's, 11.1 M's and 59.9 G's (N's, E's and B's).

Referring now to FIGS. 14–26D, the embodiments of the second parent application Ser. No. 285,856 are illustrated.

Figure 14:
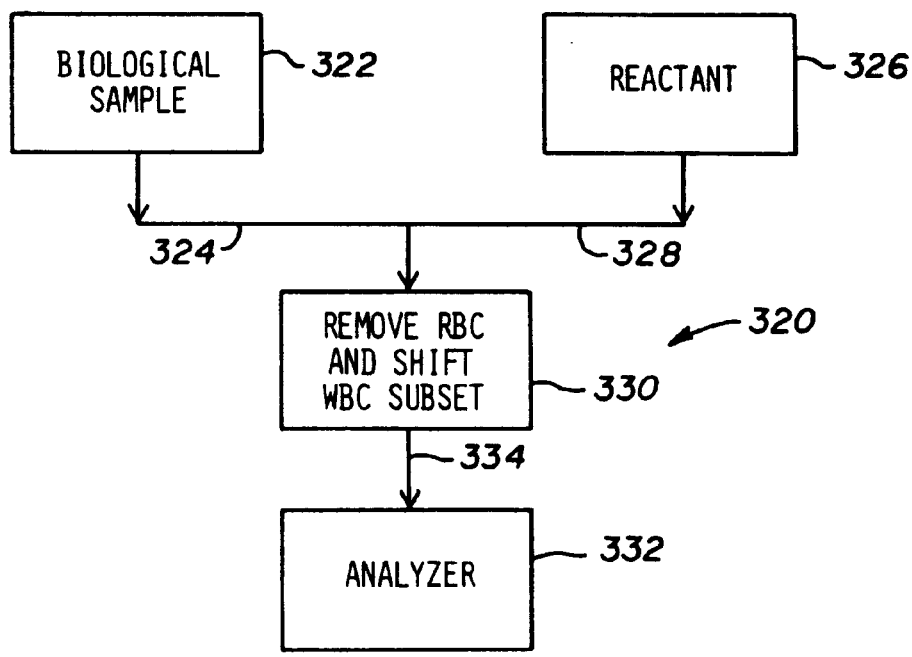

Referring to FIG. 14, a first embodiment of a WBC population subset analyzer method and apparatus of the second parent application is designated generally by the reference numeral 320. The analyzer 320 includes a biological sample 322, which contains at least a first set of viable biological cells (not illustrated), including at least one white blood cell population having at least one definable subset, such as in or from a whole blood sample. As utilized herein, WBC subsets are subsets of a WBC population to which specific monoclonal antibodies can be bound. A nomenclature now has been defined for the monoclonal antibodies by the World Health Organization and the International Immunology Society. The monoclonal antibodies are defined by a cluster of differentiation (CD) nomenclature which defines a particular specificity for a cell or group of cells and the monoclonal antibodies specific for that CD group. For example purposes only, four CD groups have been utilized in the following examples, CD4, CD8, CD2 and CD20. The CD nomenclature, specificity and some commercial sources of monoclonal antibodies are illustrated in Table I.

TABLE I

| Cluster of Differentiation | Antibody (Commercial Source)[b] | Specificity |
| --- | --- | --- |
| CD2(gp 50)[a] | T11 (Coulter) OKT11 (Ortho); Leu5[a] (BD) | E Rossette Receptor |
| CD4(gp 56) T | T4 (Coulter) OKT4[a] (Ortho); Leu3[a] (BD) | Helper/inducer |
| CD8(gp 32–33) | T8 (Coulter) OKT8 (Ortho); Leu2[a] (BD) | Cytotoxic/ Suppressor T |
| CD20(gp 35) | B1 (Coulter) Leu 16 (BD) | All B cells except for plasma cells, B cell tumors, except for myeloma, some non-T ALL cells |

[a]gp - glycoprotein, molecular weight in kilodaltons
[b]Coulter - Coulter Immunology Division of Coulter Corporation (Hialeah, Florida)
BD - Becton-Dickinson Immunocytometry Systems
Ortho - Ortho Diagnostic Systems (Raritan, New Jersey)

The cells of the biological sample 322 are to be involved in a biological reaction in a quantitative and/or qualitative determination or analysis. The sample 322 can include a buffer into which the cells are added.

The sample 322 is combined via a line 324 with at least one reactant 326 via a line 328. In the analyzer 320, the RBC's are removed from the mixture and simultaneously or sequentially at least one characteristic of at least one WBC subset is changed or shifted by a functionally designated RBC removing and WBC subset shifting station 330. As stated in the first parent application, the RBC's can be removed from the mixture by the station 330 in a number of ways, such as enumerated with respect to the station 20. Simultaneously or sequentially, in the same mixture portion, at least one WBC subset is bound to WBC microspheres having monoclonal antibodies specific to the subset thereon to modify (change or shift) the resultant opacity and/or volume parameters of the cells.

The mixture with the RBC's removed and the WBC subset population shifted, then is fed to an analyzer 332 via a line 34. The analyzer 332 can be substantially identical to the analyzer 22. The WBC subset of interest generally is related as a percentage of the WBC population of interest. The analyzer 320 thus provides a fast direct analysis of at least one characteristic of a selected subset of a WBC population. The analyzer 320 can be utilized where the shifted WBC subset is not obscured by other more numerous cells, or where the number of the shifted cells of the WBC subset is a sufficient percentage as to be identifiable, even though obscured.

Figure 15:
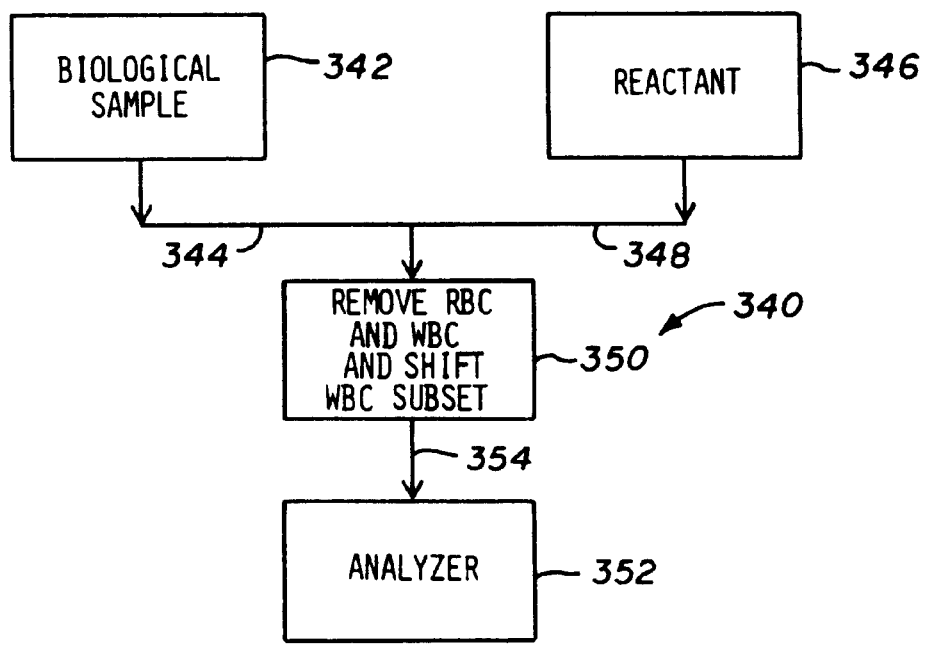

Referring to FIG. 15, a second embodiment of a WBC population subset analyzing method and apparatus of the second parent application is designated generally by the reference numeral 340. The analyzer 340 includes a biological sample, which contains at least a first set of viable biological cells (not illustrated), including at least one white blood cell population having at least one subset, such as in or from a whole blood sample. The cells of the biological sample 342 again are to be involved in a biological reaction in a quantitative and/or qualitative determination or analysis. The sample 342 can include a buffer into which the cells are added.

The sample 342 is combined via a line 344 with at least one reactant 346 via a line 348. In the analyzer 340, the RBC's are removed from the mixture and simultaneously or sequentially at least one characteristic of at least one WBC subset is changed or shifted by a functionally designated RBC removing and WBC subset shifting station 350. As previously stated, the RBC's can be removed from the mixture by the station 350 in a number of ways, such as enumerated with respect to the station 20. Again, simultaneously or sequentially, in the same mixture portion, at least one WBC subset is bound to microspheres to modify (change or shift) the resultant opacity and/or volume parameters of the cells.

At the same time or sequentially, at least one WBC population or subset is removed from the mixture. The WBC population or subset is removed so that the WBC subset of interest is not obscured by the population. This preferably is accomplished by magnetically removing the WBC population after they are bound to magnetic microspheres which include a monoclonal antibody bound thereto which is specific to the WBC population.

The mixture with the RBC's and the WBC population removed and the WBC subset populations shifted then is fed to an analyzer 352 via a line 354. The analyzer 352 again can be substantially identical to the analyzer 22.

Figure 16:
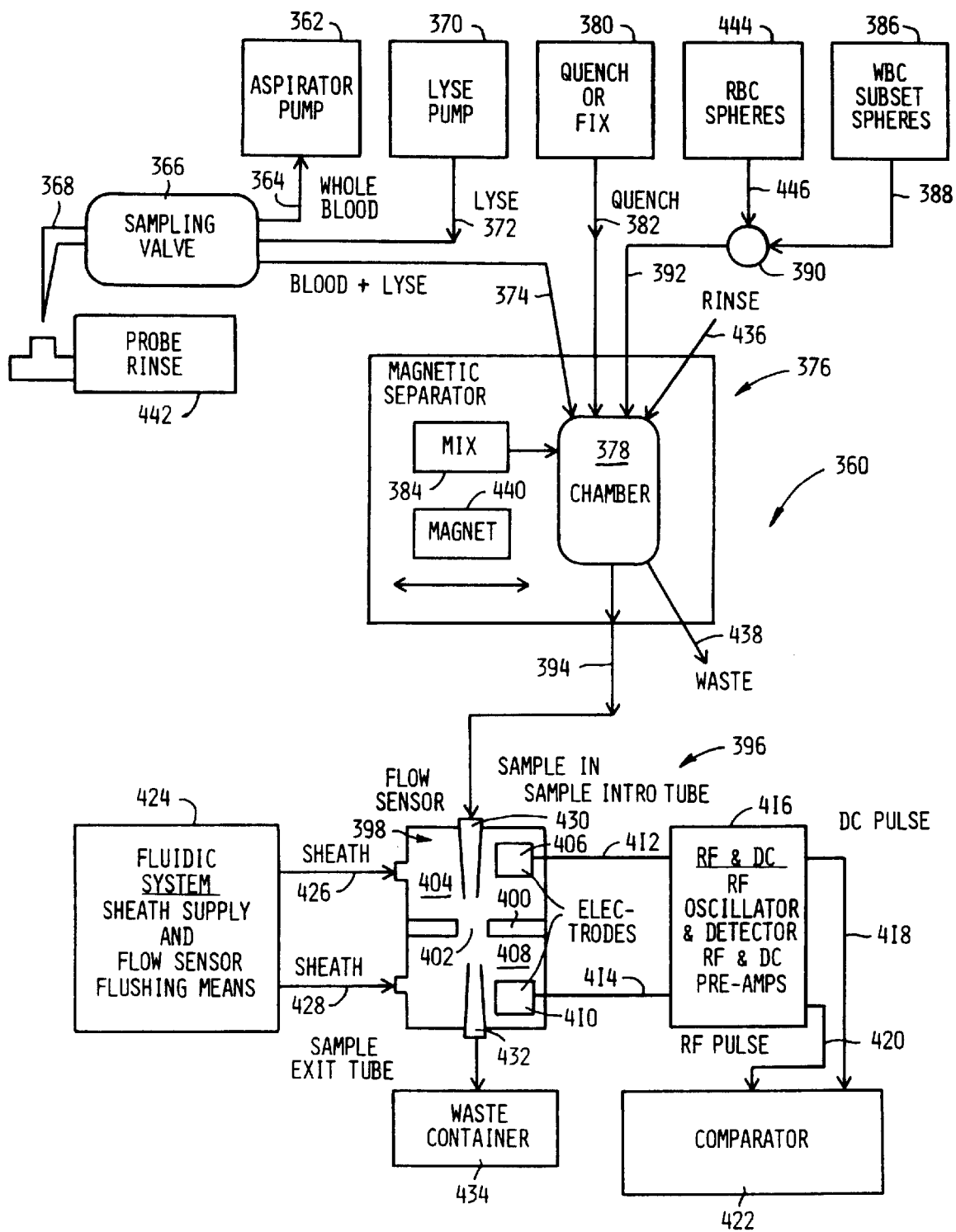

One specific embodiment of an analyzer instrument embodying the second parent application and which can accomplish the analyzing methods of the first and second analyzers 320 and 340, is designated generally by the reference numeral 360 in FIG. 16.

In the instrument 360, like the instrument 56, only one specific enumeration is illustrated, which can be varied in almost endless detail in accordance with the principles of the first parent application. Further, the instrument 360 is shown in generally functional detail and the specific embodiments can be structurally implemented in many known ways.

The instrument 360 includes an aspirator pumping mechanism 362 which is utilized to draw the biological sample of interest, for example the sample 322 or 342 into the instrument 360. The aspirator 362 is coupled via a line 364 to a sampling valve 366 which can be coupled to a sample probe 368. A lyse pump 370 can include the lyse, such as part of the reactant 326 or 346 and is also coupled to the valve 366 via a line 372. The valve 366 and the pump 362 can aspirate the biological sample 322 or 342 along with the lyse via the pump 370 when appropriate. Preferably, the biological sample 322 or 342 is added separately from the lyse.

The reactant mixture or the biological sample itself, then is fed via a discharge line 374 into a mixing apparatus 376. The mixer 376 includes a mixing chamber 378 into which the sample or reactant is fed. The analyzers 320 and 340 differ only slightly in operation and hence will be described together.

In operation, if the RBC's have been lysed by the lyse from the pump 370, then when the reaction is completed a quench or fix is supplied from a station 380 via a line 382. The RBC removal reaction then is completed. The reaction can be assisted by mixing the lyse and the sample in the chamber 378 as illustrated functionally at 384.

Either before, after or concurrently with the removal of the RBC's the WBC's are shifted and in the case of the analyzer 340, one WBC population or subset also is removed. The WBC subset is shifted by adding the specific WBC microspheres from a station 386 via a line 388, a valve 390 and a chamber line 392. The WBC microspheres are mixed with the mixture or the sample by the mixing mechanism 384.

The details of an appropriate mixing apparatus 376 can be substantially identical to the mixing apparatus 70. By utilizing the mixer 376 the reactions are greatly enhanced in speed without significantly damaging the properties of interest of the cells, such as, can occur by raising the reaction temperature. Further, the reactions generally are completed in significantly less than a few minutes and generally can be on the order of two minutes or less. This allows a rapid analysis of the automatic high volume analyzer instrument 360.

In the analyzer 320, the quenched reactant with the RBC's removed by the lyse (as from the station 20) and the modified WBC subset then is fed via a line 394 to a WBC analyzer 396 (i.e., analyzer 332). The analyzer 396 can be of many physical types in accordance with the counting and sizing techniques described by Wallace H. Coulter in U.S. Pat. No. 2,656,508 and embodied in the numerous commercial blood cell counters of the assignee, Coulter Electronics, Inc.

As previously described, the analyzer 396, in general, includes a flow sensor or sensing chamber 398. The chamber 398 includes a transducer 400 which has an aperture 402 therethrough. The chamber 398 includes a first portion 404 which has a first electrode 406 in contact with the fluid therein.

The chamber portion 404 and the electrode 406 communicate through the aperture 402 with a second chamber portion 408 having a second electrode 410 therein. The electrodes 406 and 410 are coupled via reactive leads 412 and 414 to an RF/DC source and sensing circuit 416. The circuit 416 couples both a DC, or low frequency current or signal, and a high frequency signal between the electrodes 406 and 410.

The low frequency signal is utilized to sense the amplitude of a signal pulse caused by a cell passing through the aperture 402. The high frequency signal is utilized to obtain the electrical opacity of the same cell passing through the aperture 402.

The measuring of the electrical opacity of cells was described by Wallace H. Coulter and Walter R. Hoff in U.S. Pat. No. 3,502,974 and several patents and publications of the assignee, Coulter Electronics, Inc., since that patent. One specific circuit which can be utilized herein is disclosed in U.S. Ser. No. 921,654, incorporated herein by reference.

The signals generated by the circuit 416 from the sensed cells are coupled via a DC signal lead 418 and an RF signal lead 420 to a comparator 422 (like the comparator 26).

The analyzer 396 can include a sheath flow to focus the cells in the sensor 398, in the well known manner. The sheath flow can be provided by a fluidic system 424, coupled to the sensor 398 by a pair of lines 426 and 428 in a known manner. The sample reaction mixture can be fed into the sensor 398 via an introduction tube 430 and can be fed from the sensor 398 via an exit tube 432 into a waste container 434.

Following each operation, the mixer 378 is cleaned or flushed via a rinse line 436 and exhausted through a waste line 438. Once the chamber 378 is cleaned, another sample or sample portion can be fed into the instrument 360.

In the analyzer 340, the operation is the same as the analyzer 320 with the addition of magnetic white blood cell population or subset microspheres. The WBC subset bound thereto then are removed by a magnetic field during and/or after the mixing process by a magnetic field or magnet 440. The field can be provided by electromagnetic means or by the magnet 440 being physically moved with respect to the chamber 378 to capture the magnetically bound WBC subset. The mixture without the bound WBC subset then is fed via the line 394 to the analyzer 396 in the manner previously described to obtain the analysis (like the analyzer 320).

The instrument 360 then is prepared to take the next sample for the next analysis. The probe 368 can be cleaned by a probe rinse mechanism 442 and the lines and chamber 378 can be flushed in a conventional manner. Each analysis of the succeeding sample mixture is obtained in a rapid and automatic fashion. The period between the analysis of succeeding sample mixtures can be on the order of five minutes or less.

Alternatively to the utilization of the lyse, in either of the analyzers 320 and 340, the sample 322 or 342 can be fed to the mixer 376 via the valve 366 without any lyse. In this case the RBC's can be removed magnetically by utilizing microspheres with the RBC specific antibody bound thereto from an RBC microsphere station 444 and fed to the valve 390 via a line 446 and hence to the chamber 376 via the line 392. Where no lyse is utilized, the bound RBC's also are magnetically removed by the magnet 440 after mixing in a manner substantially identical to the magnetically bound WBC's described above.

Further, in a second case to promote the speed or efficiency of the reaction, a reaction mixture of the sample with both the RBC lyse and with the RBC magnetic beads can be utilized. The reaction mixture is mixed, the lyse is quenched and the bound RBC's are magnetically removed and then the WBC's are analyzed as previously described.

Referring now to FIGS. 17A and 17B, two sets of results depicted in scattergrams obtained from a whole blood sample utilizing a prototype analyzer similar to the instrument 360 are illustrated. Two WBC populations are removed and the $T_8$ subset is directly analyzed. The $T_8$ subset is the cells or formed bodies which have the receptor or antigen to which the $T_8$ specific antibody binds to. In the Figures., these are designated as $T_8^+$. The cells or formed bodies which do not have the receptor or antigen to which the $T_8$ specific antibody binds to are designated as $T_8^-$. In these examples, the biological medium 342 was a 20 microliter sample of whole blood utilized with the mixer 376. In both FIGS. 17A and 17B, the 20 microliter sample of whole blood, medium 342, was combined with 40 microliters of magnetic microspheres with the RBC specific antibody bound thereto, combined with 120 microliters of buffer solution and 10 microliters of magnetic microspheres with an N and E specific antibody bound thereto, combined with 30 microliters of buffer solution which together form the reactant 346. One such exemplary N and E specific antibody is disclosed in U.S. Ser. No. 068,618, entitled *MONOCLONAL ANTIBODY SPECIFIC TO A COMMON DETERMINANT SITE OF NEUTROPHILS AND EOSINOPHILS*, filed Jun. 3, 1987, now U.S. Pat. No. 4,865,971 which is incorporated herein by reference.

The magnetic microspheres can be of any suitable type and in the example are polystyrene magnetic microspheres of 0.7 micron diameter, with a weight to volume of 10% solids, sold by Seradyn, Inc. of Indianapolis, Ind. The reaction mixture then was mixed in the mixer 376 for 10 seconds, placed in the magnetic field of the magnet 440 for 15 seconds and then the resulting mixture with the RBC's, E's and N's removed was analyzed in the analyzer 396. The resulting scattergram A is illustrated in FIG. 17A.

The scattergram of FIG. 17B results from the same procedure with the addition of 12.5 microliters of non-magnetic microspheres with a $T_8$ specific antibody bound thereto combined with 12.5 microliters of buffer solution to form the reactant 346. The $T_8$ specific antibody is sold under the Trademark COULTER CLONE@ by Coulter Immunology Division of Coulter Corporation. The non-magnetic microspheres again can be of any suitable type and in the examples are surfactant free sulfated polystyrene latex microspheres of 1.78 micron diameter with a weight to volume of 8% solids, sold as IDC microspheres by Interfacial Dynamics of Portland, Oreg.

The addition of the $T_8$ microspheres shifts the bound CD8 cells to an area B where they separately can be identified and counted as seen by comparing the scattergram of FIGS. 17A and 17B. In FIG. 17A the CD8 cells are hidden by the remaining WBC's. The N's and E's are removed from the scattergrams or they would obscure the identification of the shifted CD8 cells in FIG. 17B. FIG. 17A illustrates the removal of the N's and E's, while FIG. 17B then clearly illustrates the shift of the CD8 bound cells from area A to area B. The buffer solution can be phosphate buffered saline sold by Sigma Chemical Company of St. Louis, Mo.

Figure 18A:
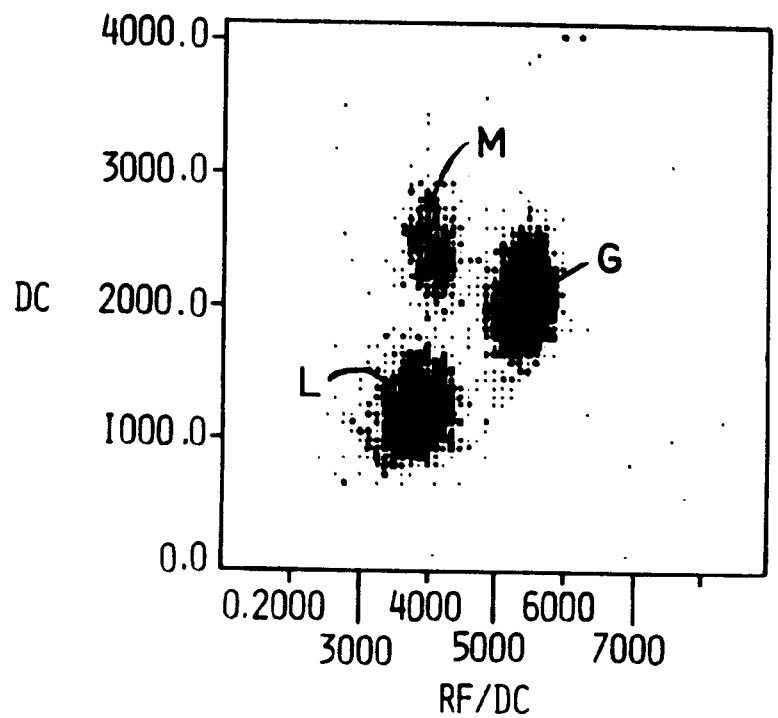
FIG. 18A is a scattergram of the L, M and G populations
Figure 18B:
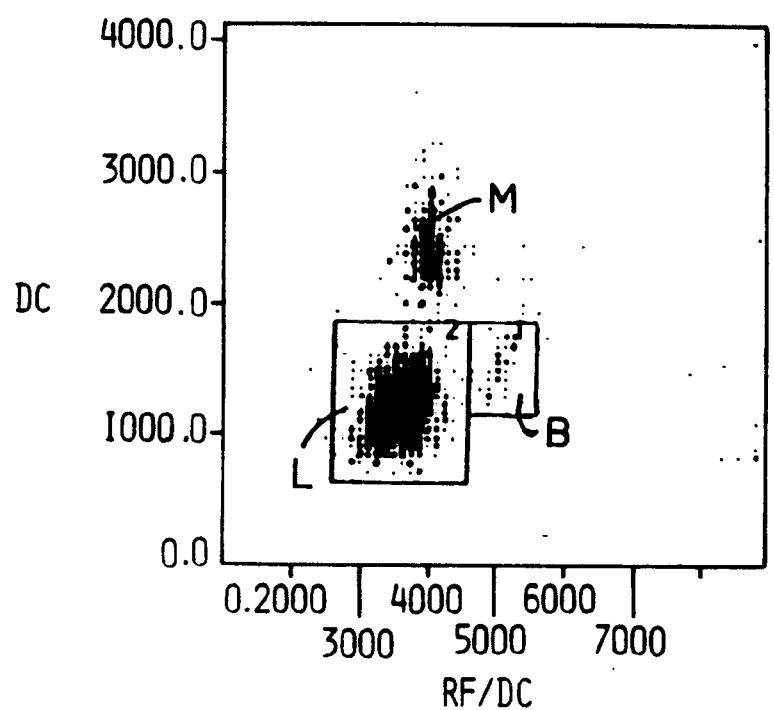
FIG. 18B is a scattergram of the L, M and B populations utilizing a prototype analyzer system similar to that illustrated with respect to FIG. 16.
Figure 19A:
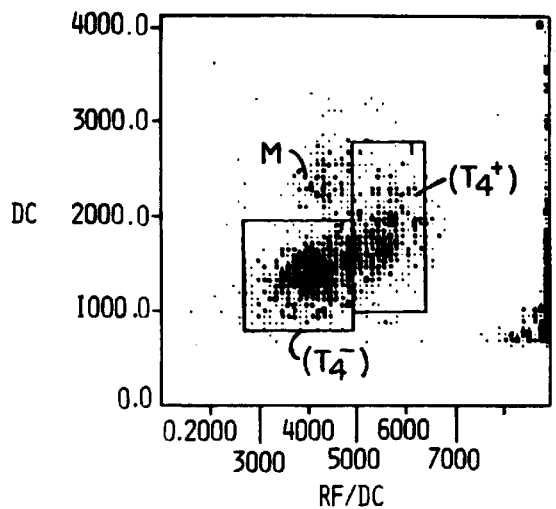
FIGS. 19A–D, 20A–D and 21A–D are scattergrams of the CD4, CD8, CD2 and CD20 subset populations of samples of different patients.
Figure 19B:
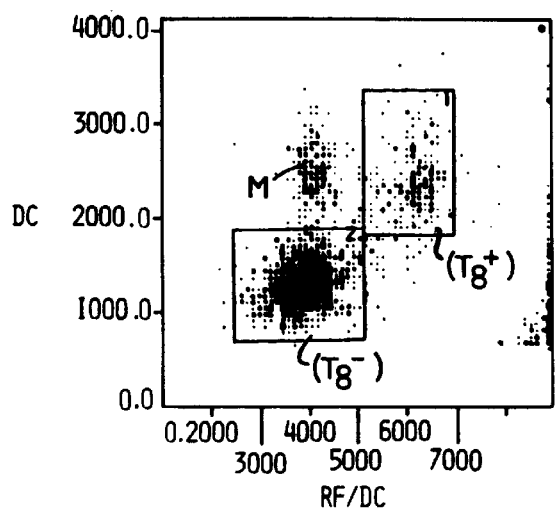
Figure 19C:
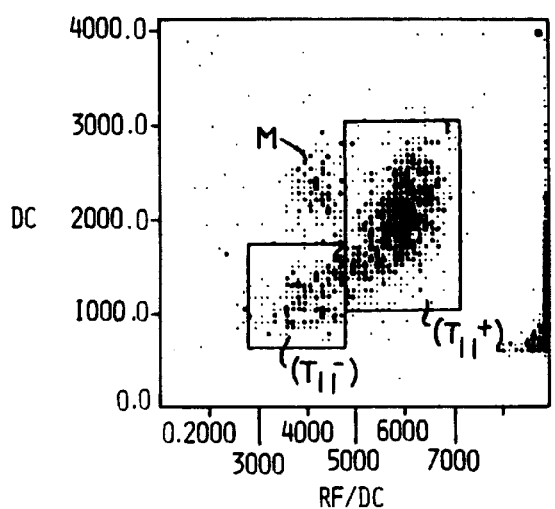
Figure 19D:
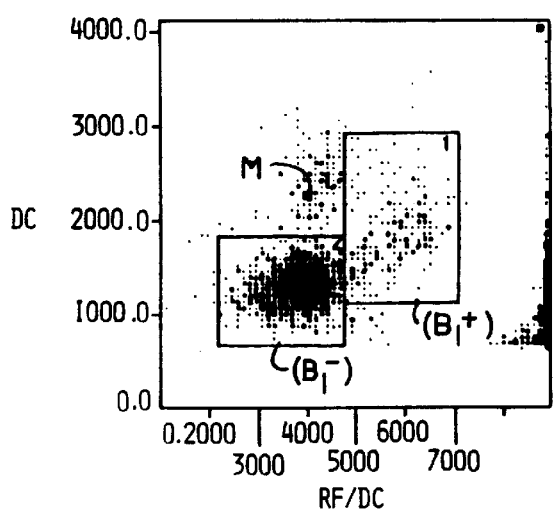
Figure 20A:
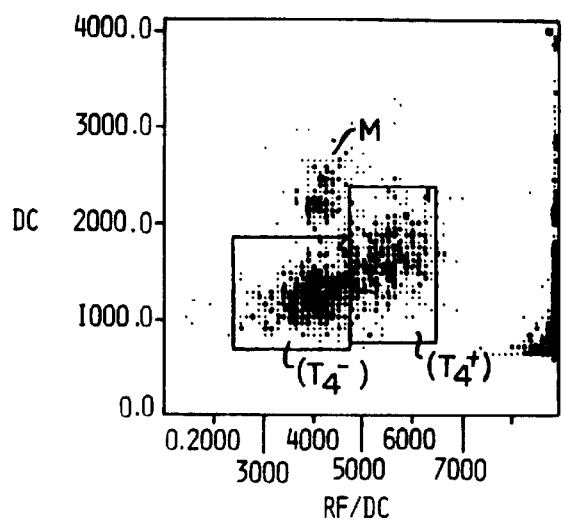
Figure 20B:
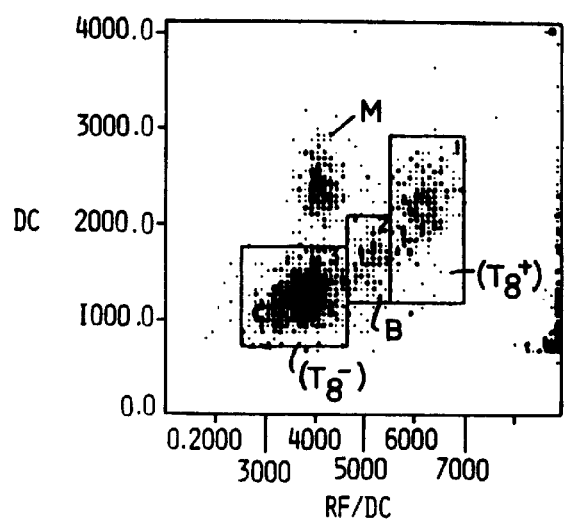
Figure 20C:
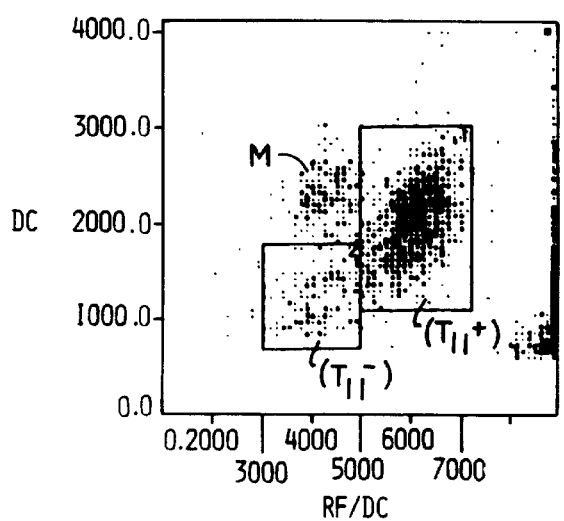
Figure 20D:
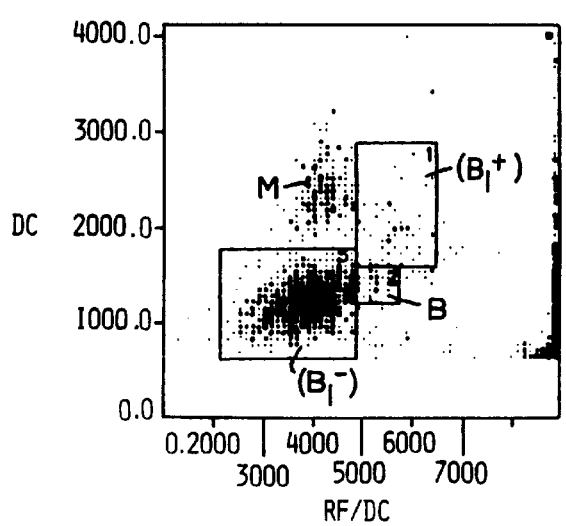
Figure 21A:
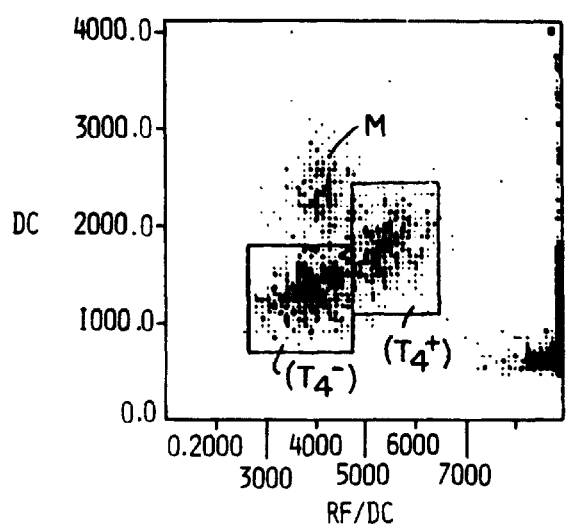
Figure 21B:
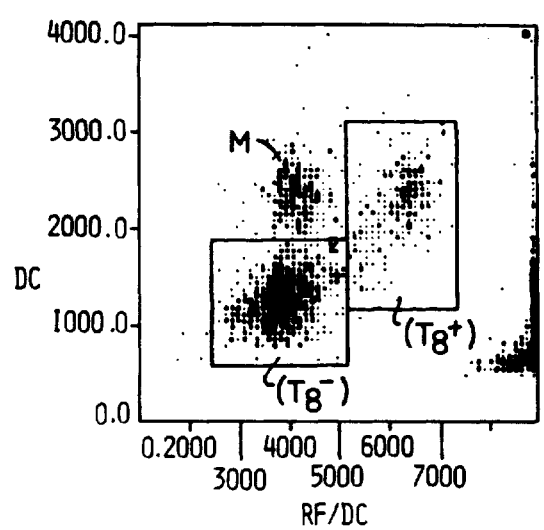
Figure 21C:
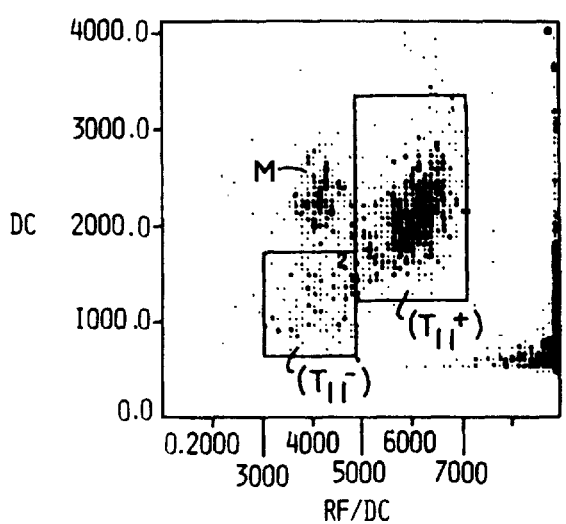
Figure 21D:
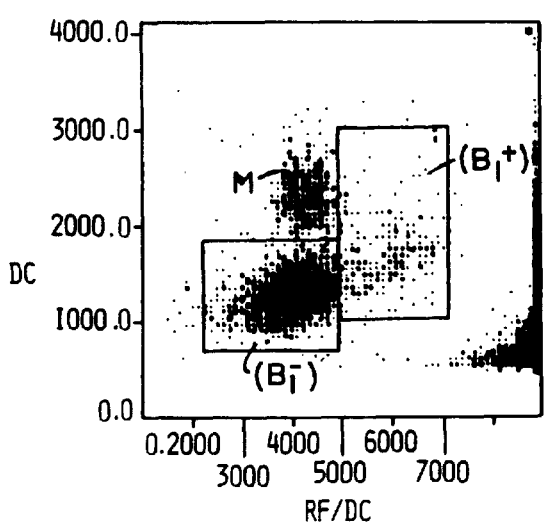

FIG. 18A further illustrates the normal scattergram or 3 parameter histogram positioning of the M, L and G cell populations from the analyzer 352. Without removal of the G's, as seen in FIG. 17B, the area B of the shifted WBC subset would be obscured by the G's, which are far more numerous in number. FIG. 18B is a scattergram illustrating the WBC populations M, L and B remaining after removal of the E's and N's. Although the B's still may partially obscure the area of interest, their percentage number of the WBC populations is of a small enough order to not substantially affect the desired calculation of the subset, percentage. However, the B's contribution can be subtracted from the subset percentage if so desired.

Referring now to FIGS. 19A–D, 20A–D and 21A–D, the direct subset analysis of the CD2, CD4, CD8 and CD20 WBC subset populations of respective samples from three different patients is illustrated. In the case of each subset population, 28 microliters of a whole blood sample was combined with 20 microliters of magnetic microspheres (2.5% weight per volume solution) with the N and E specific antibody bound thereto. In addition, non-magnetic microspheres with the respective monoclonal antibody for the respective WBC subset are also combined with the sample. The respective amounts of $T_4$, $T_8$, $T_{11}$ or $B_1$ coated microspheres are 40 microliters each. (1% weight per volume solution for each one). Each respective total mixture, i.e., N and E microspheres with $T_8$, for example, is combined with a buffer solution of phosphate buffered saline, 1% bovine serum albumin, pH of 7.2 to 7.4 for a total volume of 150 microliters. Each respective mixture is mixed in the chamber 378 by the mixer 376 for two minutes and then placed in the magnetic field 440 for one minute. In these examples, the RBC's are removed sequentially utilizing the lyse above referred to. The WBC microspheres are first added, then the RBC's are removed by lysing with 300 microliters of lyse, such as Erythrolyse lytic reagent sold by Coulter Electronics, such as from the lyse source 370. The mixture then is quenched with 120 microliters of quench, such as Stabilyse, a leukocyte preservative also sold by Coulter Electronics, from the source 380 and then fed to the analyzer 396 for analysis.

The right-hand block (1) in each scattergram represents the respective WBC subset population of interest. The blocks 1, 2, 3, etc. illustrated in the Figures are visually or automatically fit around the WBC population or subset of interest.

The results were compared utilizing conventional flow cytometry and gave the following comparative results in percentages for the three samples by the method of the invention (SHIFT) vs. flow cytometry (CYT).

|  | $T_4$ (FIG. 19A) | | $T_8$ (FIG. 19B) | | $T_{11}$ (FIG. 19C) | | $B_1$ (FIG. 19D) | |
| --- | --- | --- | --- | --- | --- | --- | --- | --- |
|  | Shift | CYT | Shift | CYT | Shift | CYT | Shift | CYT |
| Patient Sample 1 | 51 | 52 | 18 | 22 | 82 | 76 | 15 | 13 |

|  | $T_4$ (FIG. 20A) | | $T_8$ (FIG. 20B) | | $T_{11}$ (FIG. 20C) | | $B_1$ (FIG. 20D) | |
| --- | --- | --- | --- | --- | --- | --- | --- | --- |
|  | Shift | CYT | Shift | CYT | Shift | CYT | Shift | CYT |
| Patient Sample 2 | 53 | 54 | 32 | 29 | 89 | 83 | 6.5 | 7.5 |

|  | $T_4$ (FIG. 21A) | | $T_8$ (FIG. 21B) | | $T_{11}$ (FIG. 21C) | | $B_1$ (FIG. 21D) | |
| --- | --- | --- | --- | --- | --- | --- | --- | --- |
|  | Shift | CYT | Shift | CYT | Shift | CYT | Shift | CYT |
| Patient Sample 3 | 46 | 46 | 24 | 18 | 86 | 81 | 11 | 10 |

Figure 23A:
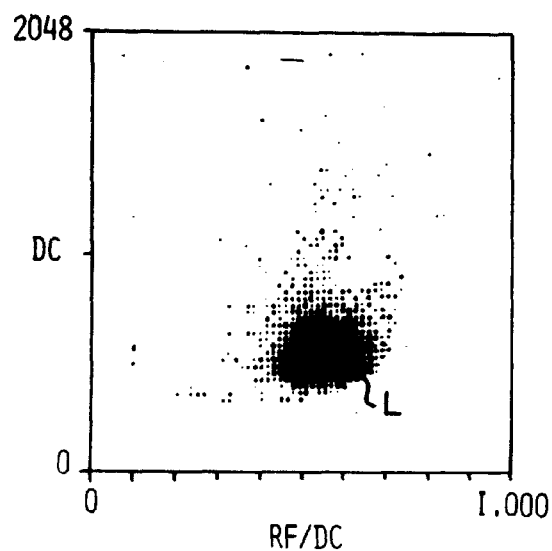
FIGS. 23A–D are scattergrams illustrating a direct WBC subset analysis utilizing one microsphere bound to the WBC subset of interest and a second microsphere bound to the first microsphere.
Figure 23B:
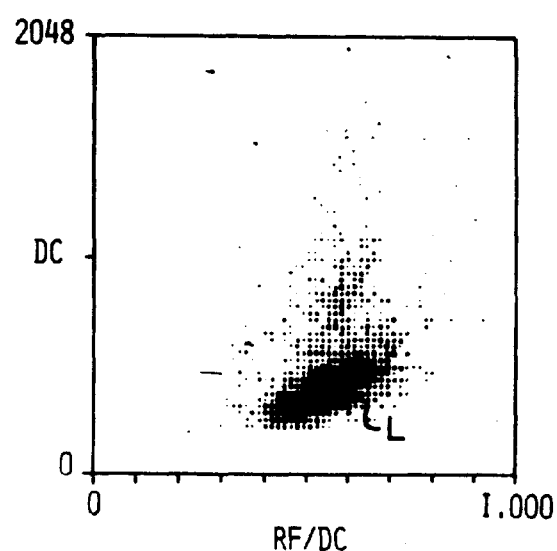
Figure 23C:
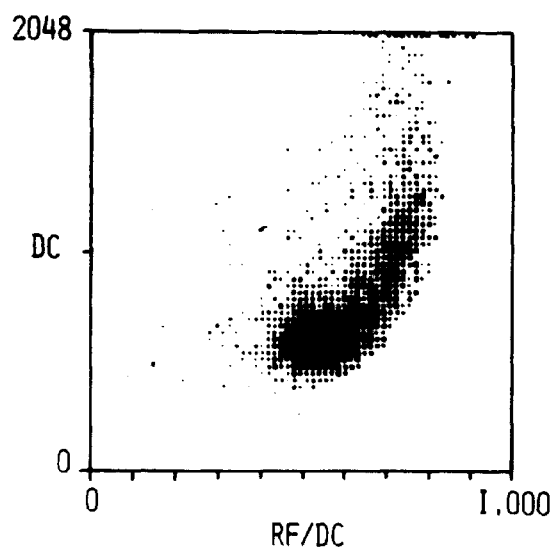
Figure 23D:
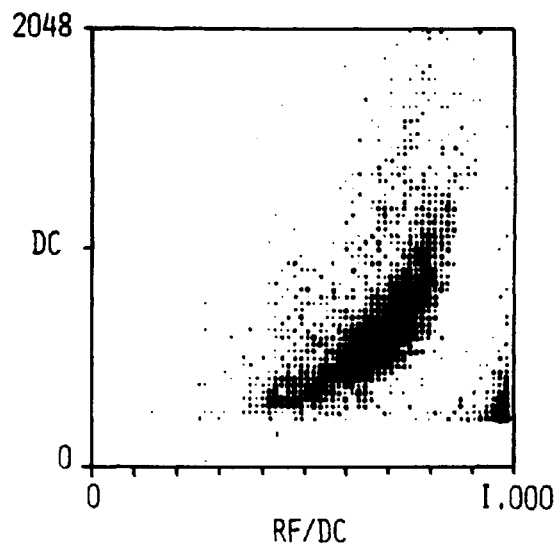

FIG. 22A also illustrates the normal scattergram or 3 parameter positioning of the M, L and G cell populations from the analyzer 352. Without removal of the N's and E's, the CD4 cell population would be obscured. By shifting the N's and E's with the N and E specific monoclonal antibody microspheres to an area or block 1 illustrated in FIG. 22B, the CD4 population can be shifted and viewed in the block or area 2. This area would have been obscured by the N's and E's as seen in FIG. 22A. In this example for FIG. 22C, 28 microliters of a whole blood sample were combined with 50 microliters of 2.2 micron microspheres with the N and E specific monoclonal antibody bound thereto and 50 microliters of microspheres with $T_4$ specific monoclonal antibody bound thereto and 22 microliters of diluent. FIG. 22B was the same without the $T_4$ microspheres and with 72 microliters of diluent and FIG. 22A was the same without any microspheres and 122 microliters of diluent. Referring to FIGS. 23A–D, direct WBC analysis utilizing a plurality of microspheres bound to the WBC subset of interest is illustrated. FIGS. 23A and 23B respectively illustrate scattergrams of only the L population with the $T_4$ WBC subset and the $T_{11}$ WBC subset each shifted with 0.8 micron non-magnetic microspheres. The shift is insufficient to differentiate the WBC subset population in FIGS. 23A and 23B. FIGS. 23C and 23D respectively illustrate scattergrams of only the L population with the $T_4$ WBC subset and the $T_{11}$ WBC subset shifted by being bound to both a 0.8 micron and a 2.2 micron microsphere. The 2.2 micron microsphere is bound to the 0.8 micron microsphere by having Goat anti-mouse IgG antibody bound thereto, which binds to the $T_4$ or $T_{11}$ antibody bound to the 0.8 micron microsphere.

Figure 24A:
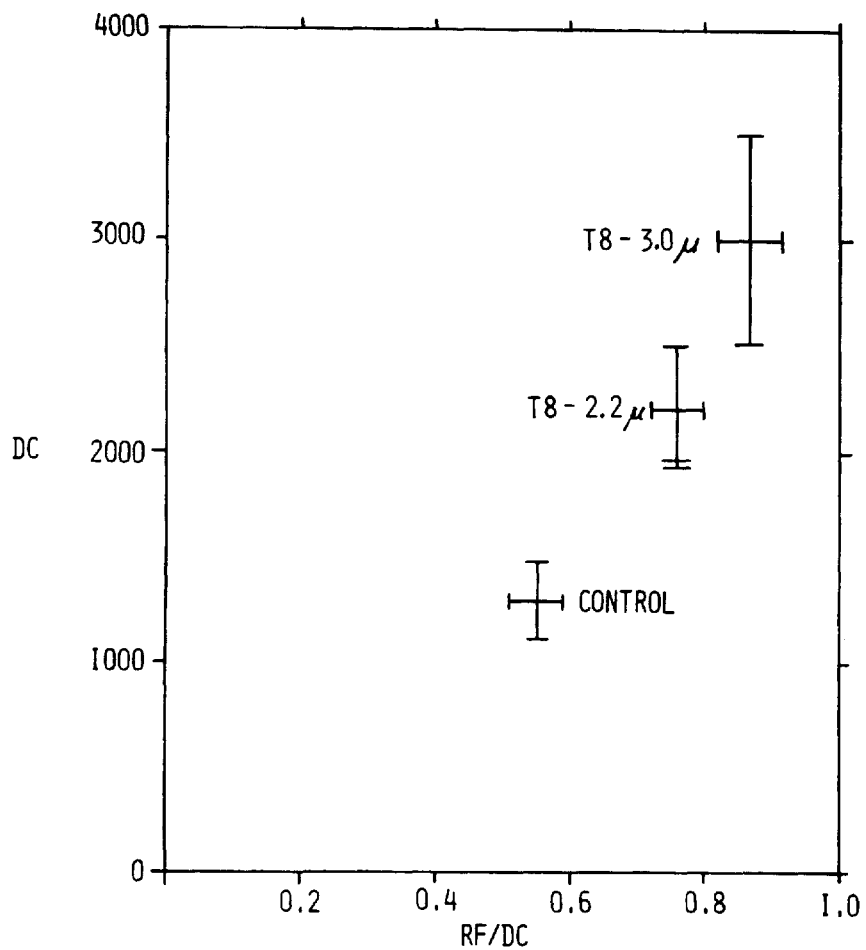
FIGS. 24A–C are scattergrams illustrating the effect of the size of the microsphere utilized in the shifting analysis of the parent application.
Figure 24B:
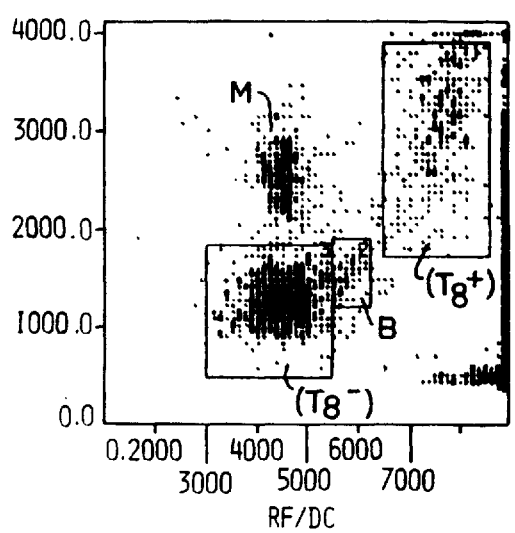
Figure 24C:
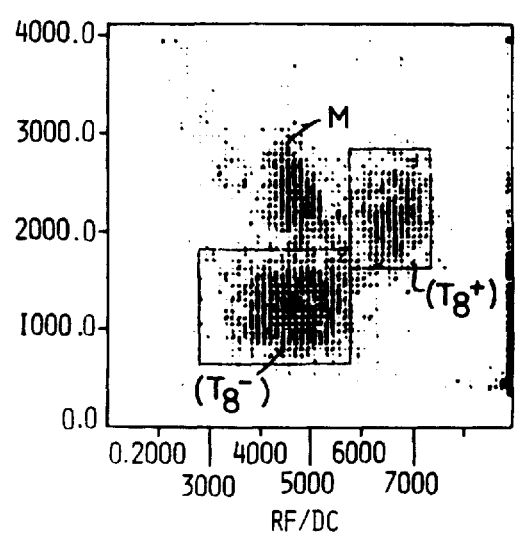

The effect of the size of the non-magnetic microsphere bound to the WBC subset of interest is illustrated in FIGS. 24A–C. In this example, a 28 microliter sample of whole blood was combined with 10 microliters of magnetic microspheres having the N and E specific antibody bound thereto (2.5% weight per volume solution) and 40 microliters of non-magnetic microspheres having the $T_8$ specific antibody bound thereto (1% weight per volume solution). The $T_8$ microspheres were of two different sizes to illustrate the difference in the shift on the scattergram. A buffer solution again was added to form a mixture volume of 150 microliters. The mixture was mixed for 2 minutes and placed in the magnetic field for 1 minute. The resultant N and E removed mixture then was lysed to remove the RBC and then analyzed. FIG. 24A illustrates a control WBC subset without a microsphere attached thereto, a $T_8$ WBC subset with a 2.2 micron non-magnetic microsphere bound thereto and a $T_8$ WBC subset with a 3.0 micron non-magnetic microsphere bound thereto. The width and height illustrate the standard deviation of the detected signal. FIG. 24B is a scattergram illustrating the $T_8$ WBC subset shift with the 3.0 micron microspheres bound thereto, while FIG. 24C is a scattergram illustrating the $T_8$ WBC subset shift with the 2.2 micron microspheres bound thereto. The analyzed percentage of the $T_8$ WBC subset for the different microspheres were respectively, 20.9 and 19.3. The larger microsphere clearly generated a more distinct scattergram pattern as illustrated by FIG. 24B.

Figure 25A:
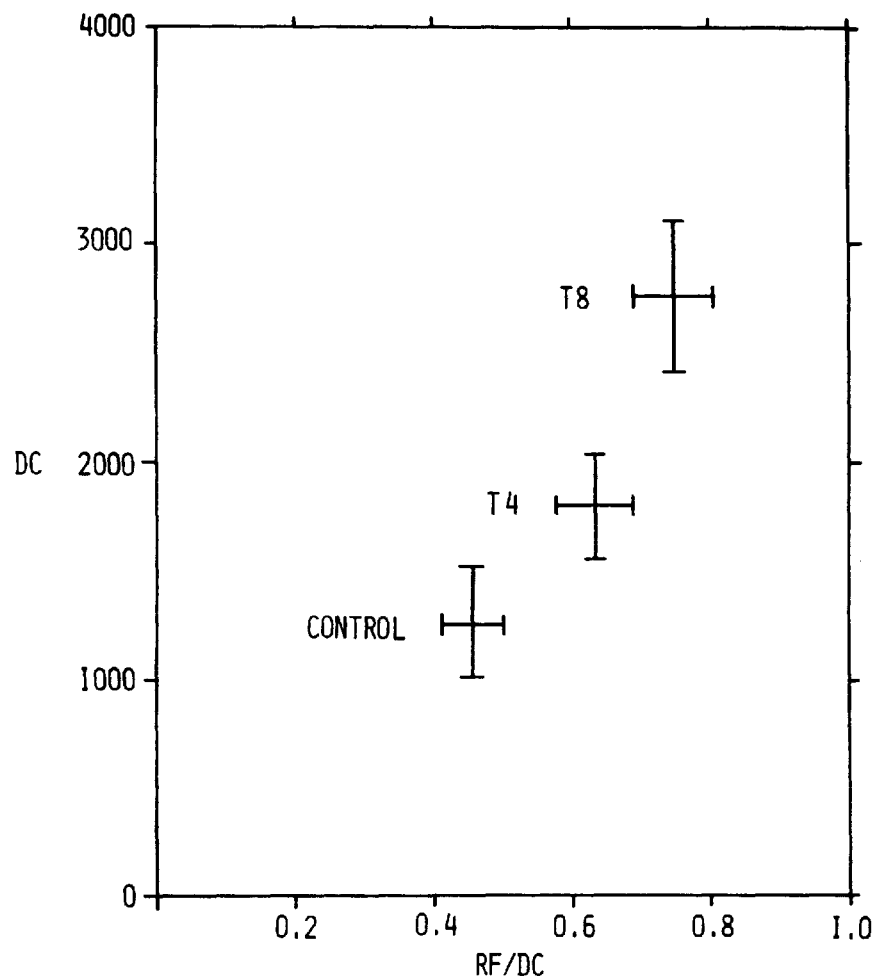
FIGS. 25A–D are scattergrams illustrating a simultaneous analysis of two WBC subset populations by the techniques of the parent application.
Figure 25B:
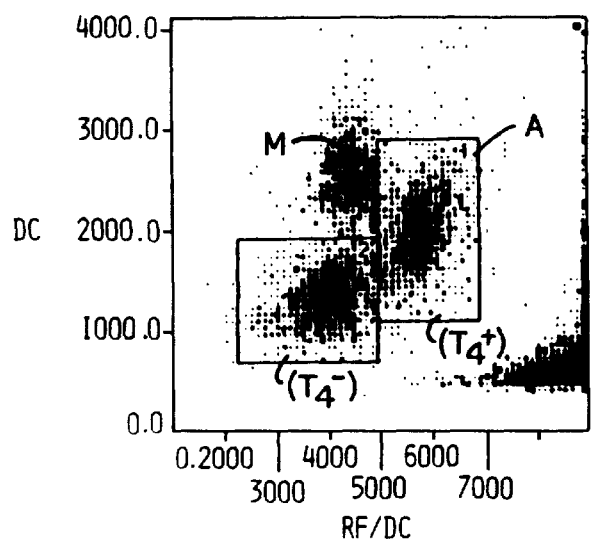
Figure 25C:
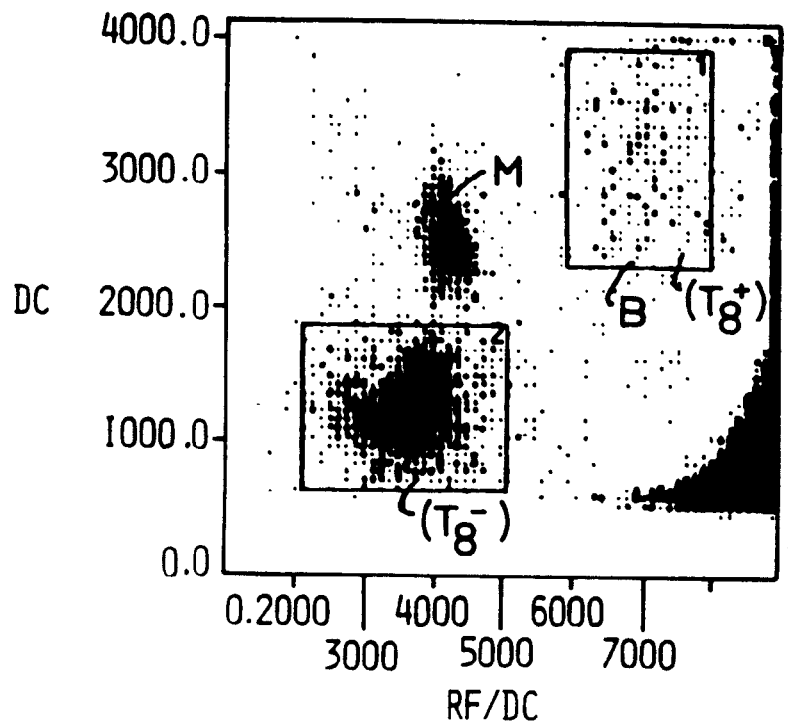
Figure 25D:
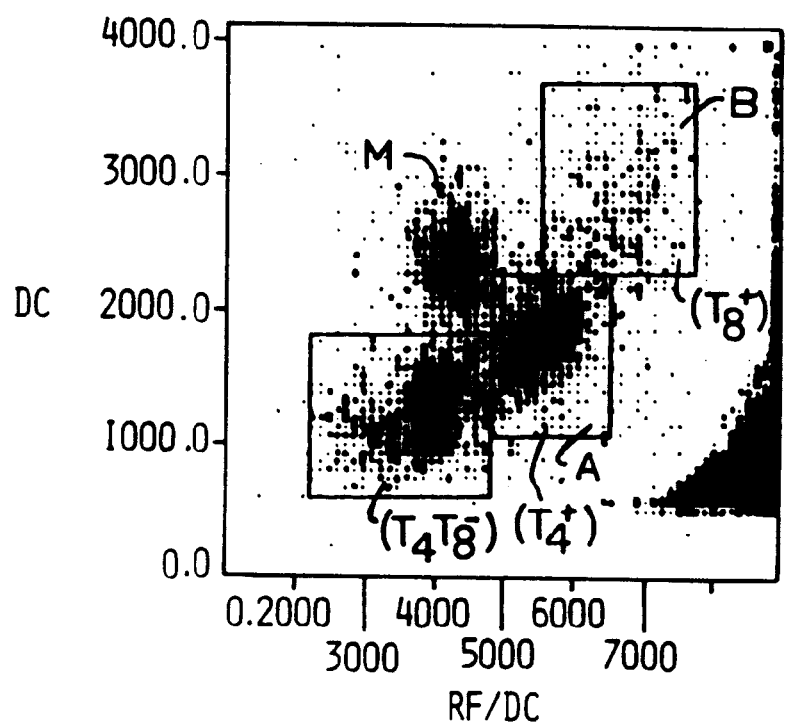

Referring now to FIGS. 25A–D, the simultaneous direct analysis of two WBC subset populations is illustrated in accordance with the second parent application. In this example, 28 microliters of a whole blood sample was combined with 10 microliters of magnetic microspheres having the N and E specific antibody bound thereto, 52 microliters of buffer solution and 40 microliters of non-magnetic 3.0 micron microspheres with the $T_8$ specific antibody bound thereto and mixed for 2 minutes. The mixture then was placed in the magnetic field for 1 minute and then the resultant N and E removed mixture was lysed to remove the RBC's and then analyzed. FIG. 25A illustrates a control WBC subset sample without a microsphere bound thereto, a $T_4$ reading with a 2.2 micron non-magnetic microsphere bound thereto and a $T_8$ reading with a 3.0 micron non-magnetic microsphere bound thereto. This illustrates the separation between the two shifted WBC subset populations. FIG. 25B is a scattergram analysis with only the $T_4$ WBC subset population bound to the 2.2 micron microspheres shifted to area A and FIG. 25C is a scattergram analysis with only the $T_8$ WBC subset population bound to the 3.0 micron microspheres shifted to area B. FIG. 25D illustrates a scattergram analysis with both the $T_4$ and $T_8$ WBC subset populations shifted to the respective areas A and B. This allows a simultaneous analysis of both the $T_4$ and $T_8$ subset populations.

Figure 26A:
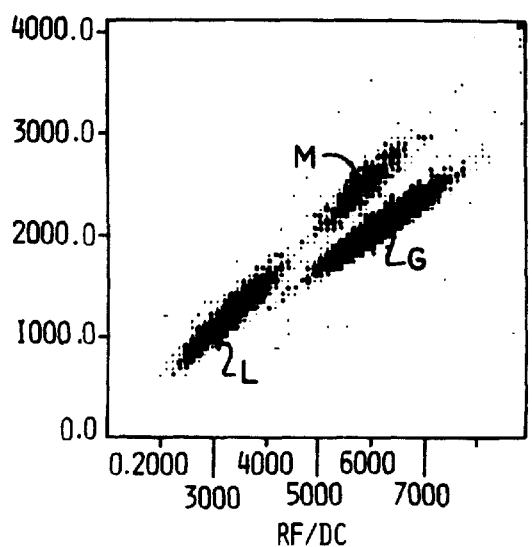
Figure 26B:
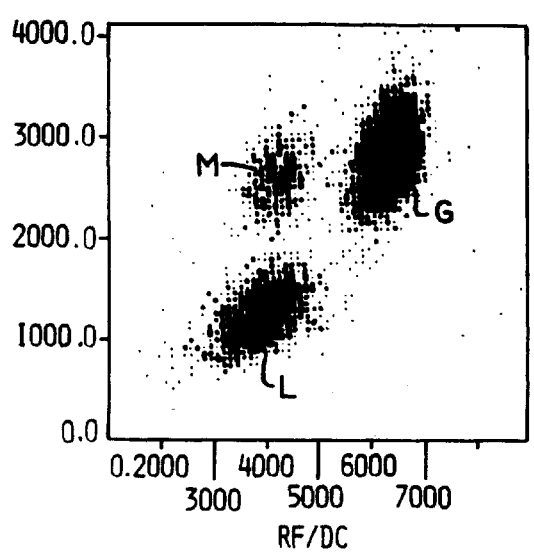
Figure 26C:
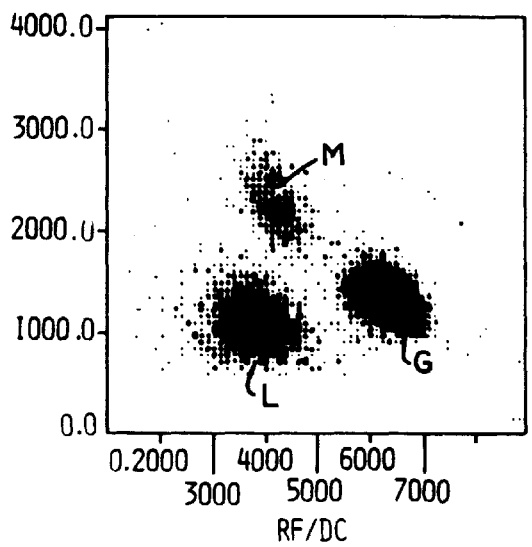
Figure 26D:
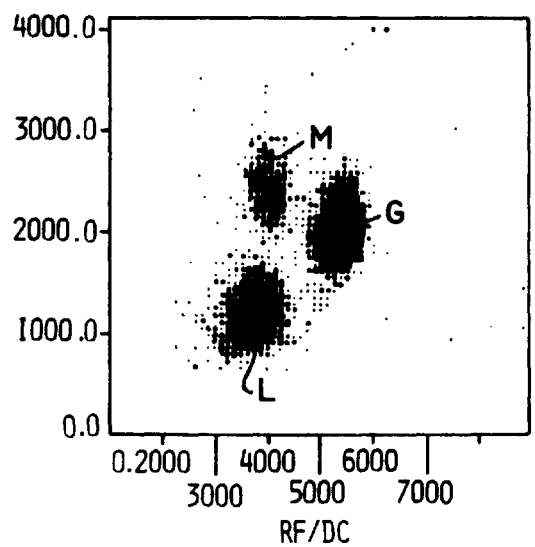

Referring now to FIGS. 26A–D, three populations of L's, M's and G's are illustrated on four different scattergrams utilizing different parameters. Although the previous examples have been illustrated utilizing DC vs. opacity (RF/DC), the scattergrams can be formed utilizing virtually any two different parameters. FIG. 26A illustrates a scattergram utilizing DC vs. RF alone, FIG. 26B utilizes RF vs. opacity, FIG. 26C utilizes DC-RF vs. opacity and FIG. 26D utilizes DC vs. opacity as previously illustrated. Further, although DC vs. RF or RF/DC has been utilized, any two different frequencies are adequate as long as the signals are separable from each other, because of their frequency spectrum location and/or the difference in phase relationship. Opacity is a preferable parameter since it essentially is a normalization of the RF signal. Clearly, as illustrated in FIGS. 26A–D, the presentation of the data can be varied as desired. DC is a function of volume of the cell or formed body sensed, while RF is a function of the internal conductivity and volume of the sensed cell or formed body.

Referring now to FIGS. 27–46, the embodiments of the third parent application, Ser. No. 339,156 are illustrated.

Figure 27:
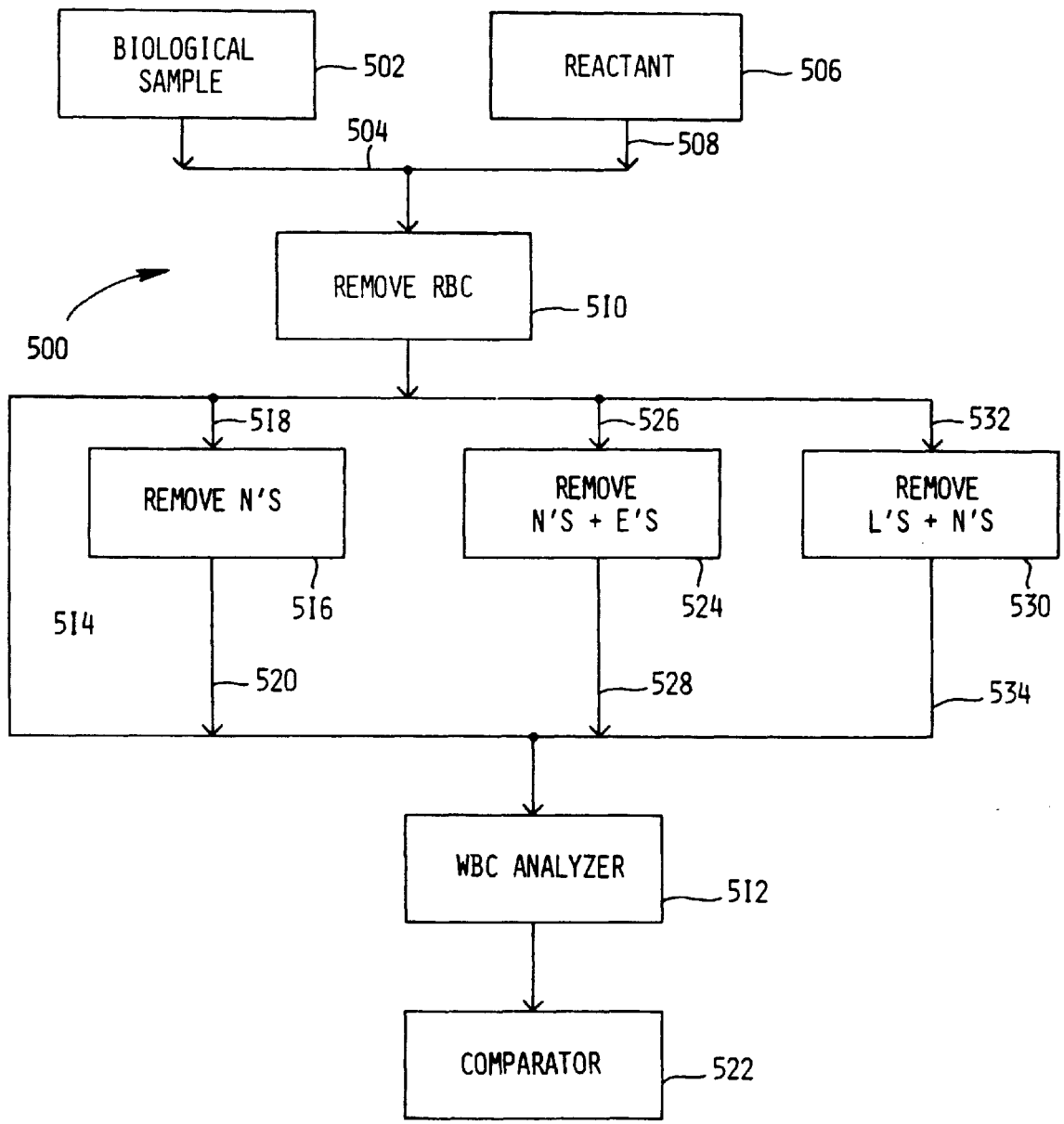
Figure 29A:
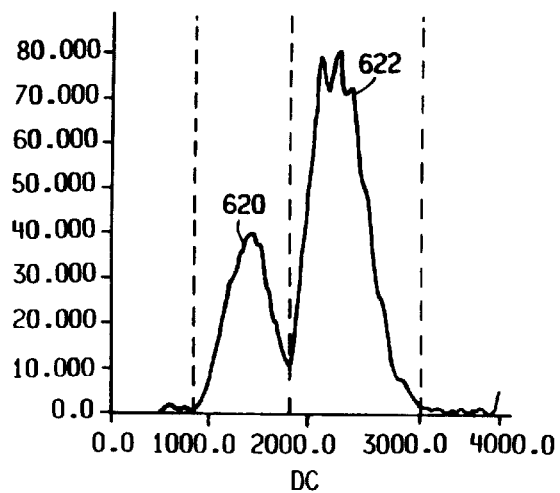
FIGS. 29A–D are scattergrams of one set of results utilizing a prototype analyzer system and a DC sensing parameter similar to that illustrated with respect to FIGS. 27 and 28.
Figure 29B:
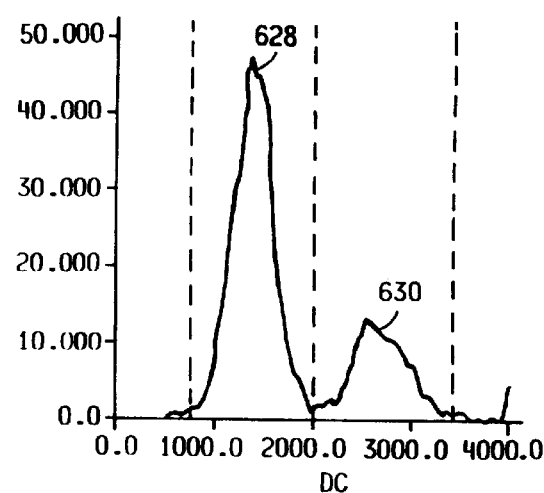
Figure 29C:
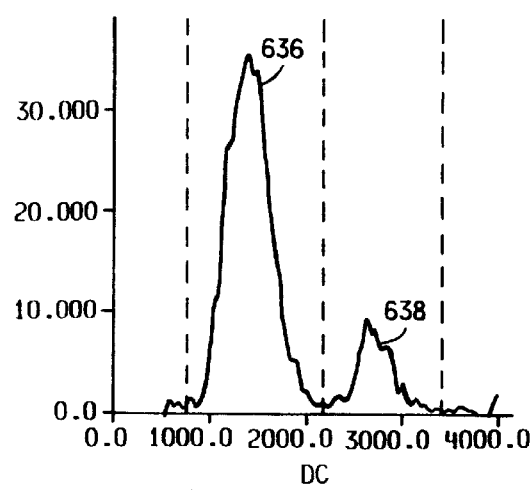
Figure 29D:
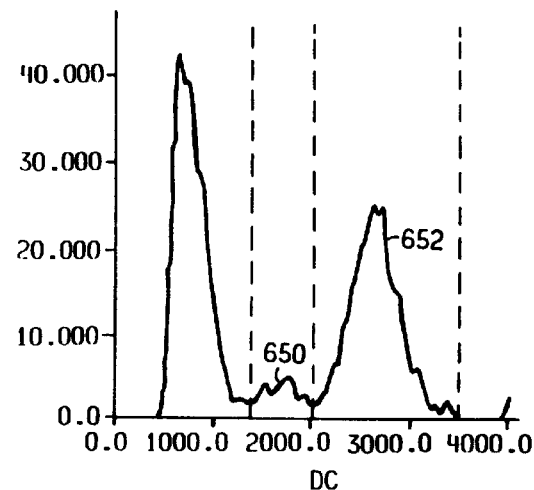
Figure 30A:
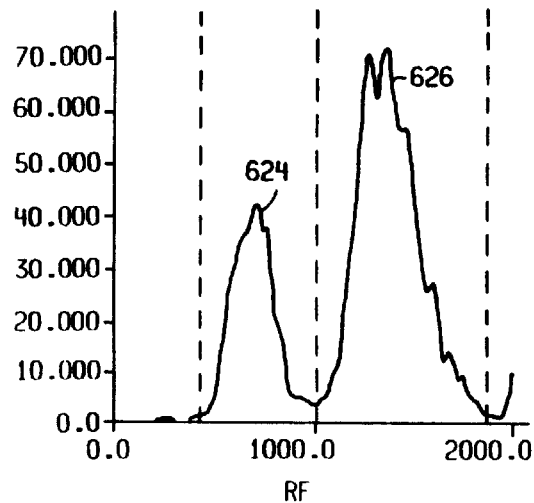
FIGS. 30A–D are scattergrams of the same results of FIGS. 29A–D utilizing an RF sensing parameter.
Figure 30B:
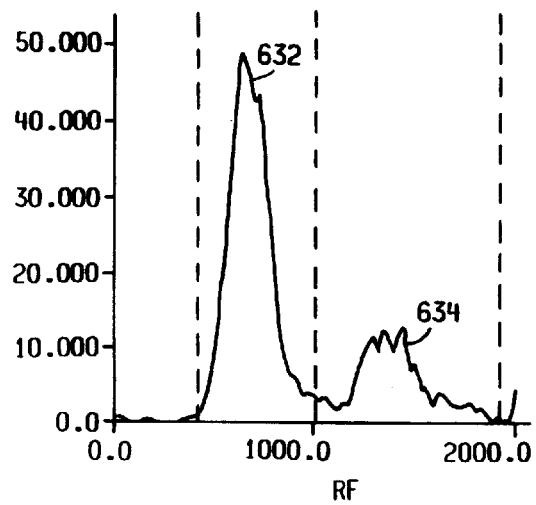
Figure 30C:
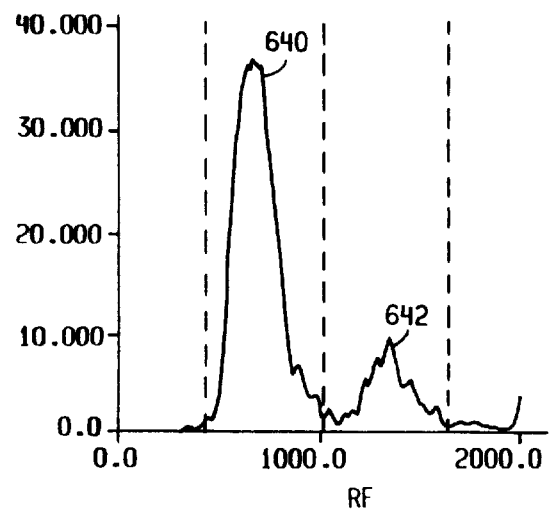
Figure 30D:
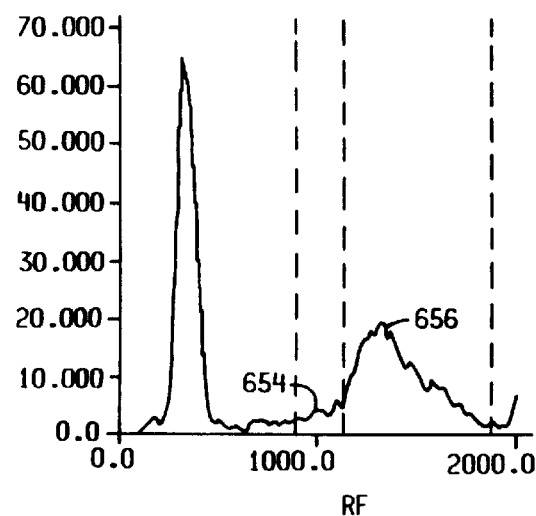
Figure 31A:
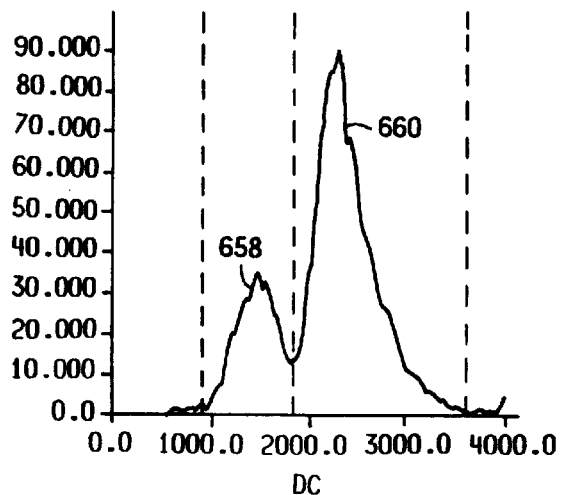
FIGS. 31A–D are scattergrams of a second set of results utilizing the prototype analyzer system and a DC sensing parameter similar to that illustrated with respect to FIGS. 27 and 28.
Figure 31B:
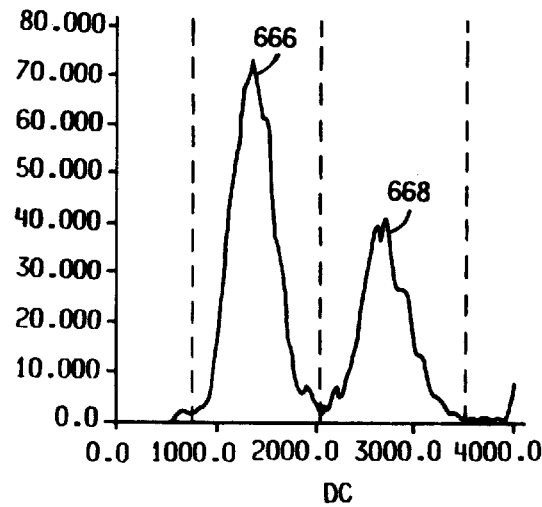
Figure 31C:
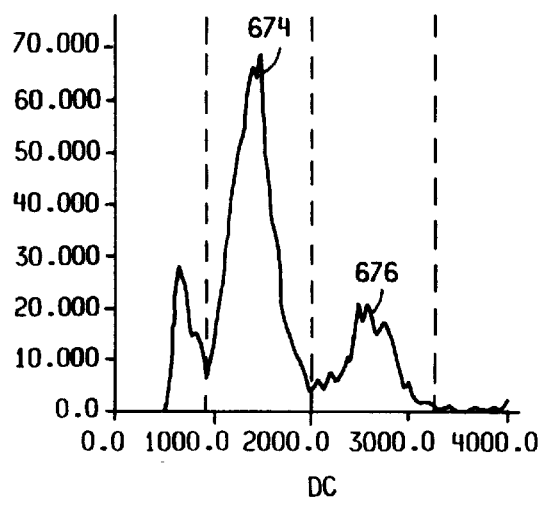
Figure 31D:
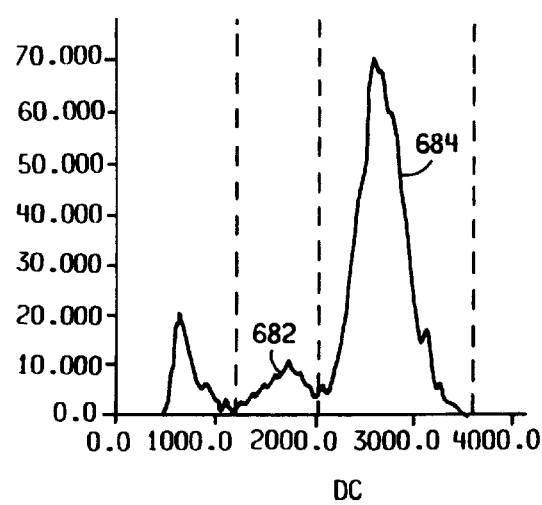
Figure 32A:
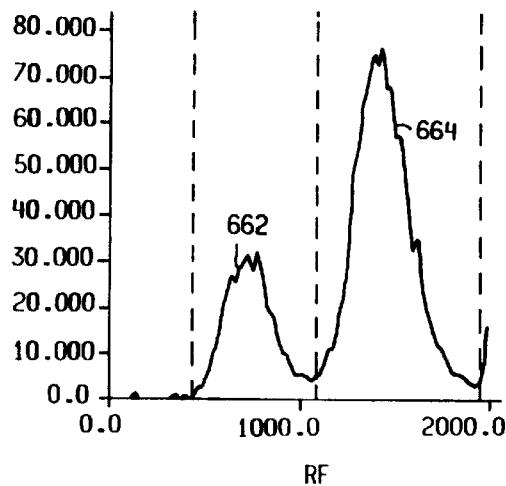
FIGS. 32A–D are scattergrams of the same results of FIGS. 31A–D utilizing a RF sensing parameter.
Figure 32B:
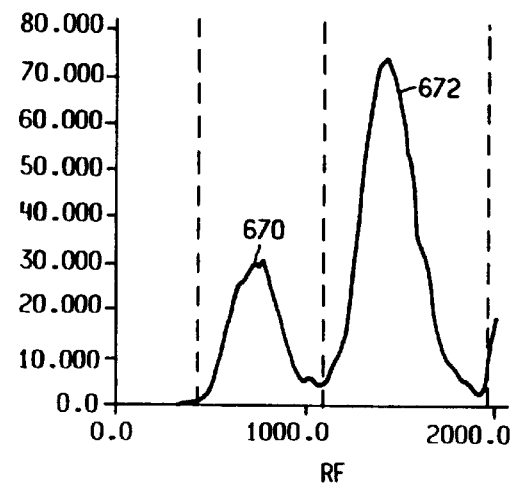
Figure 32C:
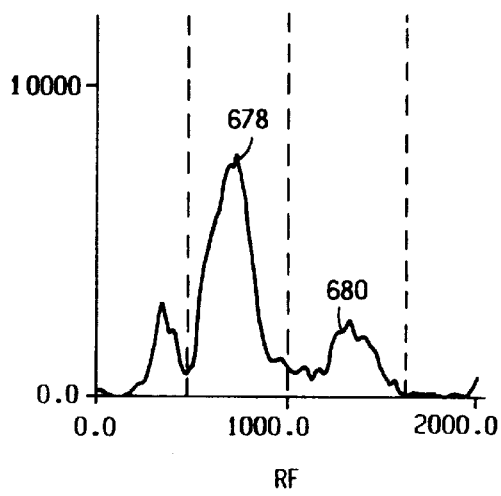
Figure 32D:
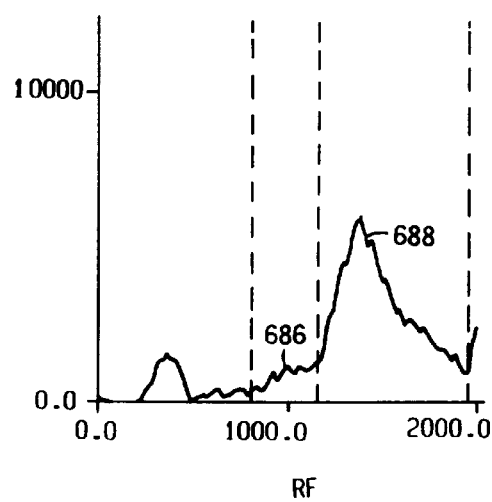

Referring to FIG. 27, a first embodiment of a method and apparatus for performing classification of cells such as a multipart differential is designated generally by the reference numeral 500. The instrument or analyzer 500 includes a biological sample 502, which contains at least a first set of viable biological cells (not illustrated), including at least two white blood cell populations, such as in or from a whole blood sample.

The cells of the biological sample 502 are to be involved in a biological reaction in a quantitative and/or qualitative determination or analysis. The biological sample 502 can include a buffer into which the cells are added.

The biological sample 502 is combined via a line 504 with at least one reactant 506 via a line 508. In the analyzer 500, the RBC's are removed from the mixture at an RBC removing station 510. As stated in the first parent application, the RBC's can be removed from the station 510 in a number of ways, such as enumerated with respect to the station 20.

A first portion of the mixture with the RBC's removed, then is fed to a WBC analyzer 512 via a line 514. This obtains a standard or control for the total or whole WBC populations of the biological sample 502. The analyzer 512 can be the same as the analyzer 86 or can be a light sensing analyzer, such as described in U.S. Ser. No. 025,442 filed Mar. 13, 1987 now abandoned and U.S. Ser. No. 129,954, filed Dec. 4, 1987, now abandoned in favor of continuation application U.S. Ser. No. 479,199, filed Feb. 13, 1990 now U.S. Pat. No. 5,125,737 entitled *MULTI-PART DIFFERENTIAL ANALYZING APPARATUS UTILIZING LIGHT SCATTER TECHNIQUES*, which are incorporated herein by reference. The single sensing parameter can be electronic, such as RF or DC or light, such as median angle light scatter (Scatter) or any other desired light parameter.

A second portion of the mixture is fed to a N removing station 516 via a line 518. The N's are removed by the addition of the appropriate magnetic microspheres with the N specific antibody bound thereto. In this example, the particular N specific antibody utilized is disclosed in Case 168,306, *MONOCLONAL ANTIBODY SPECIFIC TO NEUTROPHILS*, filed Dec. 8, 1986, now U.S. Ser. No. 938,864, which is incorporated herein by reference. A magnet or magnetic field is utilized, as before discussed, to remove the magnetically bound cells from the mixture. The remaining mixture with the N's removed then is fed via a line 520 to the analyzer 512. The analyzed results of this portion of the mixture then can be compared with the analyzed results of the first mixture portion in a comparator 522 to obtain the percentage of N's in the biological sample 502.

A third portion of the mixture is fed to a N and E removing station 524 via a line 526. The N's and E's are removed by the addition of appropriate magnetic microspheres with the N and E specific antibody bound thereto. One such exemplary N and E specific antibody is disclosed in U.S. Ser. No. 068,618, entitled *MONOCLONAL ANTIBODY SPECIFIC TO A COMMON DETERMINANT SITE OF NEUTROPHILS AND EOSINOPHILS*, filed Jun. 3, 1987, which is incorporated herein by reference. Separate N and E specific antibodies, bound to the same or separate magnetic microspheres, also can be utilized, where appropriate or as developed. The remaining mixture with the N's and E's removed then is fed via a line 528 to the analyzer 512. The analyzed results of this portion of the mixture then is compared to the results of the first and second mixture portions in the comparator 522 to obtain the percentage of E's and M's in the biological sample 502.

A fourth portion of the mixture is fed to a L and N removing station 530 via a line 532. The L's and N's are removed by the addition of the appropriate magnetic microspheres with the L and N specific antibody bound thereto. The N specific antibody can be either of the above referenced N specific antibodies, or other appropriate antibodies. The L specific antibody can be an L specific antibody as developed or a combination of the specific antibodies sold under the nomenclature T11 and 2H4 by Coulter Immunology Division of Coulter Corporation, which together bind all the L's. The remaining mixture with the L's and N's removed then is fed via a line 534 to the analyzer 512. The analyzed results of this portion of the mixture then can be compared to the results of the other mixture portions to obtain the percentage of B's and L's in the biological sample 502.

Thus, the analyzer 500 performs a single classification of cells, such as N's utilizing lines or channels 514 and 518, E's and/or N's and/or M's utilizing lines 514, 518 and 526 and a full five part WBC differential utilizing all four lines. One most important feature of the analyzer 500 is that the mixtures can be analyzed utilizing only a single analyzing parameter, such as one electronic parameter or one light parameter. Other combinations can be utilized, but in each case only a single sensed parameter or characteristic is necessary to perform the classification of the parent application.

FIG. 28 illustrates a specific analyzing instrument embodiment incorporating the method and apparatus of the analyzer 500 designated generally by the reference numeral 540. The instrument 540 includes an aspirator pumping mechanism 542 which is utilized to draw the biological sample of interest, for example the sample 502, into the instrument 540. The aspirator 542 is coupled via a line 544 to a sampling valve 546, which can be coupled to a sample probe 548. The biological sample 502 then is fed via a line 550 and a multipart valve 551 into the separate channels 514, 518, 526 and 532.

Describing first the channel 514, the sample portion is fed to a chamber 552. The chamber can be a mixing chamber into which the sample and reactant is fed to remove the RBC's. For example, utilizing lyse, the RBC's are lysed in the chamber 552 by adding the appropriate lyse thereto and preferably mixing therewith, then when the reaction is completed, a quench or fix is supplied to the chamber 552.

Specific details of an appropriate mixing apparatus, which can be utilized herein are disclosed in Ser. No. 025,337, filed Mar. 13, 1987, entitled *METHOD AND APPARATUS FOR RAPID MIXING OF SMALL VOLUMES FOR ENHANCING BIOLOGICAL REACTIONS*, which is incorporated herein by reference. By utilizing the mixer, the reactions are greatly enhanced in speed without significantly damaging the properties of interest of the cells, such as, can occur by raising the reaction temperature. Further, the reactions generally are completed in significantly less than a minute, generally on the order of fifteen seconds or less. This allows a rapid analysis of the automatic high volume analyzer instrument 540.

The quenched reactant mixture with the RBC's removed by the lyse then is fed via a line 554 to a multipart valve 556, or directly to a WBC analyzer 558 via a line 560. The analyzer 558 can be of many physical types in accordance with the counting and sizing techniques described by Wallace H. Coulter in U.S. Pat. No. 2,656,508 utilizing light or electronic sensing as embodied in the numerous commercial blood cell counters of the assignee, Coulter Electronics, Inc.

The analyzer 558, in general, includes a flow sensor or sensing chamber 562. The chamber 562 includes a transducer 564 which has an aperture therethrough. The chamber 562 can include a first portion 566 which has a first electrode 568 in contact with the fluid therein. The chamber portion 566 and the electrode 568 can communicate through the sensing aperture with a second chamber portion 570 having a second electrode 572 therein.

The electrodes 568 and 572 are coupled via reactive leads to an RF/DC source and sensing circuit 574. The circuit 574 couples either or both a DC, or low frequency current or signal, and a high frequency signal between the electrodes 568 and 572.

The low frequency signal is utilized to sense the amplitude of a signal pulse caused by a cell passing through the sensing aperture. The high frequency signal can be utilized in the same manner as a single parameter or with the low frequency signal to obtain the electrical opacity of the same cell passing through the sensing aperture.

The measuring of the electrical opacity of cells was described by Wallace H. Coulter and Walter R. Hogg in U.S. Pat. No. 3,502,974 and several patents and publications of the assignee, Coulter Electronics, Inc., since that patent. One specific circuit which can be utilized herein is disclosed in Case 168,008, entitled *PARTICLE ANALYZER FOR MEASURING THE RESISTANCE AND REACTANCE OF A PARTICLE*, filed Oct. 21, 1986 as U.S. Ser. No. 921,654, now U.S. Pat. No. 4,791,355, which is incorporated herein by reference.

The signals generated by the circuit 574 from the sensed cells are coupled via a DC signal lead 576 and/or an RF signal lead 578 to a comparator 580 (like the comparator 26). The comparator 580 can hold the signal generated from the first portion, i.e., those without the WBC population or population subset subtracted, for a comparison with the results from the subsequent portions described hereinafter. The analyzer 558 can include a sheath flow to focus the cells in the sensor 562, in the well known manner. The sheath flow can be provided by a fluidic system 582, coupled to the sensor in a known manner.

The analyzer 558 has been illustrated with both RF and DC analyzing circuitry for example purposes only. In obtaining the multipart WBC population or subset population characterization of the parent application, only a single sensing parameter, electronic or optical, need be utilized. In the case of electronic sensing, the parameter can be either DC or RF. Utilizing optical sensing, not illustrated, again only a single parameter such as median angle light scatter need be utilized. This one dimension sensing can simplify the instrument 540, as well as decrease the cost thereof.

A second portion of the sample mixture is fed through the valve 551 via the line 518 to the N removing station 516. The station 516 includes a mixer or chamber 584. The mixing chamber 584 has the second mixture portion fed thereto via the line 518. The mixer 584 includes all of the various options above described and, for example, includes a lyse input line for the RBC lyse.

When the lyse is utilized, after mixing as illustrated functionally at 586, then the quench is added via a quench line. At the same time or sequentially, the N's are being removed by the addition of the appropriate magnetic microspheres with the N specific antibody bound thereto from a source of microspheres 588 fed to the chamber 584 via a line 590. A magnet 592 or magnetic field is then utilized to remove the magnetically bound cells on the magnetic microspheres. The mixed and quenched mixture than is fed via the line 520 through the valve 556 and the line 560 to the WBC analyzer 558 to be analyzed as before described. The analyzed mixture with the N's removed then is compared in the comparator 580 to determine the percentage of N's in the sample 502.

A third mixture portion of the sample 502 is fed via the line 550 and the valve 551 via the line 526 to the N and E removing station 524. The station 524 includes a mixing chamber 594. In the third portion, the RBC's are removed by the RBC lyse fed into the chamber 594. The lyse is mixed with the sample portion and then a quench is added via a quench line. The N's and E's are removed by magnetic microspheres having the N and E specific antibody or antibodies bound thereto from a microsphere source 596 fed into the chamber 594 via a line 598. The microspheres are mixed, functionally at 600, and then the bound N and E microspheres are magnetically removed, functionally at 602. The N and E removed mixture then is fed via the line 528 to the valve 556 and via the line 560 to the analyzer 558 to also obtain the above mentioned results.

The instrument can be utilized with the first two channels 514 and 518 to determine the N percentage or with the first three channels 514, 518 and 526 to obtain the N's and E's percentages and/or the M's percentage, as desired. To obtain further WBC population or subset population characterizations, a fourth portion of the sample mixture 502 is fed via the line 550 and the valve 551 via the line 532 to the L and N removing station 530. Again, the RBC's are removed such as by lysing in a chamber 604, and the L's and N's are removed by binding the L's and N's to magnetic microspheres having the L and N specific antibody or antibodies bound thereto from a source 606 fed into the mixing chamber 604 via a line 608. The microspheres are mixed, functionally at 610, and then the magnetically bound L and N microspheres are magnetically removed, functionally at 612.

The L and N removed mixture then is fed via the line 534 to the valve 556 and via the line 560 to the analyzer 558 to obtain the above-mentioned results. Utilizing combinations of the results from the other channels, the percentage of L's and/or B's then can be obtained such as to perform a full five part WBC differential to obtain the percentage of N's, E's, M's, L's and B's. The mixers include appropriate rinse lines and waste lines and the instrument 540 can include a probe rinse 614 to cleanse the instrument 540 prior to aspirating the next sample or sample portion for analyzing. Further, the sample 502 can be diluted from a source 616 via a line 618 if desired.

Only one specific hardware embodiment incorporating the method and apparatus of the analyzer 500 has been illustrated, but like the embodiments in the parent application, the analyzing instrument 540 can be implemented in numerous configurations. For example, the analyzer 540 could include a single channel, such as the channel 518 and the portions each can be run sequentially through the station 516 with the appropriate WBC population or populations removed from each portion, as previously described with respect to the separate channels.

Referring now to FIGS. 29A–D and FIGS. 30A–D, two sets of one dimensional scattergram multipart characterization results are illustrated, obtained from a whole blood sample, utilizing a prototype analyzing method similar to the analyzer instrument 540. The biological sample in each case was a 28 microliter sample of whole blood, which was combined with 122 microliters of buffer solution for the sample portion utilized in the first channel 514. The sample portion was lysed with 300 microliters of the RBC preferential lyse above referenced in the chamber 552. The sample portion was lysed for 4 seconds and then quenched with 120 microliters of quench before being fed to the analyzer 558 via the line 554, the valve 556 and the line 560. The results of analyzing utilizing a one dimensional electronic sensing parameter are illustrated in FIGS. 29 and 30. DC was utilized to obtain the data in FIGS. 29A–29D and RF was utilized to obtain the data (for comparison) in FIGS. 30A–30D, utilizing the same sample portion and measured at the same time in the analyzer 558. This results in two clearly identifiable data peaks 620 and 622 in FIG. 29A and peaks 624 and 626 in FIG. 30A. Peaks 620 and 624 are indicative of the percentage of L's and B's in the sample. Peaks 622 and 626 are indicative of the percentage of N's, E's and M's. Clearly, in one dimension, without further manipulation, the individual percentages are masked by the competing cells in the same data peak. As described in the above referenced parent application, this is not a problem, at least for some cells when greater than one parameter is utilized to differentiate the data.

In the second channel 518, a second whole blood sample portion of 28 microliters is combined with 40 microliters of magnetic microspheres with the N specific antibody bound thereto and combined with 82 microliters of buffer solution in the chamber 584. The sample portion was mixed for 60 seconds, lysed and quenched in the same manner as in the channel 514 and then placed in the magnetic field 592 for 30 seconds before the mixture with the N's removed is fed to the analyzer 558 via the line 520, the valve 556 and the line 560. This results in two data peaks 628 and 630 in FIG. 29B and two data peaks 632 and 634 in FIG. 30B. Peaks 628 and 632 remain the same as the peaks 620 and 624 although their percentage of the sample mixture portion now is greater, while the peaks 630 and 634 are indicative of the percentage of the E's and M's with the N's removed. The data peaks 630 and 634 can then be compared with the respective data peaks 622 and 626 to determine the percentage of N's in the whole blood sample.

Next, or in any order including substantially simultaneously, a third 28 microliter sample portion is fed to the third channel 526 and mixed with 20 microliters of magnetic microspheres with the E and N specific antibody or antibodies bound thereto and combined with 102 microliters of buffer solution in the chamber 594. The sample portion was mixed for 30 seconds, lysed and quenched in the same manner as in the channel 514 and then placed in the magnetic field 602 for 30 seconds before the mixture with the N's and E's removed is fed to the analyzer 558 via the line 528, the valve 556 and the line 560. This results again in two data peaks 636 and 638 in FIG. 29C and data peaks 640 and 642 in FIG. 30C. Peaks 636 and 640 again are the same contribution as the peaks 620 and 624, while the data peaks 638 and 642 are indicative of the percentage of the M's in the whole blood sample as compared to the data peaks 622 and 626. The data peaks 638 and 642 then can be compared to the data peaks 630 and 634 also to determine the percentage of E's in the whole blood sample.

A fourth 28 microliter sample portion is fed to the fourth channel 532 and mixed with 70 microliters of magnetic microspheres with a CD2 specific antibody bound thereto and 50 microliters of magnetic microspheres with a CD45R specific antibody bound thereto in the chamber 604. The sample portion was mixed for 2 minutes and then placed in the magnetic field 612 for 30 seconds and then the remaining mixture is removed to a holding chamber 644 via a line 646. The holding chamber 644 currently appears to be a necessary operation, because the specific antibodies utilized as above referenced under the nomenclature T11 and 2H4 and the N specific antibody, appear to interfere with one another when utilized simultaneously. It is not known whether this is due to the specific antibodies or to the nature of the cells themselves. Once the mixture with the T11 and 2H4 bound cells removed is fed into the holding chamber 644, the chamber 604 then is rinsed with the magnetic field removed to remove the magnetic microspheres having the CD2 and CD45R cell clusters bound thereto.

The N bound magnetic microspheres then are isolated in the chamber 604, which can be provided by another source, other than the source 606 (not illustrated). The isolation is accomplished by holding the magnetic microspheres with 40 microliters of the N specific antibody bound thereto in the magnetic field 612 and removing the buffer solution to waste. Alternately, the mixture can be adjusted so that the buffer solution is utilized as part of the mixture or a concentrated volume of magnetic microspheres can be utilized and the solution need not be utilized. The sample portion then is returned to the chamber 604 from the chamber 644 via a line 648 and mixed with the magnetic microspheres with the N specific antibody bound thereto, lysed and quenched as in the channel 514 and then again placed in the magnetic field 612 for 30 seconds before the mixture with all the L's and N's removed is fed to the analyzer 558 via the line 534, the valve 556 and the line 560. This results in two data peaks 650 and 652 in FIG. 29D and two data peaks 654 and 656 in FIG. 30D. Peaks 650 and 654 represent only the B's, since all the L's have been removed. Since the L's are about 30 percent of a normal whole blood sample, this enhances the B's which originally are about 1 percent of the sample to a very significant data peak (i.e., amount of data). The B's are further enhanced since the N's also were removed from the peaks 652 and 656 and they originally are about 60 percent of the sample. Hence, the B's now represent about 10 percent of the remaining B, M and E cells.

The actual percentage calculations are performed as follows, with the data peak numbers calculated by dividing the data peak (number of cells counted in the peak) by the total data from both peaks (utilizing FIGS. 29A–29D for example purposes):

1) M %–determined from channel 526:

[(Pk1 (620)) (Pk1 (636))] xx Pk2 (638)=$M$ %

2) M+E %–determined from channel 518:

[(Pk1 (620)) (Pk1 (628))] xx Pk2 (630)=$M+E$ %

3) E %=M+E %–M %
4) N %=(Pk2 (622))–M+E %
5) B %–determined from channel 532:

[(Pk2 (630)) (Pk2 652))] xx (Pk1 (650))=$B^1$ %

$B^1$ % xx [(P1 (620)) (Pk1 (628))] =$B$ %

6) L %=(Pk1 (620))–B %

For the data illustrated in FIGS. 29 and 30, the calculations from the RF and DC data are set forth in Table II.

TABLE II

| Channel | DC | | RF | |
|---|---|---|---|---|
| | Pk1 | Pk2 | Pk1 | Pk2 |
| 514 | 28.1 | 71.9 | 30.3 | 69.7 |
| 518 | 74.4 | 25.6 | 74.1 | 25.9 |
| 526 | 83.8 | 16.2 | 83.4 | 16.6 |
| 532 | 10.9 | 90.1 | 10.0 | 90.0 |

A full five part differential in percentage of the N's, L's, M's, E's and B's also was calculated from the DC and RF data peaks and compared to a light sensing instrument for verification purposes, such as described in U.S. Ser. No. 025,442.

TABLE III

5 PART DIFFERENTIAL

| LIGHT | DC | RF |
|---|---|---|
| N 61.58 | N 62.2 | N 59.1 |
| L 28.50 | L 26.9 | L 29.1 |
| M 6.27 | M 5.4 | M 6.0 |
| E 3.10 | E 4.3 | E 4.6 |
| B 0.56 | B 1.2 | B 1.2 |

Referring now to FIGS. 31A–D and FIGS. 32A–D, a second two sets of one dimensional scattergram multipart characterization results are illustrated, obtained from a second whole blood sample, again utilizing a prototype analyzing method similar to the analyzer instrument 540. The biological sample in each case again was a 28 microliter sample of whole blood, prepared for each channel as described with respect to FIGS. 29 and 31. The sample portion was lysed in the first channel 514 in the chamber 552 and then quenched before being fed to the analyzer 558. The results of analyzing utilizing a one dimensional electronic sensing parameter are illustrated in FIGS. 31 and 32. DC was utilized to obtain the data in FIGS. 31A–31D and RF was utilized to obtain the data (for comparison) in FIGS. 32A–32D, utilizing the same sample portion and measuring at the same time in the analyzer 558. This results in two clearly identifiable data peaks 658 and 660 in FIG. 31A and peaks 662 and 664 in FIG. 32A. Peaks 658 and 662 are indicative of the percentage of L's and B's in the sample. Peaks 660 and 664 are indicative of the percentage of N's, E's and M's. Again, in one dimension, without further manipulation, the individual percentages are masked by the competing cells in the same data peak.

In the second channel 518, a second whole blood sample portion is combined with the magnetic microspheres with the N specific antibody bound thereto in the chamber 584, mixed, lysed and quenched and then placed in the magnetic field 592 before the mixture with the N's removed is fed to the analyzer 558. This results in two data peaks 666 and 668 in FIG. 31B and two data peaks 670 and 672 in FIG. 32B. Peaks 666 and 670 remain the same as the peaks 568 and 662 although their percentage of the sample mixture portion now is greater, while the peaks 668 and 672 are indicative of the percentage of the E's and M's with the N's removed. The data peaks 668 and 672 can then be compared with the respective data peaks 660 and 664 to determine the percentage of N's in the whole blood sample.

Next, or in any order including substantially simultaneously, a third sample portion is fed to the third channel 526 and mixed with the magnetic microspheres with the E and N specific antibody or antibodies bound thereto in the chamber 594, mixed, lysed and quenched and then placed in the magnetic field 602 before the mixture with the N's and E's removed is fed to the analyzer 558. This results again in two data peaks 674 and 676 in FIG. 31C and data peaks 678 and 680 in FIG. 32C. Peaks 674 and 678 again are the same contribution as the peaks 658 and 662, while the data peaks 676 and 680 are indicative of the percentage of the M's in the whole blood sample as compared to the data peaks 660 and 664. The data peaks 676 and 680 then can be compared to the data peaks 668 and 672 also to determine the percentage of E's in the whole blood sample.

A fourth sample portion is fed to the fourth channel 532 and mixed with the magnetic microspheres with a CD2 specific antibody bound thereto and the magnetic microspheres with a CD45R specific antibody bound thereto in the chamber 604, mixed, then placed in the magnetic field 612 and then the remaining mixture is removed to the holding chamber 644.

The N bound magnetic microspheres then are isolated in the chamber 604 by holding the magnetic microspheres with the N specific antibody bound thereto in the magnetic field 612 and removing the buffer solution. The sample portion then is returned to the chamber 604 after it is rinsed from the chamber 644 via a line 648 and mixed with the magnetic microspheres with the N specific antibody bound thereto, lysed and quenched and then again placed in the magnetic field 612 before the mixture with all the L's and N's removed is fed to the analyzer 558. This results in two data peaks 682 and 684 in FIG. 31D and two data peaks 686 and 688 in FIG. 32D. Peaks 682 and 686 represent only the B's, since all the L's have been removed to enhance the B's to a very significant data peak (i.e., amount of data). The B's are further enhanced since the N's also were removed from the peaks 684 and 688 and hence from the remaining sample portion.

The actual percentage calculations are performed as before as set forth hereinafter, with the data peak numbers calculated by dividing the data peak (number of cells counted in the peak) by the total data from both peaks (utilizing FIGS. 31A–31D for example purposes):

1) M %–determined from channel 526:

[(Pk1 (658)) (Pk1 (674))] xx Pk2 (676)=$M$ %

2) M+E %–determined from channel 518:

[(Pk1 (658)) (Pk1 (666))] xx Pk2 (66)=$M+E$ %

3) E %=M+E %–M %
4) N %=(Pk2 (660))–M+E %
5) B %–determined from channel 532:

[(Pk2 (668)) (Pk2 (684))] xx (Pk1 (682)=$B^1$ %

$B^1$ % xx [(Pk1 (658)) (Pk1 (666))] =$B$ %

6) L %=(Pk1 (658))–B %

For the data illustrated in FIGS. 31 and 32, the calculations from the RF and DC data are set forth in Table IV.

TABLE IV

| Channel | DC | | RF | |
|---|---|---|---|---|
| | Pk1 | Pk2 | Pk1 | Pk2 |
| 514 | 24.0 | 76.0 | 26.0 | 74.0 |
| 518 | 63.3 | 36.7 | 62.6 | 37.4 |
| 526 | 76.0 | 24.0 | 75.2 | 24.8 |
| 532 | 10.6 | 89.4 | 9.7 | 90.3 |

A full five part differential in percentage of the N's, L's, M's, E's and B's again was calculated from the DC and RF data peaks and again compared to a light sensing instrument for verification purposes, such as described in U.S. Ser. No. 025,442.

TABLE V

| 5 PART DIFFERENTIAL | | |
|---|---|---|
| LIGHT | DC | RF |
| N 60.37 | N 62.1 | N 58.5 |
| L 24.70 | L 22.4 | L 24.3 |
| M 8.62 | M 7.6 | M 8.6 |
| E 5.12 | E 6.3 | E 6.9 |
| B 1.18 | B 1.6 | B 1.7 |

The calculations are set forth below utilizing the DC data peaks:

1) $M\%$ = $\frac{24.0}{76.0} \times 24.0 = 7.6$

2) $M + E\%$ = $\frac{24.0}{63.3} \times 36.7 = 13.9$

3) $E\%$ = $(13.9) - (7.6) = 6.3$

4) $N\%$ = $(76.0) - (13.9) = 62.1$

5) $B\%$ = $\frac{36.7}{89.4} \times 10.6 = 4.4$ $4.4 \times \frac{24.0}{63.3} = 1.6$

6) $L\%$ = $24.0 - 1.6 = 22.4$

The data peaks in FIGS. 29–32 were depicted utilizing a single electronic sensing parameter, either DC or RF. Opacity was not illustrated, but also could be utilized if desired, since it is RF/DC as previously described. A single light sensing parameter also can be utilized, for example, median angle light scatter (Scatter), as illustrated in FIGS. 33–36.

Figure 33:
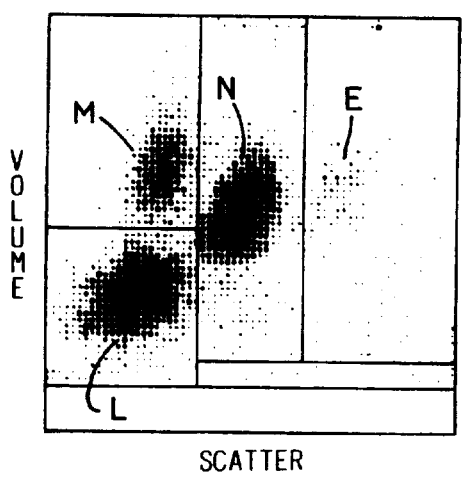
Figure 34:
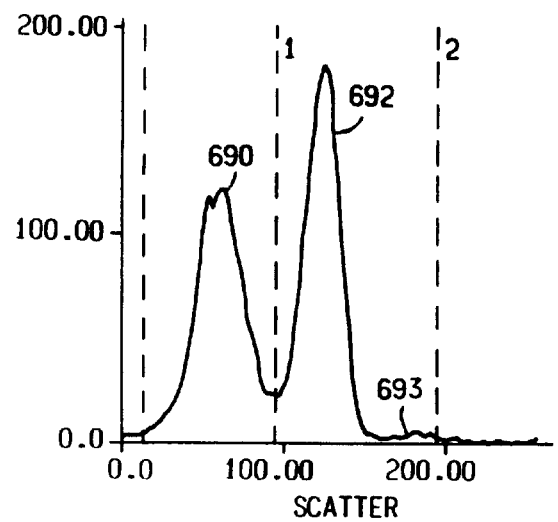
Figure 35:
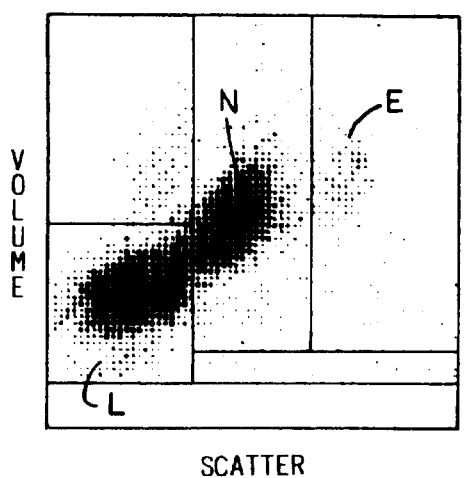
Figure 36:
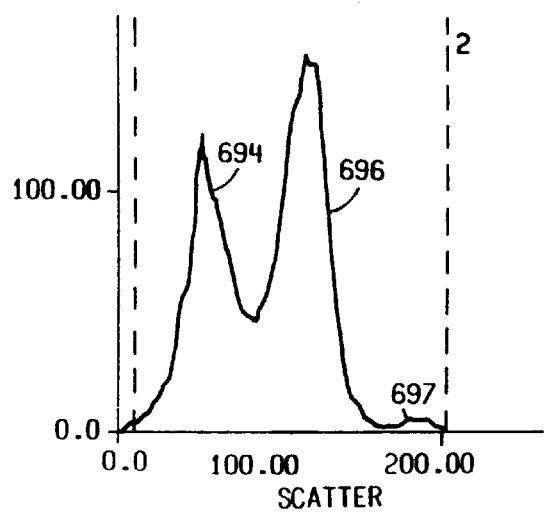

Referring to FIG. 33, the M's, L's, N's and E's groups of cells are clearly separated by utilizing two parameters, Scatter and electrical volume. The B's are obscured in this data pattern. However, in one dimension, the same scatter data illustrated in FIG. 34 now results in the M's obscuring the L's or vice versa as seen in data peak 690. The N's and E's are illustrated in data peak 692 and the E's in data peak 693, representing the same data as in FIG. 33.

One method of solving the problem of the obscured data in the data peak 690 is to remove the M's. Currently this would be accomplished in an offline or prepreparation mode, since the M's are removed slowly when utilizing a CD14 specific antibody, such as M02 sold by Coulter Immunology Division of Coulter Corporation. For example, 400 microliters of a whole blood sample are combined with 200 microliters of a 2½ percent solution of magnetic microspheres with the CD14 specific antibody bound thereto. The magnetic microspheres are first isolated by removing the fluid therefrom while holding the microspheres in a magnetic field. The sample then is added and the mixture is gently mixed, such as by rocking for about 30 minutes and then placed in a magnetic field for about 5 minutes after which the preprepared mixture, with the M's removed is analyzed in the instrument 540 as previously described. The data is illustrated again in two dimensions for comparison purposes in FIG. 35, where it clearly can be seen that the M's have been depleted by comparison with FIG. 33, enhancing the remaining WBC population data.

The one dimensional scatter data is illustrated in FIG. 36, again resulting in two data peaks 694 and 696. The peak 694 is the data peak 690 with the M's removed, leaving only the L's. The peak 696 is the same as the data peak 692, and peak 697 is the same as peak 693, both peaks 696 and 697 are enhanced by the removal of the M's from the sample portion. Although not specifically illustrated, the sample mixture with the M's removed as illustrated in peak 694, now can be further depleted to perform L subset analyses, as will be further described hereinafter.

Although the analyzer 500 is illustrated for explanation purposes utilizing four separate channels, this only enhances the speed of the classification method of the parent application. The parent application also can be practiced utilizing a single channel, with the different portions of the biological sample 502 being processed sequentially.

Figure 37:
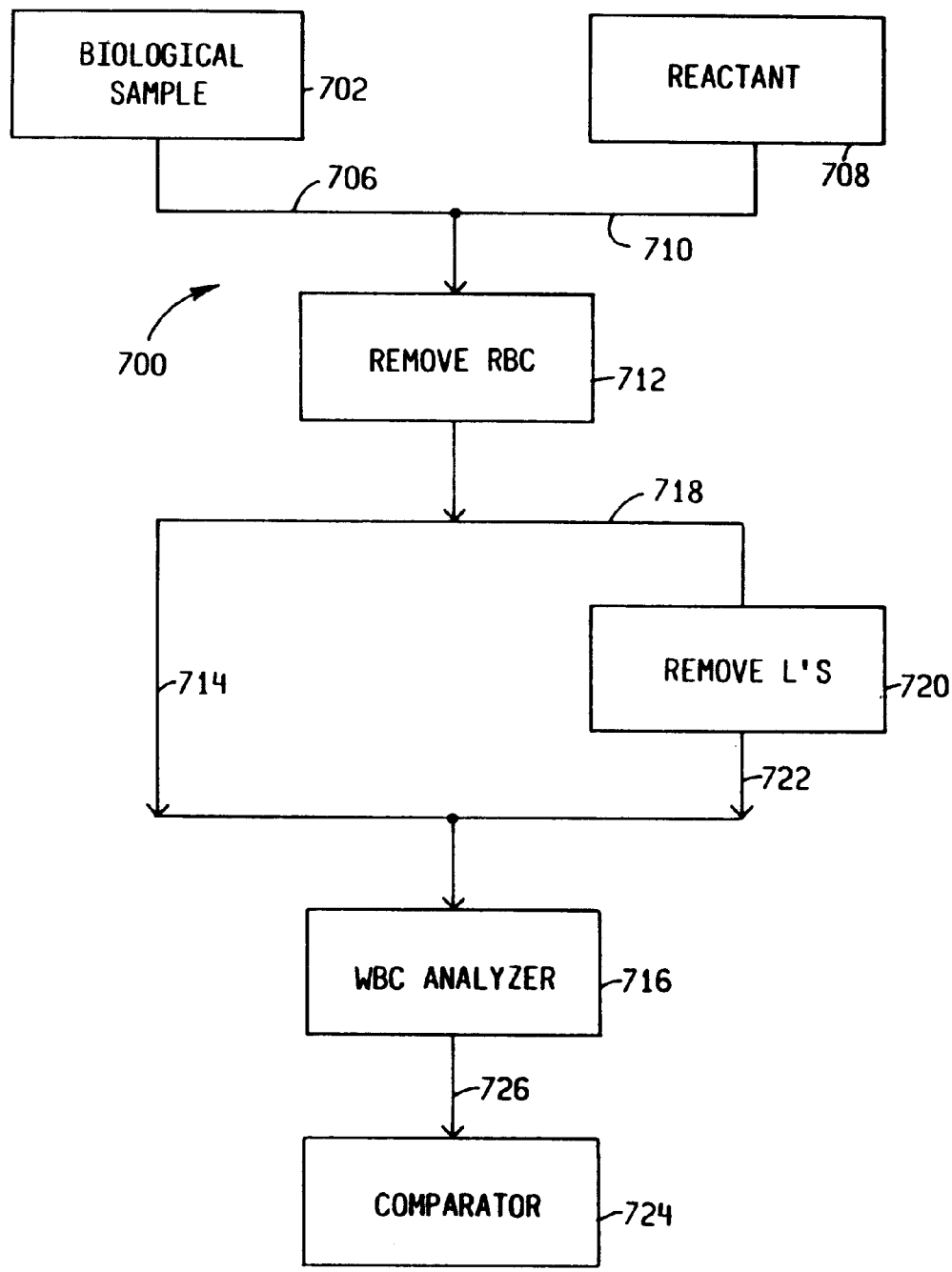
Figure 38A:
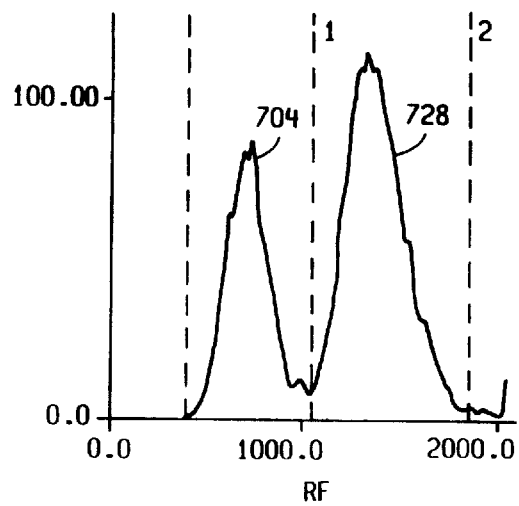
FIGS. 38A–E are scattergrams of one set of results obtained utilizing a prototype analyzer system and an RF sensing parameter similar to that illustrated with respect to FIGS. 27 and 37.
Figure 38B:
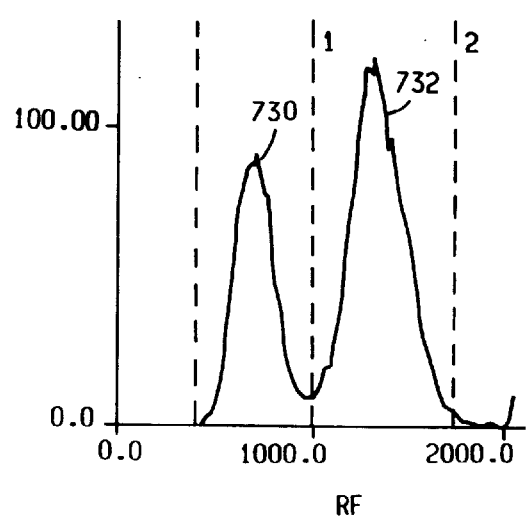
Figure 38C:
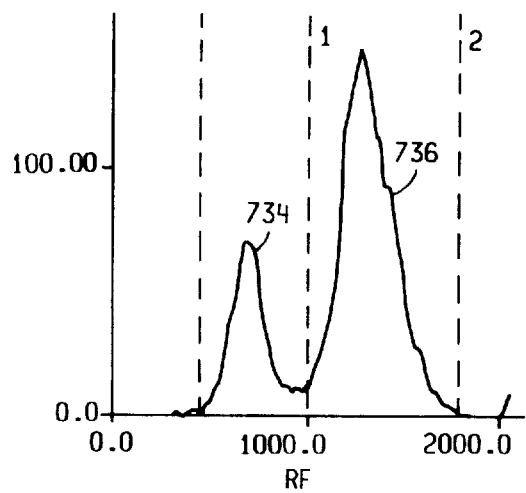
Figure 38D:
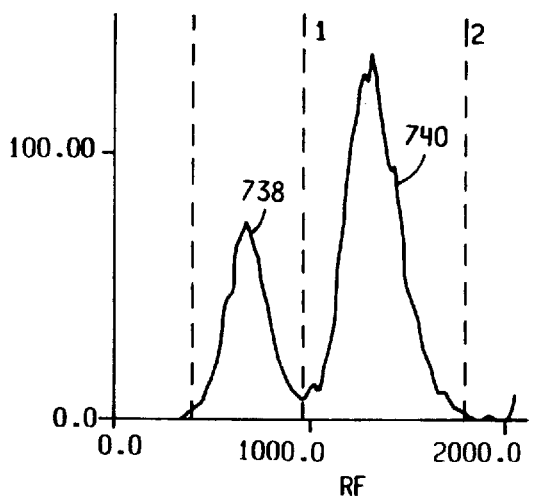
Figure 38E:
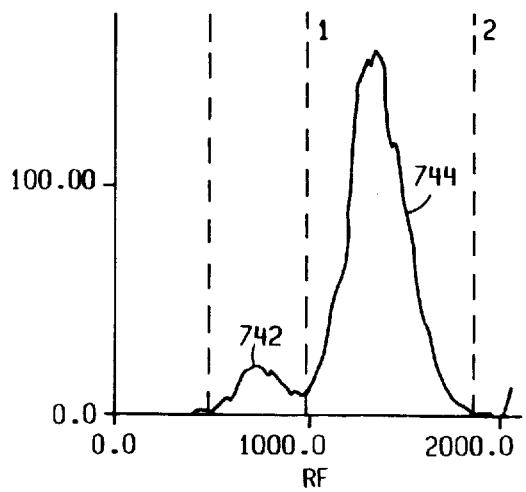

FIG. 37 illustrates an analyzer embodiment for a method and apparatus of enhancing small or obscure populations for classification thereof designated generally by the reference numeral 700. This method and apparatus can be utilized to determine such small populations as the B's or subsets of the L's. The analyzer 700 includes a biological sample 702, which contains at least a first set of viable biological cells (not illustrated), such as in or from a whole blood sample. If the classification is to be of B cells, then the sample 702 will include at least the B cell population and at least one other WBC population, such as the L cells. Generally the sample 702 would at least include all of the WBC populations, however, as previously described, various populations or subsets thereof can be eliminated offline or in a pre-preparation step. If the classification is to be of a WBC population subset, then the sample 702 will include at least one WBC population having at least one definable subset.

Describing first the classification of B cells, the B cells are a very small population of the total WBC populations, generally on the order of about less than one percent. Clearly, eliminating the WBC populations which obscure the B cells, will enhance the analysis and classification of the B's, because the B's then become a much greater and significant part of the remaining WBC population, as the other WBC populations are eliminated. Clearly, also, this enhancement will be true for all small or obscured cell populations of interest.

In analyzing the B cell populations utilizing a single measuring dimension or parameter, for example RF as illustrated in FIG. 38 to be described hereinafter, the B's are obscured by the L's in a single peak 704. The L's are around thirty (30) percent of the total WBC population and hence the B's still are only about three (3) percent even of only the L's and B's together. Therefore, to more definitely analyze and classify the B's, the L's are totally or substantially eliminated from the sample.

The sample 702 is combined via a line 706 with at least one reactant 708 via a line 710. The RBC's are removed in an RBC removal station 712 by one of the methods previously described. Once the RBC's are removed, a first portion of the resulting mixture is fed via a line 714 to a WBC analyzer 716. The WBC analyzer can be the same as those previously described, or minor variations thereof. The single sensing parameter can be electronic, such as RF or DC or light, such as Scatter or any other desired light parameter.

A second portion of the mixture is fed via a line 718 to a L removal station 720, wherein the L cells are bound to magnetic microspheres which include an L specific monoclonal antibody or antibodies bound thereto. The remainder of the mixture with at least the B cells remaining is fed via a line 722 to the WBC analyzer 716. The results of the two analyzed portions are fed to a comparator 724 via a line 726, where the two analyzed results are compared to determine the percentage of B's in the sample 702. The B's by this method have been made to change from about one to three percent of the sample mixture to substantially one hundred percent in the first data peak 704, providing definitive analysis and characterization. In a like manner, when the CD or other WBC population group chosen is small, all or some of the rest of the L's can be removed enhancing the analyzation of the remaining CD group of interest.

Next, describing the analysis and classification of one or more WBC population subsets, for example, the CD2, CD4 or CD8 WBC population subsets. The sample 702 again will include at least a first set of viable biological cells (not illustrated), such as in or from a whole blood sample. The sample 702 will include at least the WBC population subset of interest and at least one other obscuring WBC population or population subset and generally will include all the WBC populations.

The sample 702 again is fed to the RBC removal station 712 and then a first portion is fed to the WBC analyzer 716 via the line 714. A second portion will be utilized to determine the CD2 group, for example, and thus the second portion will be mixed with magnetic microspheres which include a CD2 specific monoclonal antibody bound thereto, such as T11 sold by Coulter Immunology Division of Coulter Corporation. The remainder of the mixture, with the CD2 cells now removed, will be fed via the line 722 to the WBC analyzer 716. The two analyzed results then are compared in the comparator 724 to provide the desired characterization of the CD2 group of cells.

The operation of the analyzer 700 can be performed on the instrument 540, utilizing the respective channels as desired or on a further multichannel instrument or again on a single channel instrument in a sequential fashion.

Referring now to FIGS. 38A–38E, the CD4, CD8 and CD2 subsets were determined as depicted in the one dimensional scattergram characterization results illustrated, utilizing a prototype analyzing method similar to the analyzer instrument 540. The biological sample in each case was a 28 microliter sample of whole blood. The sample was combined with 122 microliters of buffer solution for a control sample utilized in the channel 714 (which can be the channel 514 of the instrument 540). The results of a one dimensional electronic sensing parameter, here RF, was utilized to obtain the data for FIGS. 38A–E. The sample portion was lysed for 4 seconds with 300 microliters of the RBC preferential lyse above referenced (such as in the chamber 552) and then quenched with 120 microliters of quench before being fed to the analyzer 716 (such as the analyzer 558). This results in two clearly identifiable data peaks 704 and 728 in FIG. 38A. Peak 704 includes the B's and L's and all subsets thereof as a single peak. The B's are a small enough percentage so as to not effect the analyzation of the desired L subset, however, the value of the B's could be subtracted if desired.

A second control was utilized by combining a second whole blood sample portion of 28 microliters with 50 microliters of magnetic microspheres without any L or L subset specific antibody bound thereto and 72 microliters of buffer solution. The sample portion was lysed and quenched as before and then fed to the analyzer 716. This results in two data peaks 730 and 732 in FIG. 38B. The data peaks 730 and 732 are substantially identical to the peaks 704 and 728, hence the inclusion of the microspheres did not appear to have any deleterious effects on the analysis.

A third 28 microliter sample portion is fed to the channel 718 (which can be any one of the channels 518, 526 and 532 of the instrument 540), combined with 50 microliters of the magnetic microspheres with a CD4 specific antibody bound thereto and 72 microliters of the buffer solution. The CD4 specific antibody can be T4 sold by Coulter Immunology Division of Coulter Corporation. The sample portion was mixed for 60 seconds, lysed and quenched as before and then placed in a magnetic field for 30 seconds, before the mixture with the CD4 subset population removed is fed to the analyzer 716. This results in two data peaks 734 and 736 in FIG. 38C. The peak 734 represents the L's without the CD4 subset population and then is compared to the peak 704 by the comparator 724 to obtain the percentage of the CD4 subset population in the sample.

Again, for testing and evaluation purposes, the same blood sample was analyzed in the above manner to obtain four sets of data peaks, one of which is actually depicted in FIGS. 38A–E. The data peaks in each set of data were substantially the same and hence a single set of data can be utilized. The data was averaged over the four sets of data to obtain the results. The average CD4 subset population percentage obtained was 45.7, which was compared with a light sensing instrument for verification purposes, such as the EPICS@ flow cytometer available from Coulter Corporation, which provided a percentage of 47.6.

A fourth 28 microliter sample portion is fed to the channel 718, combined with 50 microliters of the magnetic microspheres with a CD8 specific antibody bound thereto and 72 microliters of the buffer solution. The CD8 specific antibody can be T8 sold by Coulter Immunology Division of Coulter Corporation. The sample portion was again mixed, lysed and quenched and placed in a magnetic field as before. The mixture with the CD8 subset population removed then is fed to the analyzer 716. This results in two data peaks 738 and 740 in FIG. 38D. The data peak 738 represents the L's without the CD8 subset population, which then is compared to the peak 704 by the comparator 724 to obtain the percentage of the CD8 subset population in the sample. The average CD8 subset population percentage obtained was 25.0, which was compared with the light sensing instrument for verification purposes, which provided a percentage of 26.0.

A fifth 28 microliter sample portion is fed to the channel 718, combined with 50 microliters of the magnetic microspheres with a CD2 specific antibody bound thereto and 72 microliters of the buffer solution. The CD2 specific antibody can be T11 sold by Coulter Immunology Division of Coulter Corporation. The sample portion was again mixed, lysed and quenched and placed in a magnetic field as before. The mixture with the CD2 subset population removed then is fed to the analyzer 716. This results in two data peaks 742 and 744 in FIG. 38E. The data peak 742 represents the L's without the CD2 subset population, which then is compared to the peak 704 by the comparator 724 to obtain the percentage of the CD2 subset population in the sample. The average CD2 subset population percentage obtained was 82.7, which was compared with the light sensing flow cytometer instrument, which provided a percentage of 79.0.

The results of another subset analysis utilizing a one dimensional electronic sensing parameter of CD4, CD8 and CD2 subset populations is illustrated in FIGS. 39A–E and 40A–E. DC was utilized to obtain the data in FIGS. 39A–E, while RF was utilized to obtain the data in FIGS. 40A–E, utilizing the same sample portion and measured at the same time.

Figure 39A:
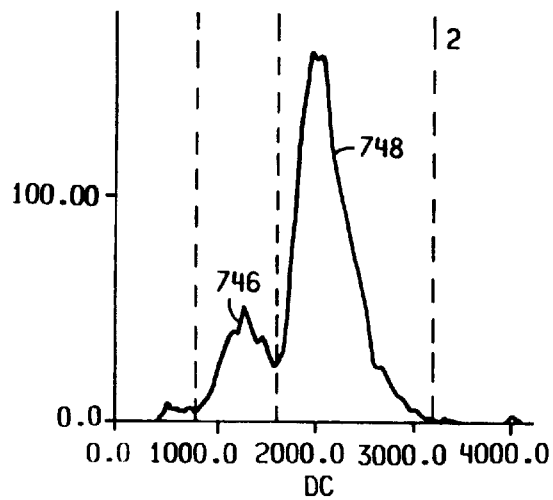
FIGS. 39A–E are scattergrams of another set of results obtained utilizing a DC sensing parameter.
Figure 39B:
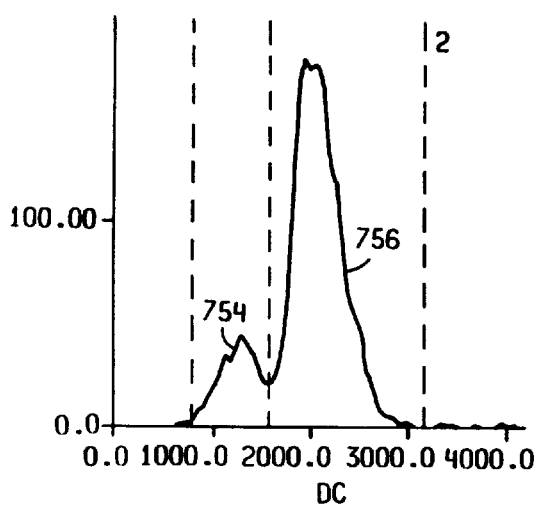
Figure 39C:
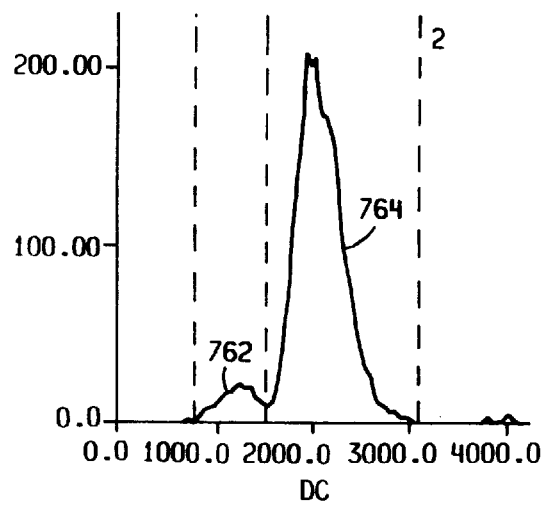
Figure 39D:
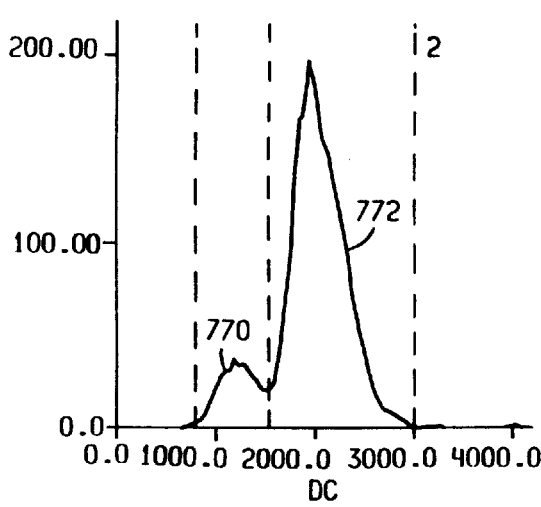
Figure 39E:
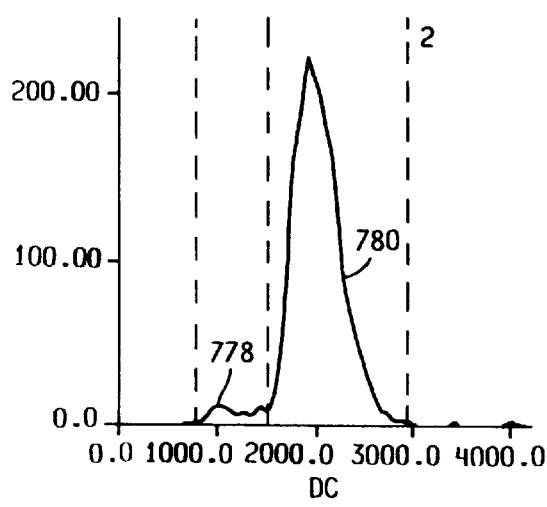
Figure 40A:
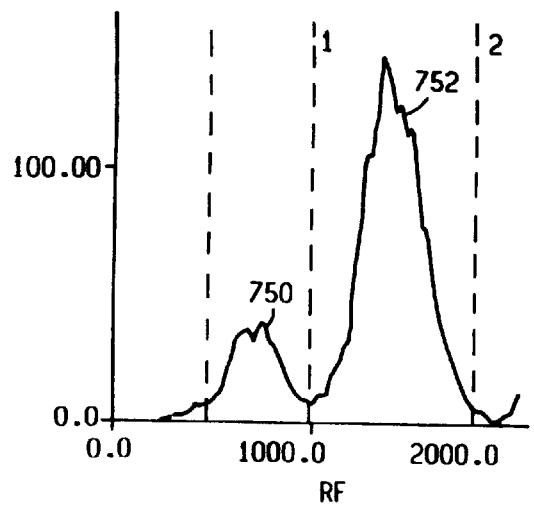
FIGS. 40A–E are scattergrams of the same set of results utilizing an RF sensing parameter.
Figure 40B:
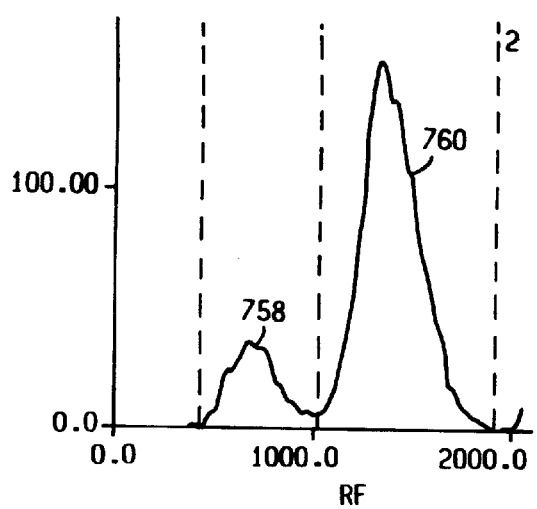
Figure 40C:
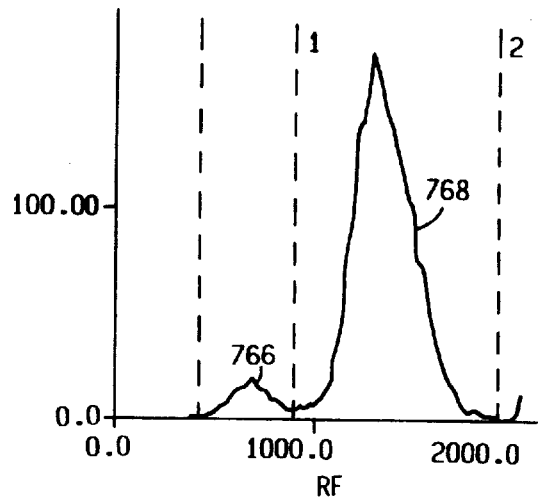
Figure 40D:
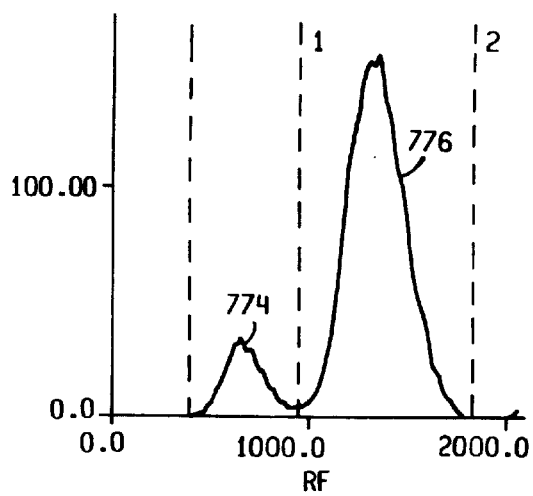
Figure 40E:
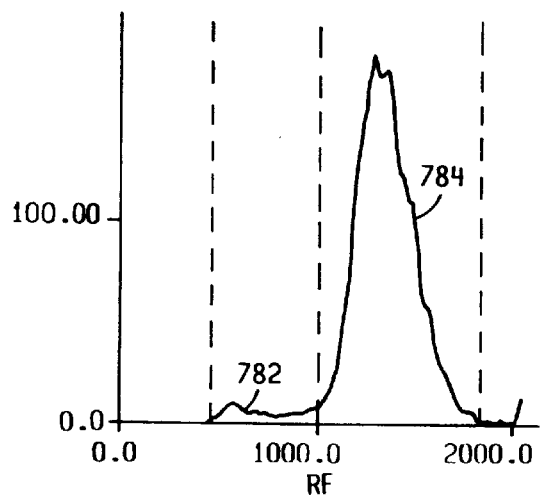

The sample portion was lysed and quenched before being fed to the analyzer 716 in substantially the same manner as described with respect to FIGS. 38A–E. In the case of FIGS. 39A and 40A, only a buffer solution was added and in the case of FIGS. 39B and 40B, a buffer solution as well as magnetic microspheres without the L or L subset specific antibodies were combined with the sample. The control without microspheres resulted in data peaks 746 and 748 in FIG. 39A and data peaks 750 and 752 in FIG. 40A. Peaks 746 and 750 are representative of the L's and B's in the sample. The control with control microspheres combined with the sample, but with the microspheres removed therefrom utilizing the magnetic field, resulted in data peaks 754 and 756 in FIG. 39B and data peaks 758 and 760 in FIG. 40B.

A third whole blood sample portion is combined with 50 microliters of magnetic microspheres with a CD4 specific antibody bound thereto. The mixture is mixed, lysed, quenched and placed in the magnetic field to remove the CD4 subset population for the sample portion mixture before it is fed to the analyzer 716. The DC analysis results in two data peaks 762 and 764 in FIG. 39C, while the RF analysis results in two data peaks 766 and 768 in FIG. 40C. The data peaks 746 and 762 are compared as are the data peaks 750 and 766 to obtain the percentage of the CD4 subset population in the sample.

In FIGS. 39 and 40, the data peaks are one of three separate sample sets from the same whole blood sample which were averaged to obtain the results. In the case of CD4, the percentage obtained from DC was 57.0, RF was 57.1 and the light sensing flow cytometer instrument was 54.6.

To obtain the CD8 subset population analysis, a fourth whole blood sample portion was combined with 50 microliters of magnetic microspheres with a CD8 subset population specific antibody bound thereto. The sample portion is mixed, lysed, quenched and held in a magnetic field to remove the CD8 subset population from the mixture, before the mixture is fed to the analyzer 716. The DC analysis results in two data peaks 770 and 772 in FIG. 39D, while the RF analysis results in two data peaks 774 and 776 in FIG. 40D.

The data peaks 746 and 770 are compared as are the data peaks 750 and 774 to obtain the percentage of the CD8 subset population in the sample. In the case of CD8, the percentage obtained from DC was 17.4, from RF was 18.6 and from the light sensing flow cytometer instrument was 17.7.

To obtain the CD2 subset population analysis, a fifth whole blood sample portion was combined with 50 microliters of magnetic microspheres with a CD2 subset population specific antibody bound thereto. The sample portion is mixed, lysed, quenched and held in a magnetic field to remove the CD2 subset population from the mixture, before the mixture is fed to the analyzer 716. The DC analysis results in two data peaks 778 and 780 in FIG. 39E, while the RF analysis results in two data peaks 782 and 784 in FIG. 40E.

The data peaks 746 and 778 are compared as are the data peaks 750 and 782 to obtain the percentage of the CD8 subset population in the sample. In the case of CD8, the percentage obtained from DC was 79.6 from RF was 79.3 and from the light sensing flow cytometer instrument was 74.7.

The B and L subset population analysis referred to with respect to FIGS. 37–40 was obtained utilizing a one dimensional electronic sensing parameter. A light sensing parameter also could be utilized, as well as two or more sensing parameters such as illustrated in FIGS. 41A–E.

Figure 41A:
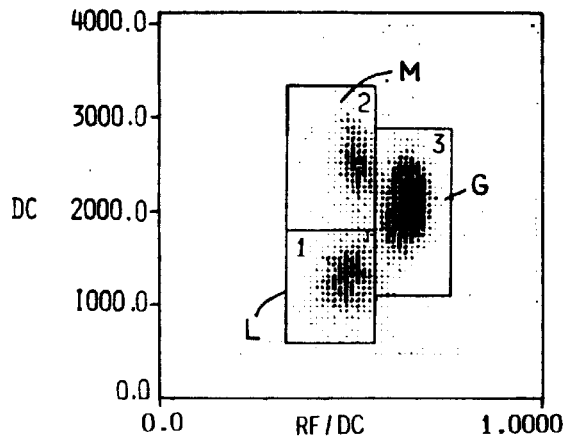
FIGS. 41A–E are scattergrams of one set of results obtained utilizing two sensing parameters.
Figure 41B:
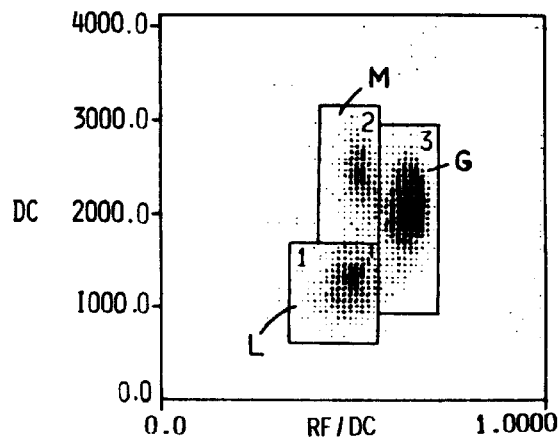

The sample portions are handled in the same manner as those utilized to obtain the data in FIGS. 38–40. FIGS. 41A and 41B illustrate respectively, the results of a control without microspheres and a control combined with magnetic microspheres which are removed prior to analyzing. The controls illustrate the normal three part histograms, illustrating the L's, M's and G's.

Figure 41C:
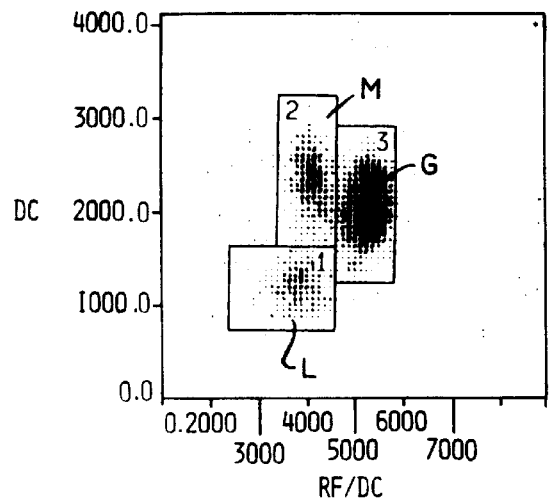

The CD4 depletion is illustrated in FIG. 41C, following the magnetic depletion of the CD4 subset population, the remaining L population can be compared to the control L population to determine the CD4 subset population percentage. The CD4 subset population percentage was determined to be 59.4, which was then compared to the light sensing flow cytometer instrument which determined a percentage of 54.6.

Figure 41D:
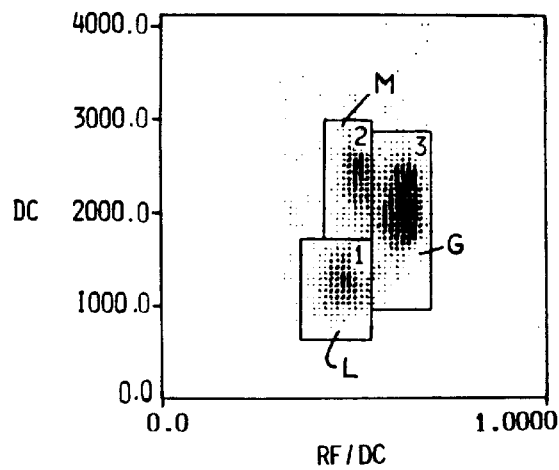

The CD8 depletion is illustrated in FIG. 41D, following the magnetic depletion of the CD8 subset population, the remaining L population can be compared to the control L population to determine the CD8 subset population percentage. The CD8 subset population percentage was determined to be 15.8, which was then compared to the light sensing flow cytometer instrument which determined a percentage of 17.7.

Figure 41E:
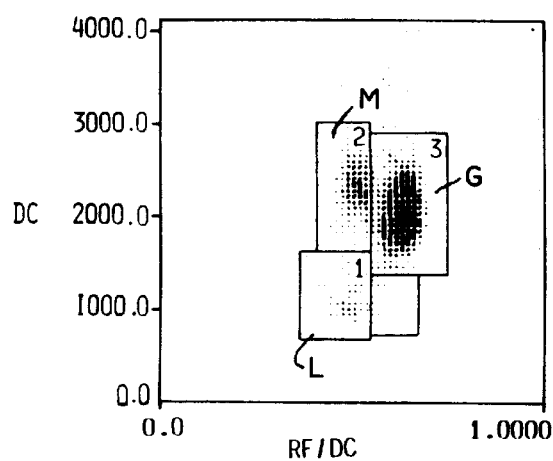

The CD2 depletion is illustrated in FIG. 41E, following the magnetic depletion of the CD2 subset population, the remaining L population can be compared to the control L population to determine the CD2 subset population percentage. The CD2 subset population percentage was determined to be 82.2, which was then compared to the light sensing flow cytometer instrument which determined a percentage of 74.7.

As can clearly be seen by the above analysis, a number of the subset populations overlap, since the individual L subset populations add to greater than 100. "Overlapping" is utilized herein to signify that certain cells, populations of cells, subpopulations of cells or formed bodies include at least two receptors or antigens of interest. Overlapping can be a significant parameter in diagnosis and treatment and will be discussed in further detail hereinafter.

All the data referred to heretofore, has been what would be called "normal" whole blood samples. "Normal" is utilized herein to signify that a whole blood sample is not substantially infected, such as by a cancer or other disease.

FIGS. 42 and 43 illustrate the results of analyzing two abnormal whole blood samples. The first sample depicted in FIGS. 42A–G was analyzed and displayed in several different manners. FIGS. 42A and 42B depict two different two dimensional sensing histograms of the whole blood sample, one with light sensing and one with only electronic sensing, without any treatment of the blood sample. Clearly, the normal blood sample L, M and G grouping, for example, as illustrated in FIG. 41A is totally obscured and there is just one unidentifiable data grouping.

Figure 42A:
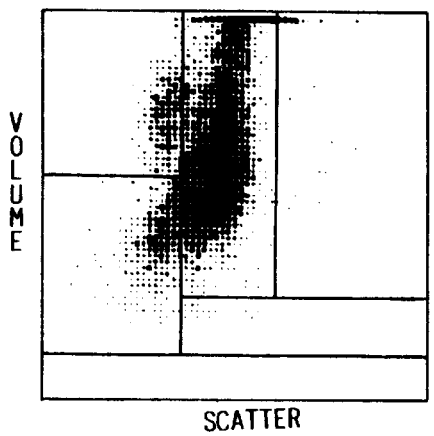
FIGS. 42A–G and 43A–G are scattergrams of results obtained utilizing various sensing parameters on two respective abnormal blood samples.
Figure 42B:
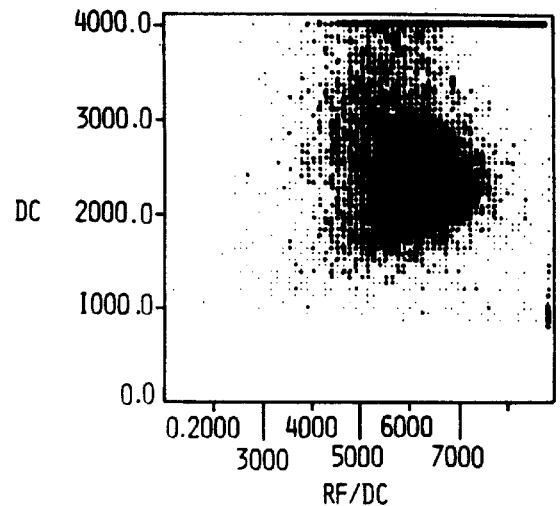
Figure 42C:
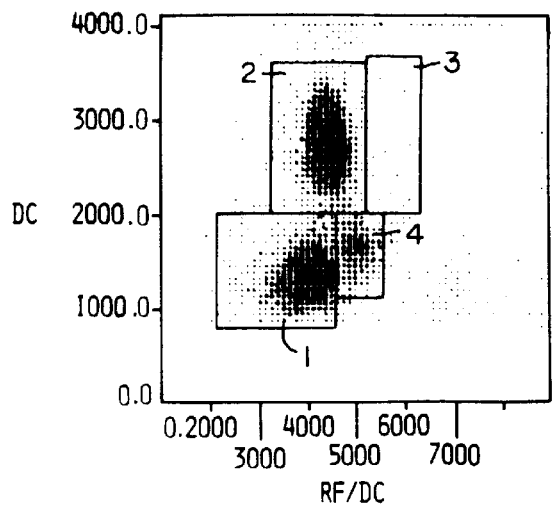
Figure 42D:
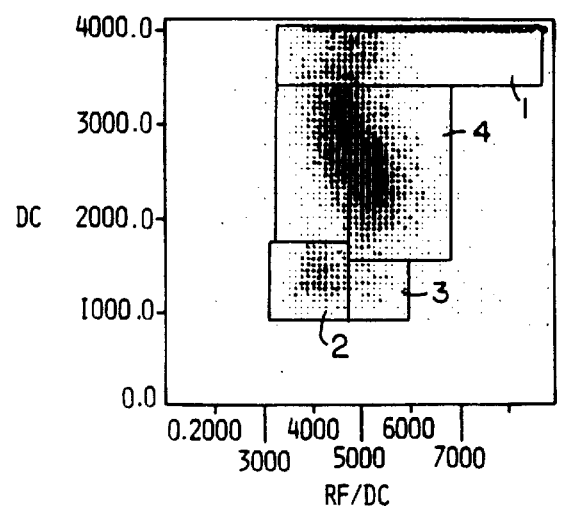

The results of two different treatments of the abnormal whole blood sample are illustrated in FIGS. 42C and 42D. In FIG. 42C, a 200 microliter portion of the sample was combined with 200 microliters of magnetic microspheres having a N and E specific antibody bound thereto. The mixture is mixed, lysed, quenched and held in a magnetic field while the remaining portion is removed and fed to the analyzer without the N and E bound cells therein. It appears clear that a substantial portion of the abnormal cells have been removed, since the pattern in FIG. 42C has become very much more defined than the pattern in FIG. 42B.

In the second treatment, a 200 microliter portion of the sample was combined with 200 microliters of magnetic microspheres having only a N specific antibody bound thereto. Although some of the cells have been removed, indicating that some are bound to the N antibody, a significant portion of the abnormal cells remain, especially as seen at the top of the histogram. It would therefore appear that some of the abnormal or diseased cells bind to the N+E antibody. This type of depletion treatment can be utilized for diagnosis and treatment of particular diseases.

Figure 42E:
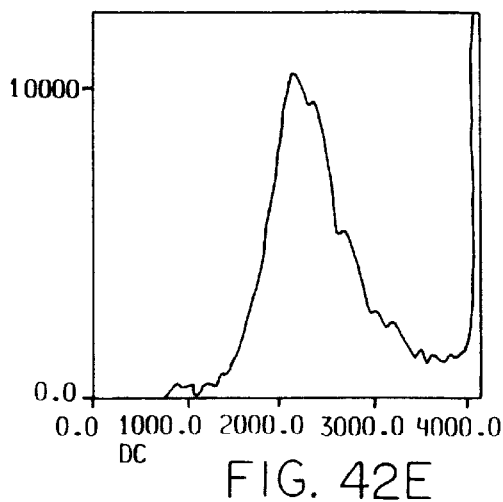
Figure 42F:
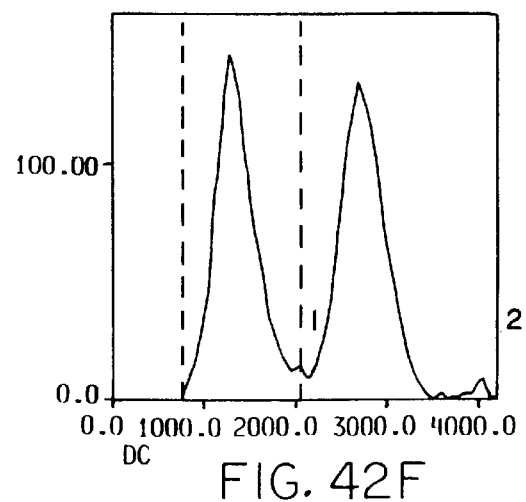
Figure 42G:
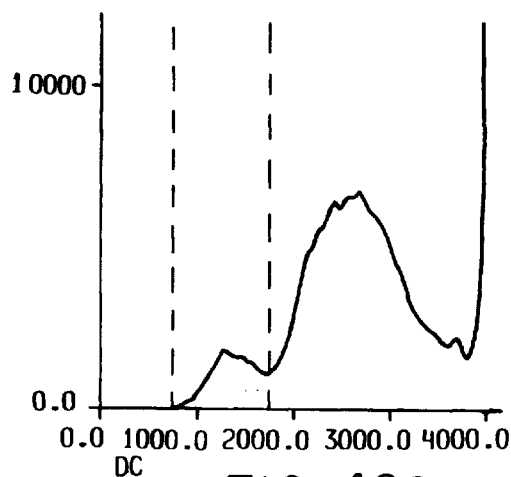

The data histograms of FIGS. 42A–D were developed utilizing two dimensional sensing. The same information can be developed utilizing a single sensing parameter, for example, a single electronic sensing parameter as depicted in FIGS. 42E–42G. The one dimensional sensing, here DC, produces the histogram depicted in FIG. 42E when the sample is analyzed without any treatment. The single data peak and the data at the far right of the histogram are clear indications of an abnormal sample.

Again, the same treatment was utilized as referred to above with respect to FIGS. 42C and 42D and, in fact, the one dimensional sensing data was generated at the same time as the two dimensional sensing data. The analyzing instrument can, as described above, include multiple sensing parameters or only one single parameter. Again, the removal of the N and E bound cells produces a histogram in FIG. 42F, which again illustrates that most of the abnormal cells have been removed. The histogram in FIG. 42G illustrates again that a significant number of the abnormal cells have not been removed.

The results of analyzing the second abnormal whole blood sample are illustrated in FIGS. 43A–G. The results of analyzing the sample without treatment are illustrated in two dimensional histograms in FIGS. 43A and 43B. Clearly, a normal whole blood sample data pattern is not seen. The histogram of FIG. 43B prepared in the instrument, can be compared to the histogram in FIG. 43C prepared offline, which do not appear significantly different. A 28 microliter sample portion was prepared offline or preprepared before the analysis depicted in FIG. 43C.

Figure 43A:
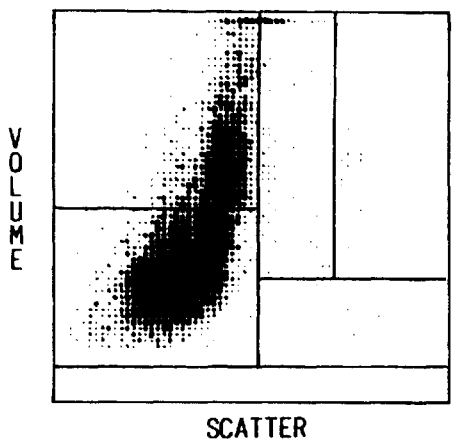
Figure 43B:
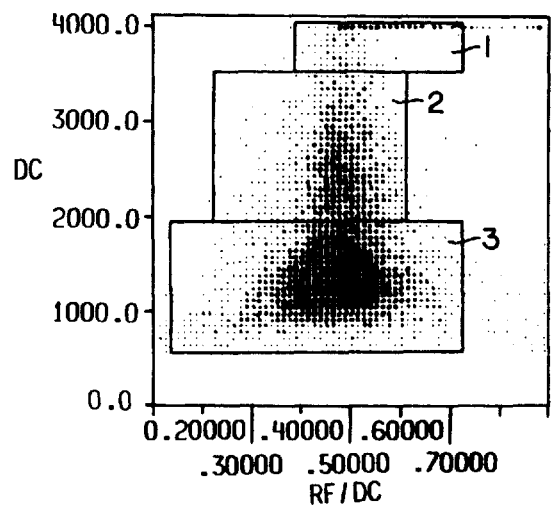
Figure 43C:
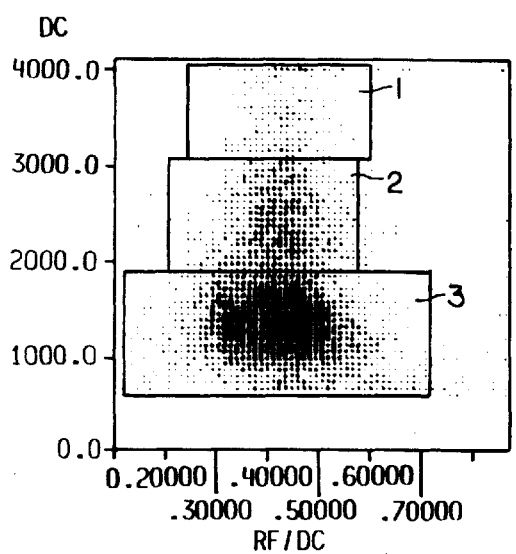
Figure 43D:
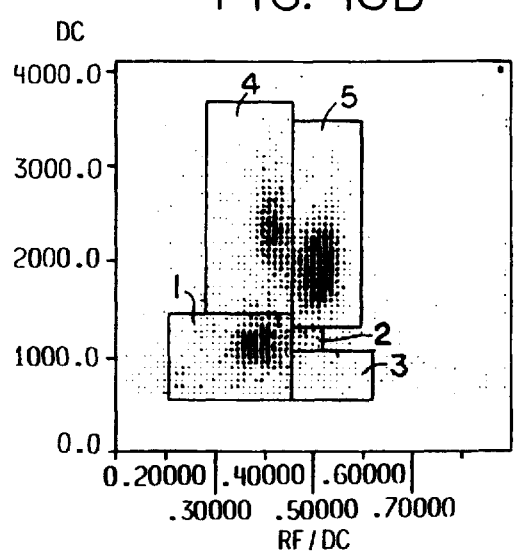

A portion of the sample was depleted of the CD5 subset population and then analyzed to provide the histogram in FIG. 43D. A 28 microliter portion of the whole blood sample was combined with 122 microliters of magnetic microspheres having a CD5 specific antibody bound thereto, such as T1 sold by Coulter Immunology Division of Coulter Corporation. The mixture was mixed, lysed, quenched and held in a magnetic field to remove the CD5 bound cells. This clearly removed a significant portion of the abnormal cells as can be seen by comparing FIGS. 43B or FIG. 43C with FIG. 43D. The histograms of FIGS. 43A–D were made with two dimensional sensing, while the same data is depicted in one dimension histograms in FIGS. 43E–G.

Figure 43E:
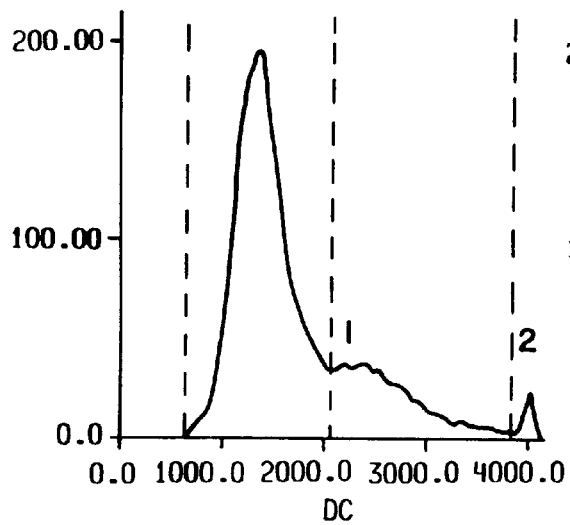
Figure 43F:
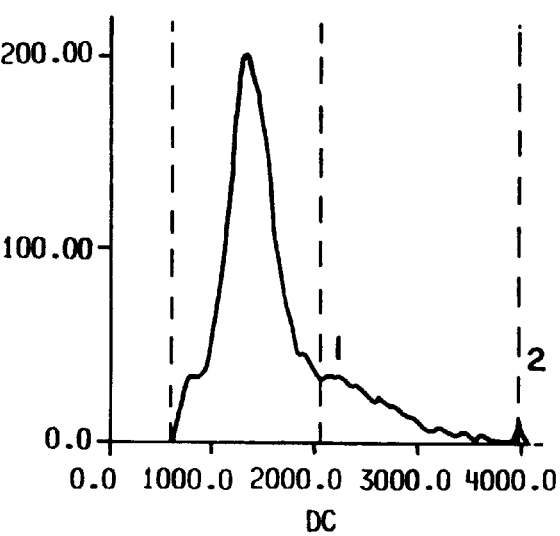
Figure 43G:
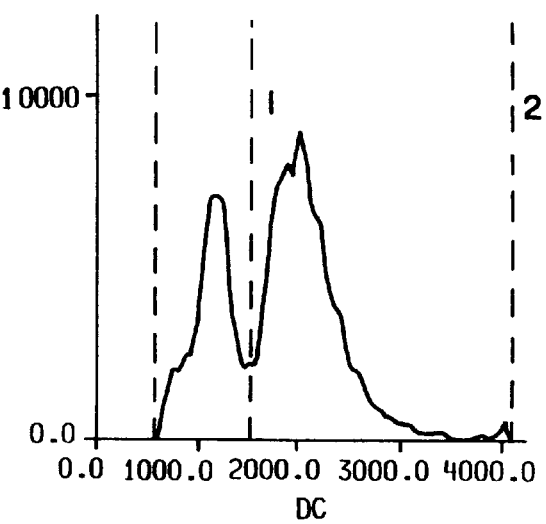

Again, no treatment was performed on the online sample depicted in FIG. 43E or on the offline sample depicted in FIG. 43F and the CD5 subset population was depleted from the sample depicted in FIG. 43G.

As discussed hereinbefore, the overlapping populations of cells can be of interest for diagnostic as well as treatment of diseases of the blood. For example, some immature cells express both CD4 and CD8 receptors. The obtaining of an analysis of the overlapping percentage of cell subset populations has not been available when utilizing electronic sensing parameters or a minimal number of light parameters or simplified combinations thereof. For example, in some light sensing instruments, three sensing parameters are utilized to obtain the overlapping data, both forward and 90° light scatter and fluorescence. One example of overlapping populations in a normal whole blood sample is the CD2 and CD8 subset populations. An abnormal overlapping of populations is found in CLL (chronic lyphocytic leukemia). In the CLL disease state, the CD5 and CD20 subset populations overlap.

Figure 44:
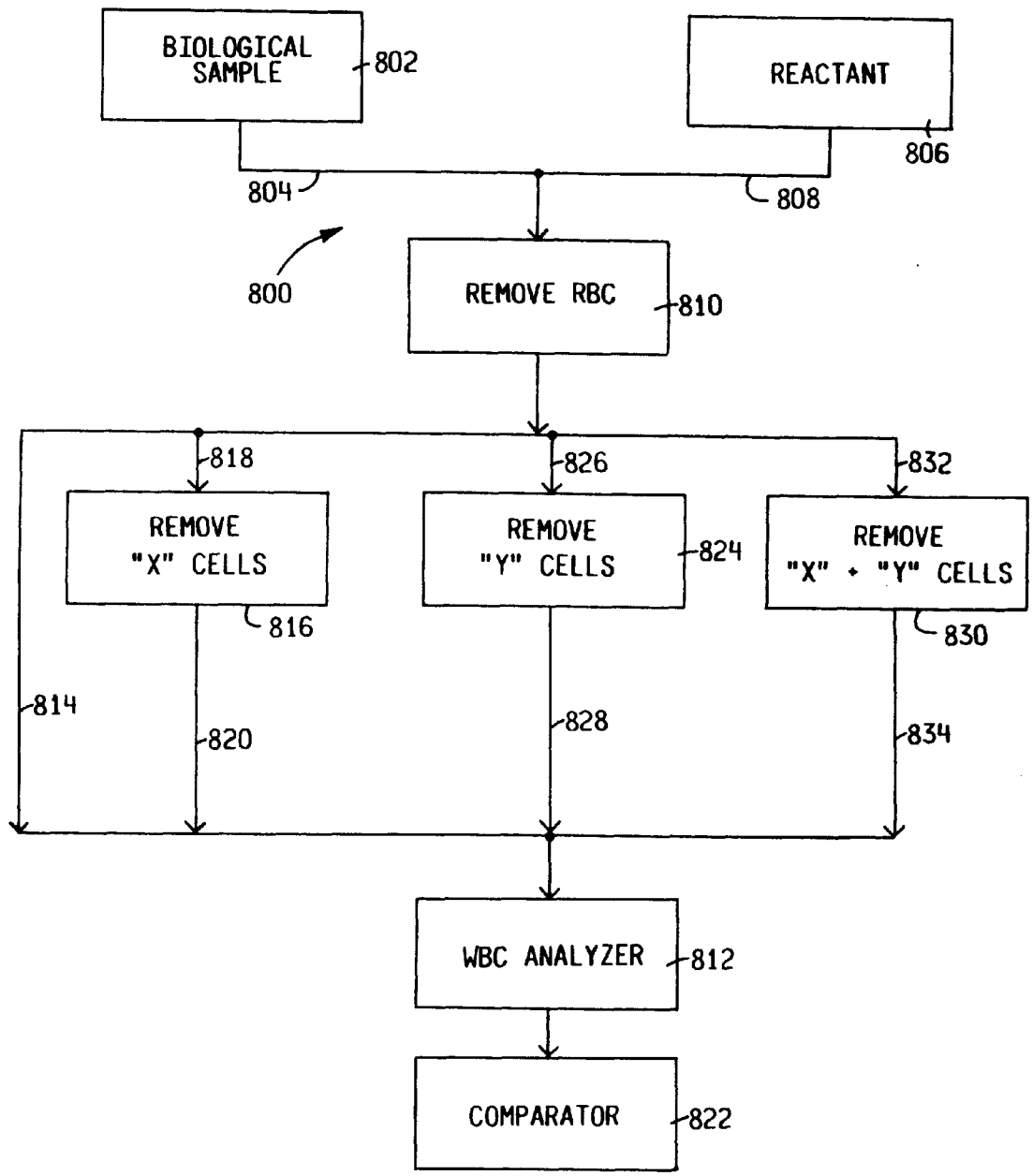

Referring to FIG. 44, a first embodiment of a method and apparatus for performing an overlapping classification of cells is designated generally by the reference numeral 800. The instrument or analyzer 800 includes a biological sample 802, which contains at least a first set of viable biological cells (not illustrated), including at least two overlapping white blood cell populations or subset populations, such as in or from a whole blood sample.

The cells of the biological sample 802 are to be involved in a biological reaction in a quantitative and/or qualitative determination or analysis. The biological sample 802 can include a buffer into which the cells are added.

The biological sample 802 is combined via a line 804 with at least one reactant 806 via a line 808. In the analyzer 800, the RBC's are removed from the mixture at an RBC removing station 810. As stated in the first parent application, the RBC's can be removed from the station 810 in a number of ways, such as enumerated with respect to the station 20.

A first portion of the mixture with the RBC's removed, then is fed to a WBC analyzer 812 via a line 814. This obtains a standard or control for the total or whole WBC populations of the biological sample 802. The analyzer 812 can be the same as the analyzer 86 or can be a light sensing analyzer, such as described in U.S. Ser. No. 025,442 filed Mar. 13, 1987 and U.S. Ser. No. 129,954, filed Dec. 4, 1987, entitled *MULTI-PART DIFFERENTIAL ANALYZING APPARATUS UTILIZING LIGHT SCATTER TECHNIQUES*, which are incorporated herein by reference. The single sensing parameter can be electronic, such as RF or DC or light, such as median angle light scatter (Scatter) or any other desired light parameter.

A second portion of the mixture is fed to an "X" removing station 816 via a line 818. The station 816 removes a first overlapping population of cells "X". The X's are removed or depleted by the addition of the appropriate magnetic microspheres with an X specific antibody bound thereto. A magnet or magnetic field is utilized, as before discussed, to remove the magnetically bound cells from the mixture. The remaining mixture with the X's removed then is fed via a line 820 to the analyzer 812. The analyzed results of the "X" removed portion of the mixture than can be compared with the analyzed results of the first mixture portion in a comparator 822 to obtain the percentage of X's in the biological sample 802.

A third portion of the mixture is fed to a second removing station 824 via a line 826. The station 824 removes a second overlapping population of cells "Y". The Y's are removed by the addition of appropriate magnetic microspheres with a Y specific antibody bound thereto. The remaining mixture with the Y's removed then is fed via a line 828 to the analyzer 812. The analyzed results of the "Y" removed portion of the mixture then is compared to the results of the first and second mixture portions in the comparator 822 to verify if there is an overlapping of the X and Y populations in the biological sample 802. This operation verifies that the X and Y populations overlap, only if the X and Y populations or population ratios are generally known or if the total of the X and Y depleted populations is greater than 100%.

In most cases, a fourth portion of the mixture is fed to a removing station 830 via a line 832. The station 830 removes both the X and Y populations (X+Y). The X's and Y's are removed by the addition of the appropriate magnetic microspheres with the X and Y specific antibodies bound thereto. The remaining mixture with the X's and Y's removed then is fed via a line 834 to the analyzer 812. The analyzed results of the "X"+"Y" removed portion of the mixture then can be compared to the results of the other mixture portions to obtain the percentage of overlapping of the X and Y populations in the biological sample 802.

Thus, the analyzer 800 can perform a single overlapping classification of cells, utilizing lines or channels 814, 818 and 826 and a full percentage overlapping classification utilizing all four lines. One most important feature of the analyzer 800 is that the mixtures can be analyzed utilizing only a single analyzing parameter, such as one electronic parameter or one light parameter. Other combinations can be utilized, but in each case only a single sensed parameter or characteristic is necessary to perform the overlapping classification of the parent application. The analysis also can be obtained with multiple sensing parameters.

A specific analyzing instrument embodiment incorporating the method and apparatus of the analyzer 800 is not illustrated, however, one such instrument can be the instrument 540. Again, the overlapping method and apparatus can be practiced on only a single channel of the instrument 540 or on a single channel instrument, not illustrated.

Referring now to FIGS. 45A–45D, one set of one dimensional scattergram overlapping characterization results are illustrated, obtained from a whole blood sample, utilizing a prototype analysis method similar to the analyzer instrument 540 and described with respect to the instrument 800. The biological sample in each case was a 28 microliter sample of whole blood, which was combined with 122 microliters of buffer solution utilized in the first channel 814. The sample portion was lysed with 300 microliters of the above referenced RBC preferential lyse for 4 seconds and then quenched with 120 microliters of quench before being fed to the analyzer 812.

Figure 45A:
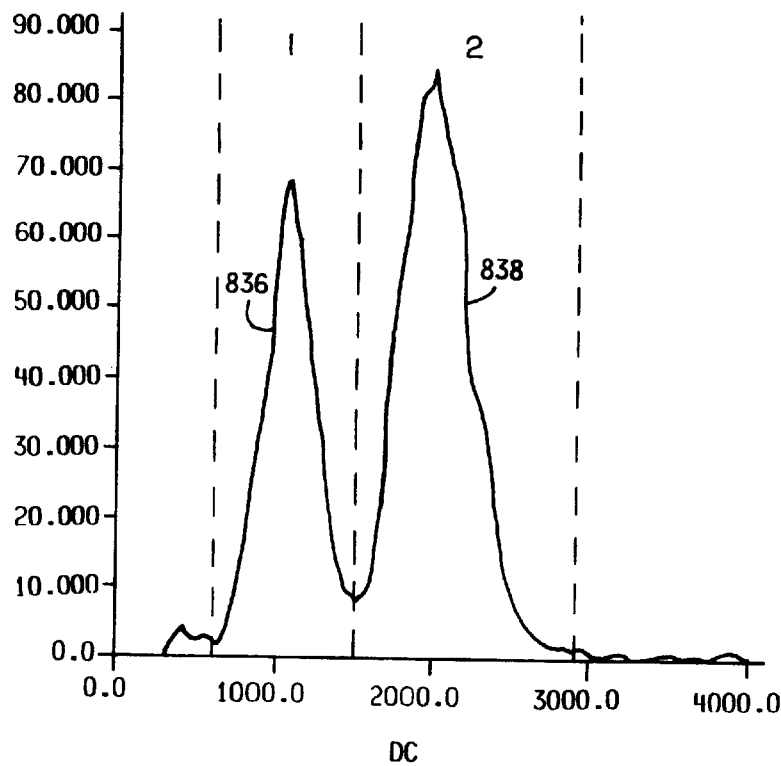
FIGS. 45A–D and 46A–D are scattergrams of two sets of results utilizing a prototype analyzer system and a DC sensing parameter similar to that illustrated in FIGS. 27 and 44.
Figure 45B:
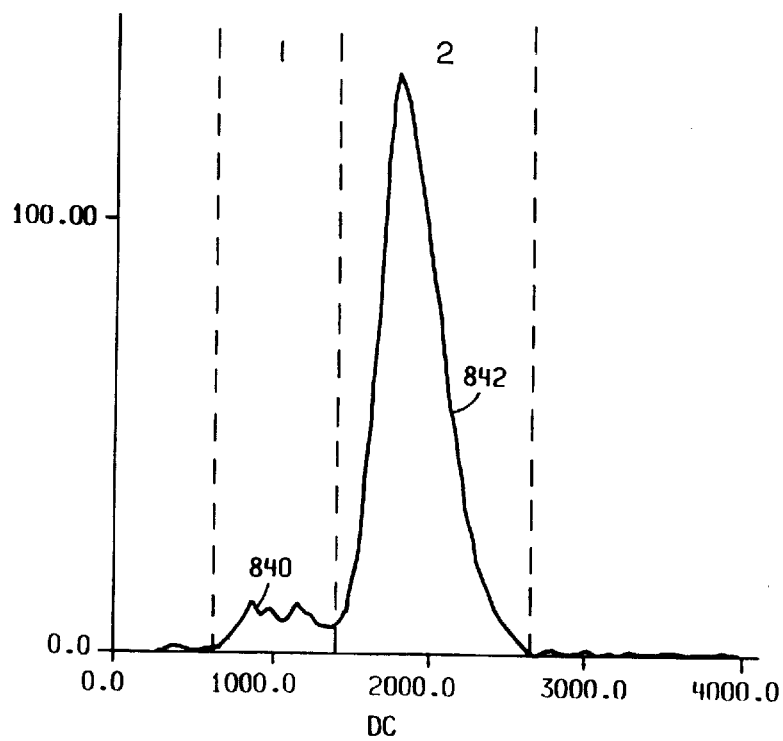
Figure 45C:
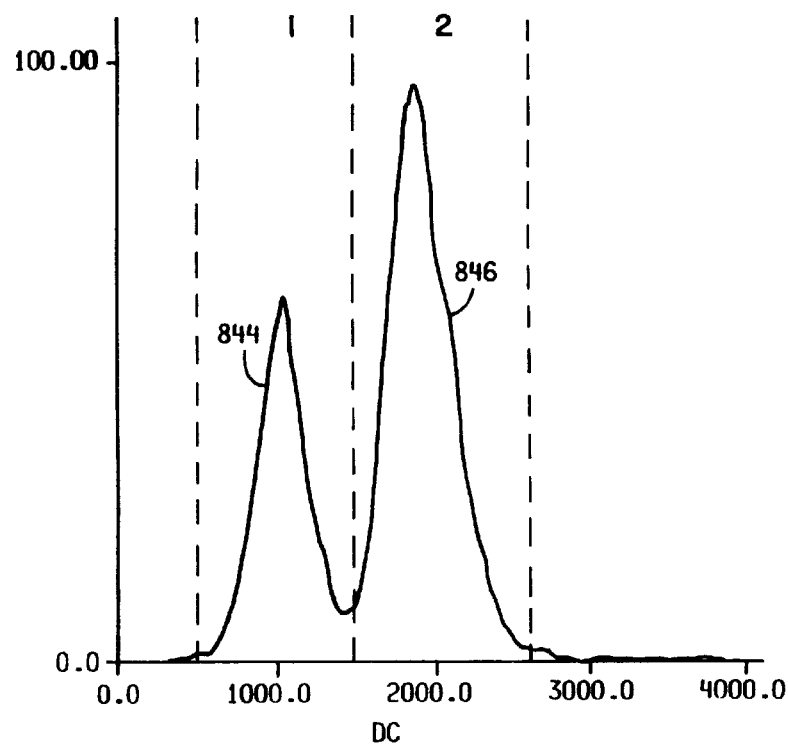
Figure 45D:
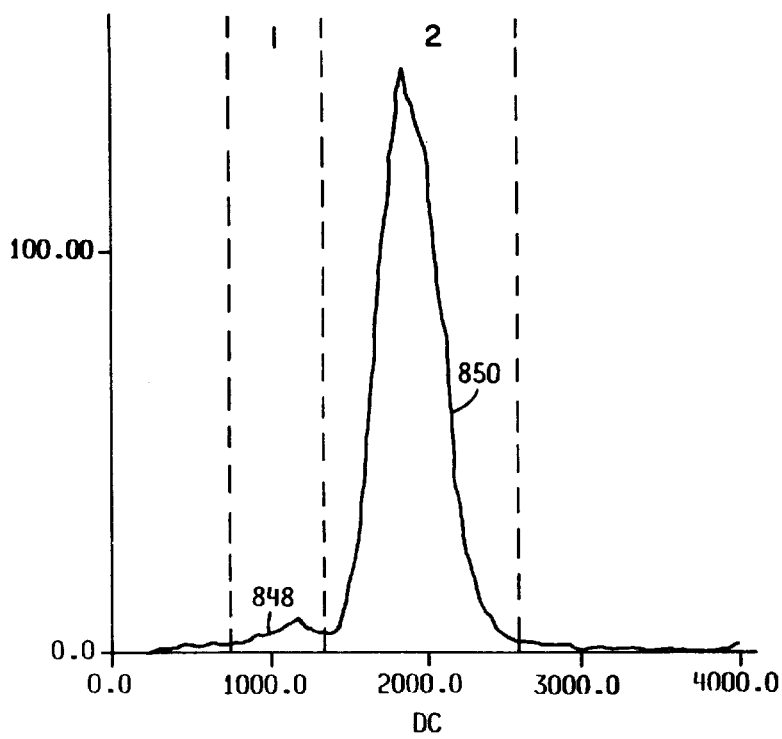

The data results of analyzing the portion with a one dimensional electronic sensing parameter, here DC, is illustrated in the histogram of FIG. 45A. The data results in two clearly identifiable data peaks 836 and 838. As before, the peak 836 is indicative of the percentage of L's and B's in the sample, while the peak 838 is indicative of the percentage of N's, E's and M's.

The sample was then treated to deplete first the X and then the Y cell populations as above referenced. In this case, the X population was the CD2 subset population of the L's and the Y population was the CD20 subset population of the L's. A second portion of the sample was fed to the station 816, wherein 60 microliters of magnetic microspheres having a CD2 specific antibody bound thereto was combined with the sample portion, mixed, lysed, quenched and then held in a magnetic field to remove the CD2 subset population. The remaining mixture then was fed to the analyzer 822 resulting in two data peaks 840 and 842 in FIG. 45B. The peak 840 is the remaining L's, which then is compared in the comparator 822 to the peak 836 to obtain the percentage of the CD2 subset population in the sample.

A third portion of the sample is fed to the station 824, wherein 50 microliters of magnetic microspheres having a CD20 specific antibody bound thereto was combined with the sample portion, mixed, lysed, quenched and then held in a magnetic field to remove the CD20 subset population. The remaining CD20 removed mixture then was fed to the analyzer 822 resulting in two data peaks 844 and 846 in FIG. 45C. The peak 844 is the remaining L's, which then is compared to the peak 836 to obtain the percentage of the CD20 subset population in the sample.

If the normal relative percentages of the CD2 and CD20 subsets are known, then this can be sufficient to identify that the subset populations are overlapping. Also, if the two subset population percentages add to a total of greater than 100 percent, then clearly, this also indicates that the two subset populations overlap. In cases of small overlapping percentages, it then is important to obtain the percentage of overlapping subset populations to verify that the subset populations do overlap. A further depletion is necessary to obtain the overlapping percentage.

A fourth portion of the sample is fed to the station 830, wherein magnetic microspheres having the CD2 specific antibody and magnetic microspheres having the CD20 specific antibody bound thereto are combined to remove both the CD2 and CD20 subset populations. The remaining CD2 and CD20 depleted mixture then was fed to analyzer 822 resulting in two data peaks 848 and 850 in FIG. 45D. The peak 848 again is the remaining L's, which then is compared to the peak 836 to obtain the percentages of subset populations removed by the CD20 and CD2 specific antibodies. This result then is compared to the individual CD2 and CD20 results to obtain the overlapping percentages, if any.

The exact overlapping percentages are calculated as follows:

I. Subset "A" (CD2)

$$\frac{\text{(Data Peak 838)}}{\text{(Data Peak 842)}} \times \text{(Data Peak 840)} = A' \quad \text{(a)}$$

$$\frac{\text{(Data Peak 836)} - A'}{\text{(Data Peak 836)}} = \% \text{ Subset } A \ (CD2) \quad \text{(b)}$$

II. Subset "B" (CD20)

$$\frac{\text{(Data Peak 838)} - A'}{\text{(Data Peak 846)}} \times \text{(Data Peak 844)} = B' \quad \text{(a)}$$

$$\frac{\text{(Data Peak 836)} - B'}{\text{(Data Peak 836)}} = \% \text{ Subset } B \ (CD20) \quad \text{(b)}$$

III. Subset "A+B" (CD2+CD20)

$$\frac{\text{(Data Peak 838)} - A'}{\text{(Data Peak 850)}} \times \text{(Data Peak 848)} = A' + B' \quad \text{(a)}$$

$$\frac{\text{(Data Peak 836)} - A' + B'}{\text{(Data Peak 836)}} = \% \text{ Subsets } A + B \quad \text{(b)}$$

IV. Overlapping Portion

[Subset "A"+Subset "B"] −[(Subset "A+B"]=overlap

The results (averaged from two separate preparations) are illustrated in Table VI as follows:

TABLE VI

|  | Peak | Relative Percentage | Peak | Relative Percentage |
| --- | --- | --- | --- | --- |
| Control | 836 | 35.7 | 838 | 64.3 |
| CD2 | 840 | 7.1 | 842 | 92.9 |
| CD20 | 844 | 33.6 | 846 | 66.4 |
| CD2 + CD20 | 848 | 3.5 | 850 | 96.5 |

The relative percentages in Table VI are the percentage of the two peaks of the total percentage of 100. The percentage of CD2 was calculated as 86.2, CD20 was 8.9 and CD2+CD20 was 93.5. Therefore, the overlapping percentage was (CD2+CD20)−CD2+CD20 =(86.2+8.9)−93.5=1.6.

A second sample was depleted to obtain the percentage overlap of the CD2 and CD8 subset populations as illustrated in FIGS. 46A–D. Again, a first portion of the sample was fed to the channel 814 without a depletion to obtain the control data illustrated in FIG. 46A. The data results in two clearly identifiable data peaks 852 and 854. The peak 852 again is indicative of the percentage of L's and B's in the sample.

Figure 46A:
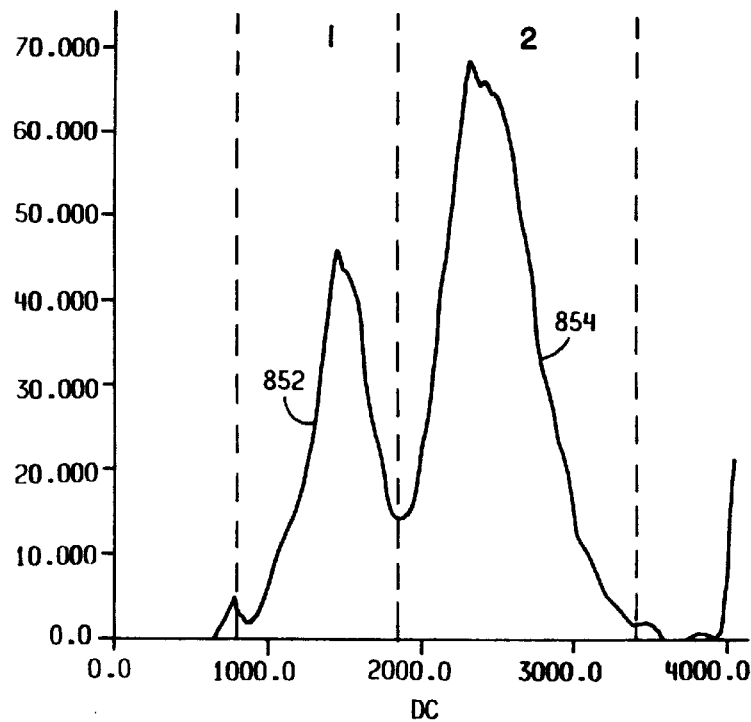
Figure 46B:
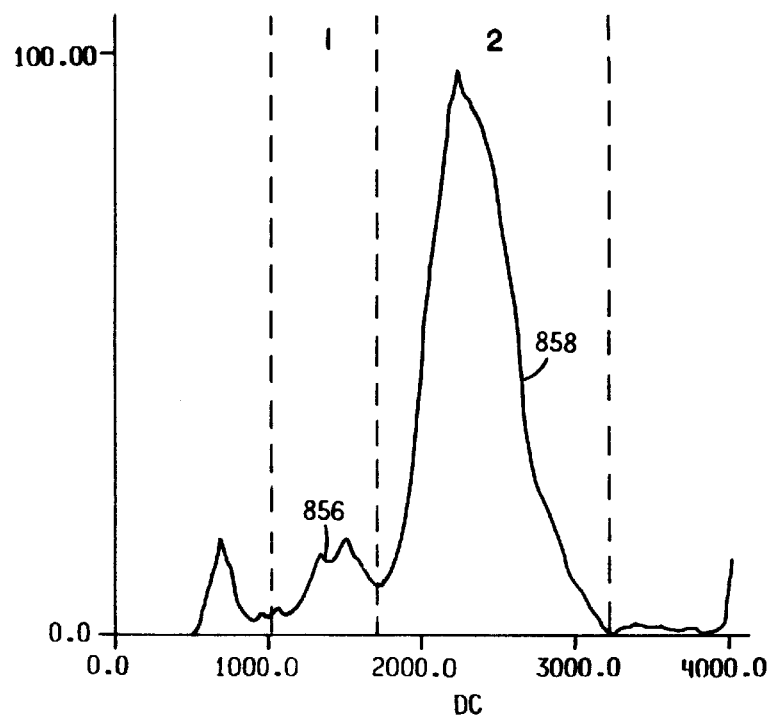

A second sample portion is depleted of the CD2 subset population as before described in the channel 818, resulting in two data peaks 856 and 858 in FIG. 46B. The remaining L peak 856 again is compared to the control peak 852 to obtain the percentage of the CD2 subset population in the sample.

Figure 46C:
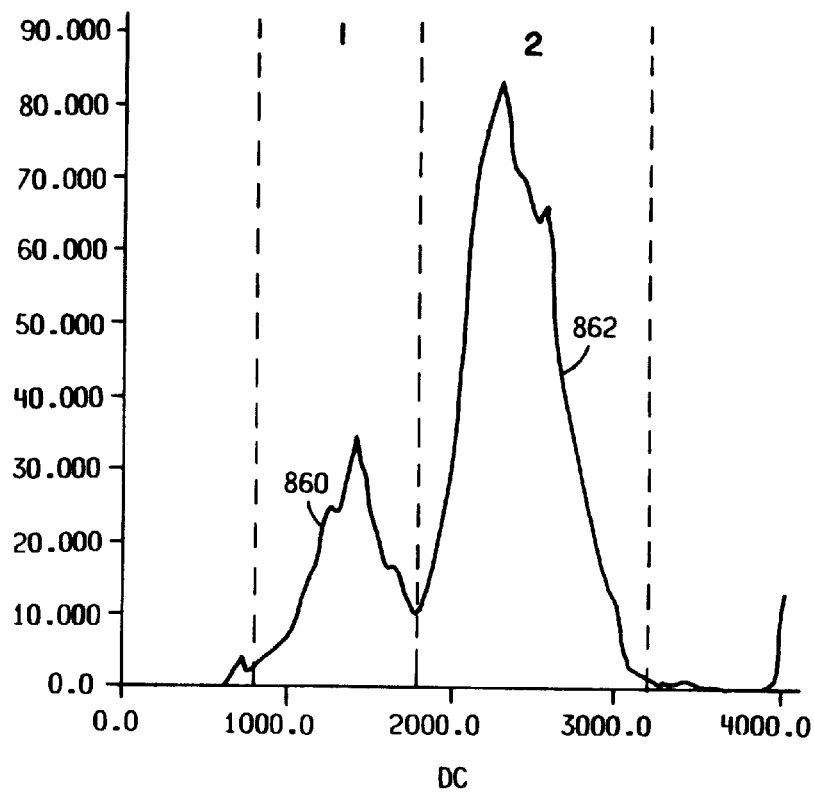

A third sample portion is depleted of the CD8 subset population in the channel 826, resulting in two data peaks 860 and 862 in FIG. 46C. The peak 860 is compared to the control peak 852 to obtain the percentage of the CD8 subset population in the sample.

Figure 46D:
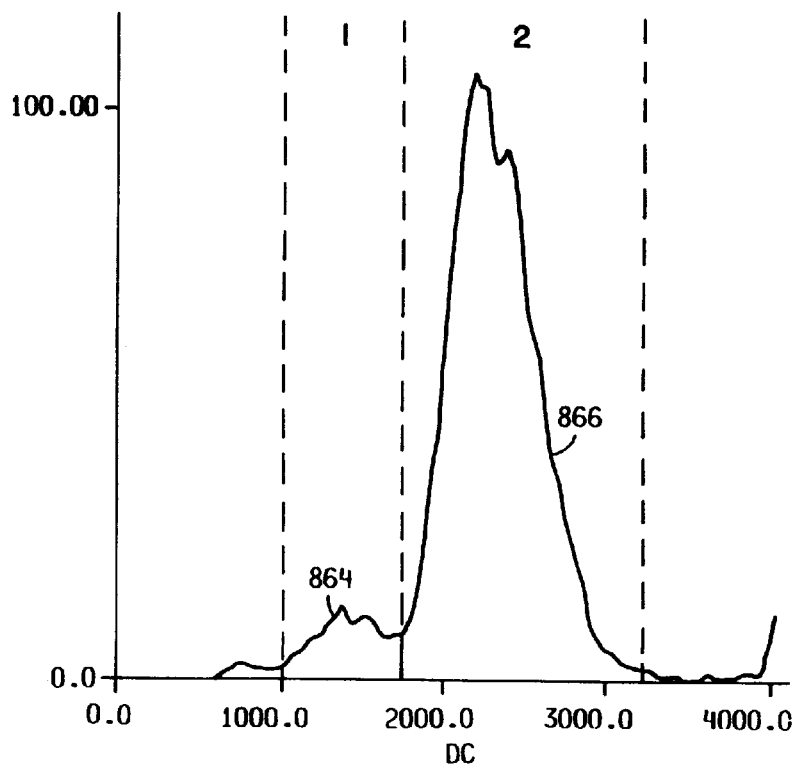

A fourth sample portion is depleted of the CD2+CD8 subset populations in the channel 832, resulting in two data peaks 864 and 866 in FIG. 46D. The peak 864 is compared to the control peak 852 to obtain the percentage of CD2+CD8 subset populations in the sample.

The results are illustrated in Table VII as follows:

TABLE VII

|  | Peak | Relative Percentage | Peak | Relative Percentage |
| --- | --- | --- | --- | --- |
| Control | 852 | 30.3 | 854 | 69.7 |
| CD2 | 856 | 9.0 | 858 | 91.0 |
| CD8 | 860 | 22.1 | 862 | 77.9 |
| CD2 + CD8 | 864 | 7.6 | 866 | 92.4 |

The percentage of CD2 was calculated as 77.3, CD8 was 34.7 and CD2+CD8 was 81.1. Therefore, the overlapping percentage was (77.3+34.7)−81.1=30.9.

Referring now to FIGS. 47–60, the embodiments of the present invention are illustrated.

Figure 47:
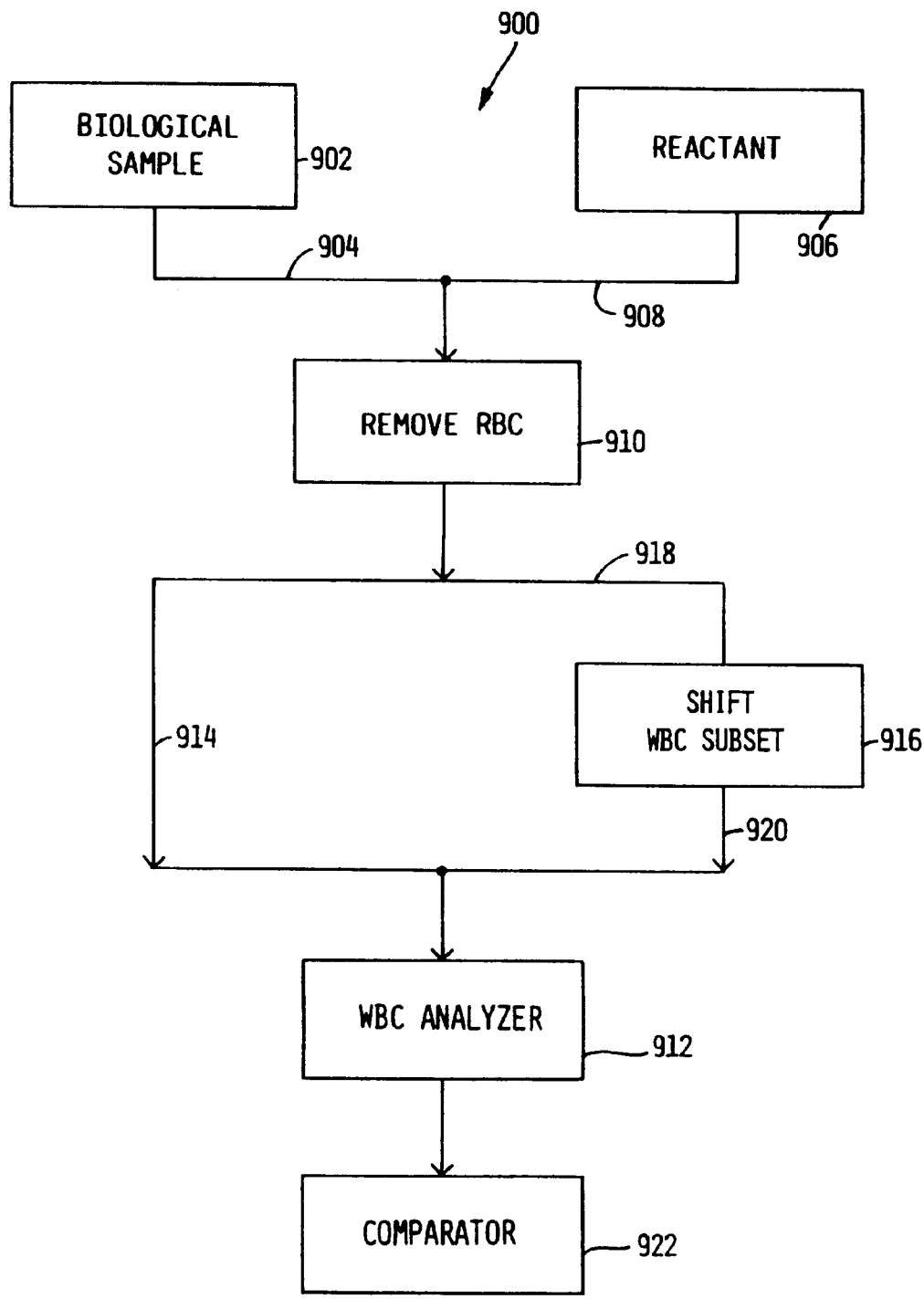
FIGS. 47–60 are directed to embodiments of the present invention.

Referring to FIG. 47, a first embodiment of a method and apparatus for performing classifications of obscured or partially obscured cells, specifically, for example purposes those cells forming a white blood cell population subset of interest is designated generally by the reference numeral 900. The instrument or analyzer 900 includes a biological sample 902, which contains at least a first set of viable biological cells (not illustrated), including at least two white blood cell populations, such as in or from a whole blood sample. At least one of the white blood cell populations includes a white blood cell population subset of interest, the sensed characteristics of which are obscured by the white blood cell population. The sensed characteristics are to be shifted by binding microspheres having monoclonal antibodies specific thereto to the white blood cell population subset, however, the shifted sensed characteristic will be obscured or partially obscured by the second white blood cell population.

The cells of the biological sample 902 are to be involved in a biological reaction in a quantitative and/or qualitative determination or analysis. The biological sample 902 can include a buffer into which the cells are added. The biological sample 902 is combined via a line 904 with at least one reactant 906 via a line 908. In the analyzer 900, the RBCs are removed from the mixture at an RBC removing station 910.

As stated in the first parent application, the RBC's can be removed from the station 910 in a number of ways, utilizing lyse and/or microspheres, such as enumerated with respect to the station 20.

A first portion of the mixture with the RBC's removed, then is fed to a white blood cell analyzer 912 via a line 914. This obtains a standard or control for analyzing the white blood cell populations of the biological sample 902 for an obscured white blood cell subset population of interest. The standard population can be one of the total number of white blood cell populations, a second white blood cell population which does not obscure the shifted or non-shifted sensed characteristic of the subset of interest, an artificial population formed by microspheres which also do not obscure the shifted or non-shifted sensed characteristic of the subset of interest or a white blood cell population into which the sensed characteristic of the subset will be wholly or partially shifted. The artificial population can be formed from microspheres which do not have antibodies or cells bound thereto and form a sensed characteristic which does not obscure the first white blood cell population or the shifted characteristic of the white blood cell subset of interest. The analyzer 912 can be the same as the analyzer 86. The analyzer 912 utilizes two electronic sensing parameters, such as RF or DC.

The white blood cell population subset of interest is obscured in one of the sensed white blood cell populations. A second portion of the mixture is fed to a white blood cell population subset shifting station 916 via a line 918. The white blood cell population subset is bound to white blood cell microspheres having monoclonal antibodies specific to the subset thereon to modify (change or shift) the resultant opacity and/or volume parameters of the cells.

The mixture with the white blood cell population subset shifted, then is fed to the analyzer 912 via a line 920. The white blood cell population subset of interest generally is related as a percentage of the white blood cell population of interest. The results of the white blood cell analyzer 912 from the original or non-shifted cell mixture then is compared in a comparator 922 to obtain the percentages of the white blood cell population.

The instrument 900 can be substantially identical to the instrument 540, utilizing only the lines 514 and 518, without the magnetic field 592. The instrument 900 also can be a sequential type instrument, such as the instrument 56, in which the same sample portion can be counted, then shifted, recounted and compared.

Figure 48A:
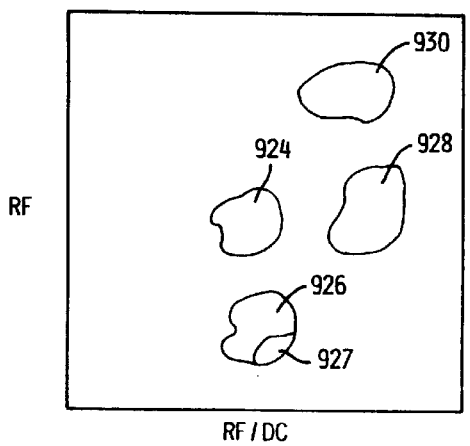
FIGS. 48A and B are conceptual scattergrams illustrating the methodology utilized in the present invention.
Figure 48B:
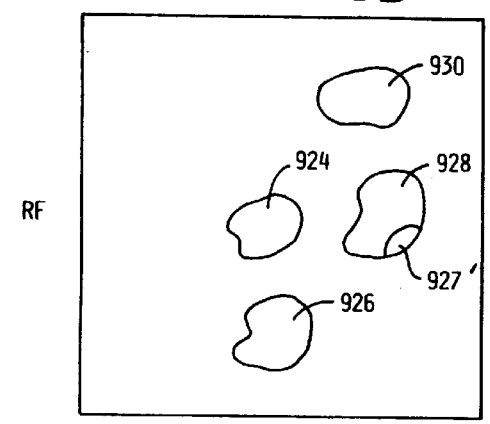

Referring to FIG. 48A, a conceptual or idealized scattergram is illustrated which shows the conventional scattergram results of the sensed characteristics of at least two groups or populations 926 and 928 of cells or formed bodies. The population 926 includes an obscured population or subset of cells 927 which is obscured or masked by the population 926 and cannot be identified separately therefrom. Microspheres having reacting agents bound thereto which are specific to or detect specific molecules on the cells of the population 927 are combined therewith, however the sensed characteristics of the 927 cells bound with or to the reacting agent microspheres will be shifted from the 926 population and be wholly or partially obscured by the population 928 forming a population 927', as illustrated in FIG. 48B. For illustration and example purposes, utilizing WBC's, a population 924 is M's, the population 926 is L's, the populations 927 and 927' are L subsets and the population 928 is G's. For example purposes, the scattergram results are shown as discrete areas, although the areas 924, 926 and 928 are actually a plurality of individual sensed data points. Also, the scattergram is depicted utilizing RF and opacity, however other parameters can be utilized such as DC or other combinations as generally shown in FIGS. 26A–D and FIGS. 57–60. In addition to the conventional sensed data groups 924, 926 and 928, a fourth artificial population 930 is illustrated, such as a population of microspheres without cells or antibodies bound thereto, which also can be utilized in the present invention.

In the present invention, the standard or control population includes sensing and counting at least the L's 926 and various combinations of the other groups to determine the white blood cell subset of interest, which in the examples are L subsets such as CD4 or CD8. The standard population is obtained, because the sensed characteristics of the L subset of interest is shifted into the G population 928 which wholly or partially obscures the L subset of interest. Generally, to obtain a correct analysis of the percentage contribution of the subset population of interest, a control population has to be obtained before and after the shift, to normalize the subset percentage.

As above described, the standard population can be:

(1) the total number of white blood cell populations 924, 926 and 928, in which case the artificial population 930 generally would not be utilized;

(2) the M population 924 which does not obscure the shifted or non-shifted sensed characteristics of the subset of interest;

(3) the artificial population 930 which also does not obscure the shifted or non-shifted sensed characteristics of the subset of interest; or (4) the G population 928 into which the sensed characteristics of the subset will be wholly or partially shifted. The standard population provides the normalization population for the methodology of the present invention.

Figure 49A:
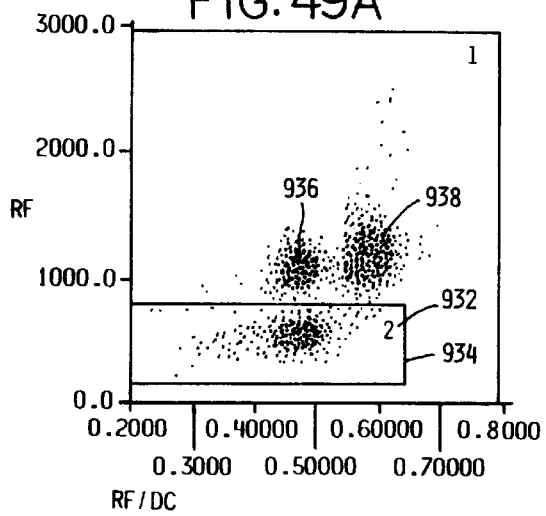
Figure 49B:
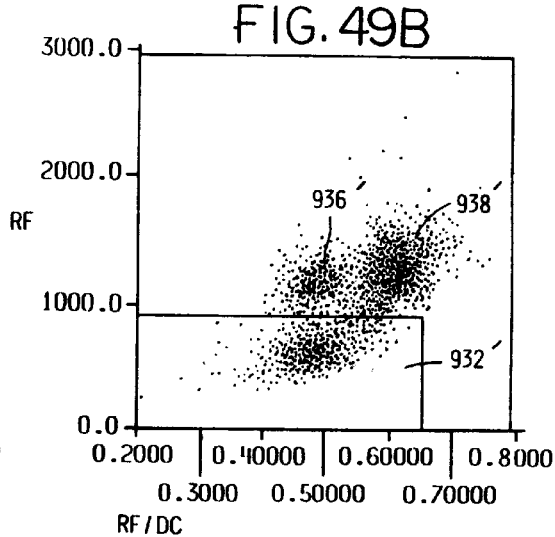

Referring now to FIGS. 49A and 49B, two sets of results depicted in scattergrams obtained from a whole blood sample utilizing a method in accordance with the instrument 900, are illustrated. Referring to FIG. 49A, a non-shifted or control scattergram is depicted. In this example, the CD8 subset of the lymphocytes is the white blood cell population subset of interest.

The control biological sample 902 is a 25 microliter sample of whole blood combined with 100 microliters of buffer. The reactant 906 is 300 microliters of RBC lyse, previously referred to, which is combined with the biological sample 902 and mixed for five seconds. The mixture is quenched with 120 microliters of quench, previously referred to, which is mixed again for five seconds and fed to the white blood cell analyzer 912. The white blood cell analyzer 912 obtains a first lymphocyte count L1 of 965, which includes the CD8 white blood cell population subset of interest. The lymphocytes are contained in a block 932, which preferably is gated at 934 to eliminate debris, such as aged neutrophils from the count. A first total white blood cell count T1 of 4862 is also obtained, which includes the cells in block 932 as well as the cells in M and G cell groups 936 and 938 outside the block 932.

The sample mixture 902 or a second portion thereof then is mixed for 15 seconds with 50 microliters of 2.2 micron microspheres in a 2 percent solution with a T8 specific monoclonal antibody bound thereto. If a second portion of the mixture 902 is utilized, the RBC's would be eliminated by one of the above referenced methods. The shifted mixture then is fed to the white blood cell analyzer 912 to obtain the scattergram depicted in FIG. 49B. The CD8 white blood cell population subset now has been shifted from the lymphocyte cells in the block 932' into the G group of cells 938'.

The CD8 white blood cell population subset was obscured or partially obscured by the L's in block 932 and now are obscured or partially obscured by the G cells in the cell group 938'. The white blood cell analyzer 912 obtains a second count L2 of L's of 764 (reduced from 965) and a second total white blood cell count T2 of 4864.

If the total white blood cell counts were identical, then the CD8 count could be obtained merely by subtraction. However, if this is not the situation, and generally it would not be, then the percentage can be normalized, for example, by utilizing the two total white blood cell counts as follows:

$$\frac{L1}{T1} = \frac{X}{T2} \text{ so } X = \frac{(L1)(T2)}{T1} = \frac{(965)(4864)}{4862} = 965.4$$

$$CD8 \text{ percentage} = \frac{(X - 764)100}{X} = \frac{(965.4 - 764)100}{965.4} = 20.86$$

The CD8 percentage obtained was compared to the percentage obtained by flow cytometry, which was 23.0%. Other control populations can be utilized as previously described.

Figure 50A:
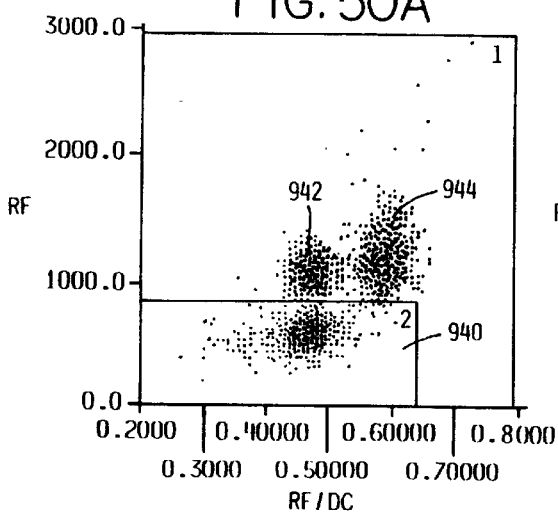
Figure 50B:
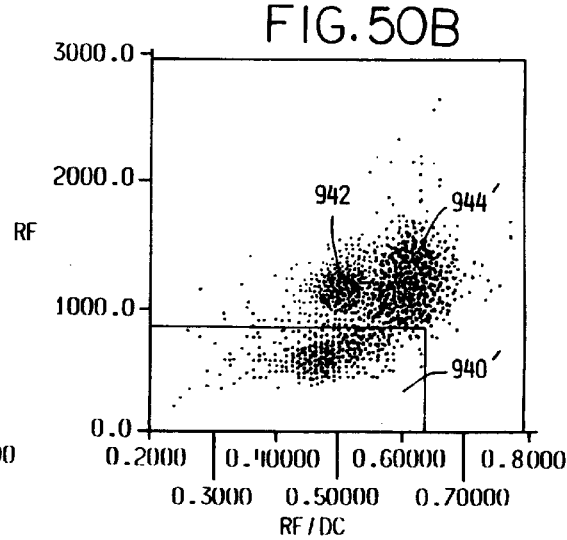

The CD4 white blood cell population subset percentage can be obtained in a similar manner as illustrated in FIGS. 50A and 50B. In this example the microspheres are bound to T4 specific monoclonal antibodies and are mixed for 30 seconds. The control scattergram is depicted in FIG. 50A. Again, a first lymphocyte count 1171 of the L's in a block 940 is obtained and a first total white blood cell count of 4863 is obtained, including the groups of M and G cells 942 and 944.

The shifted scattergram is depicted in FIG. 50B, which provides a second L count of 878 and a second white blood cell total count of 4857. The total CD4 white blood cell subset population is 24.9 percent, which compares to a flow cytometry count of 28.6 percent.

In the above examples, the scattergrams were obtained by utilizing RF and opacity. Other sensing parameters also can be utilized, see for example FIGS. 57–60, the RF parameter however provides a good demarcation between the L's and the remaining white blood cells. Also, all the white blood cells are counted in the examples, but the M's in group 936 and 942 can be ignored, since the M's do not obscure either the shifted or unshifted CD4 or CD8 white blood cell population subset of interest.

Figure 51A:
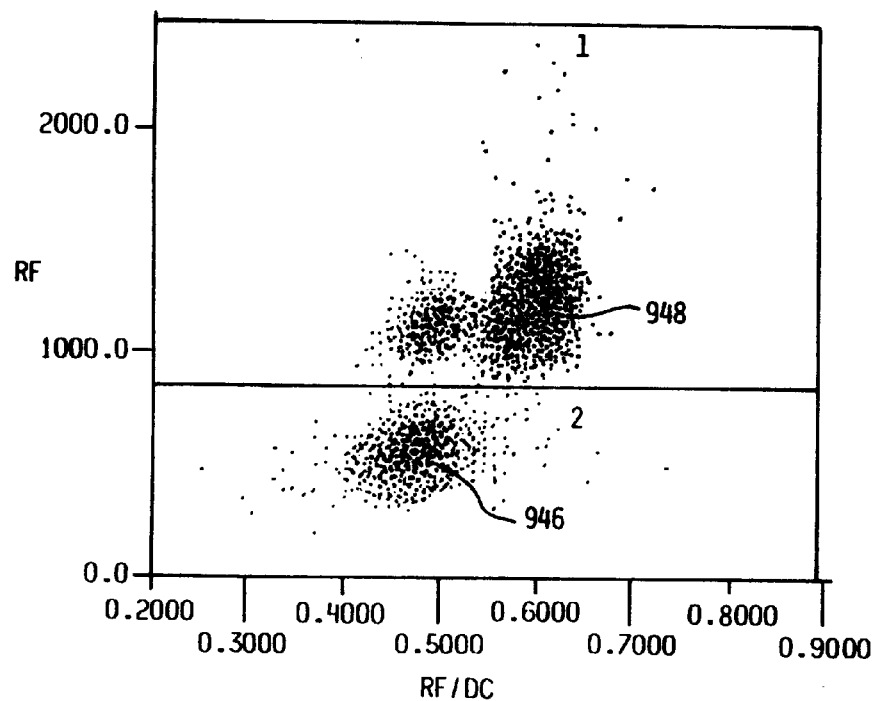
Figure 51B:
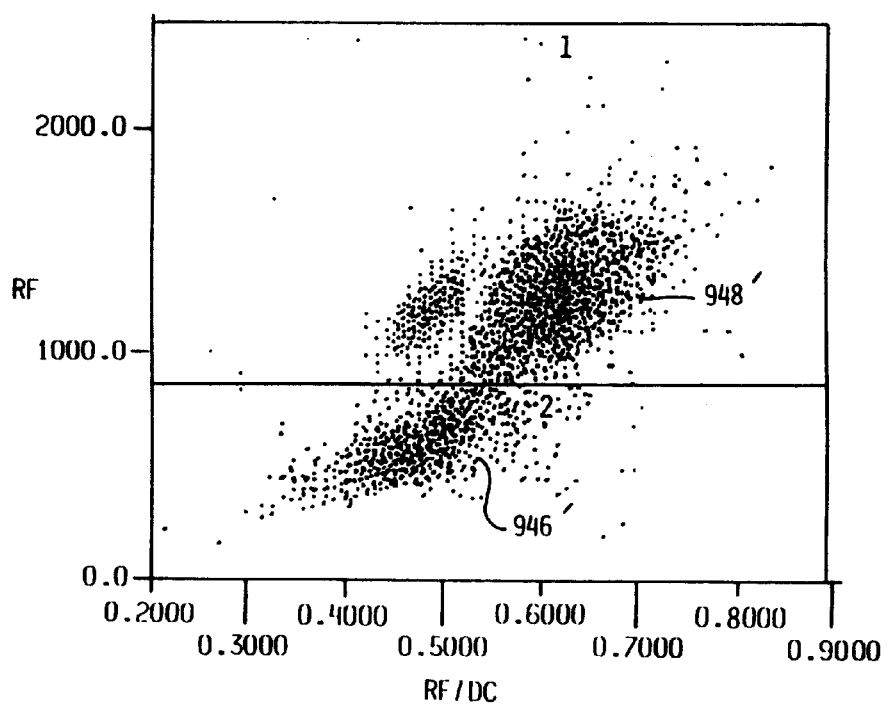

Three additional examples of CD8 percentages from different samples are depicted in FIGS. 51–53. In FIG. 51A, a first L count of 1520 was obtained in a block 946, while a first total white blood cell count of 4861 was obtained counting the L's in the block 946 and the remaining cells and cell groups in a block 948. The second shifted L count of 1030 was obtained in a block 946' of FIG. 51B, while the second total white blood cell count of 4856 was obtained including the cells in blocks 946' and 948'. The CD8 percentage obtained was 32.2 while flow cytometry provided a percentage of 34.6.

Figure 52A:
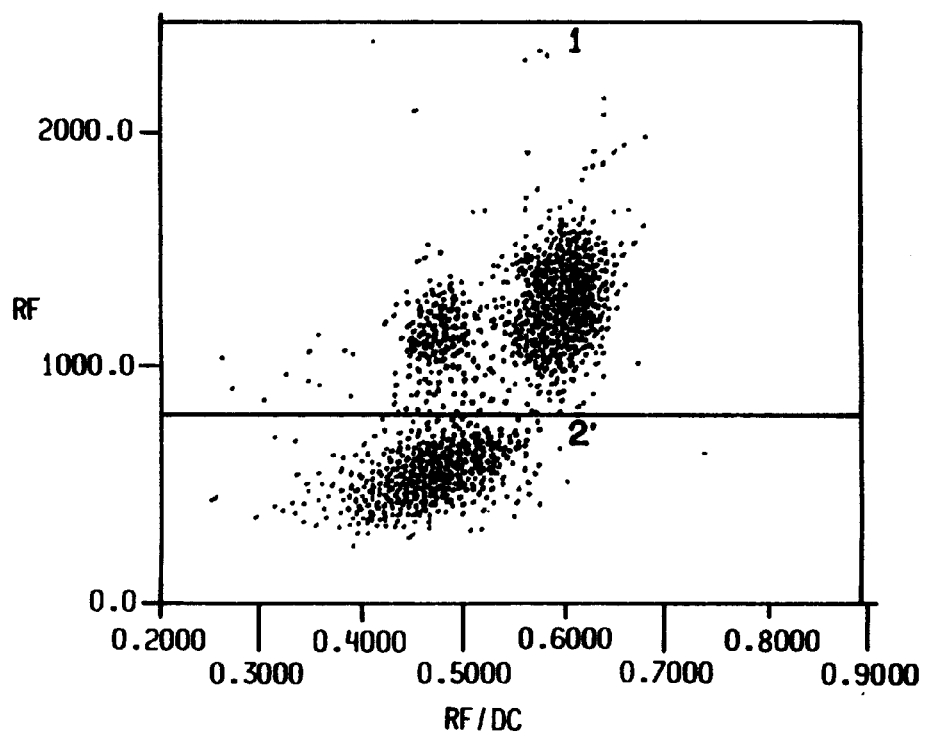
Figure 52B:
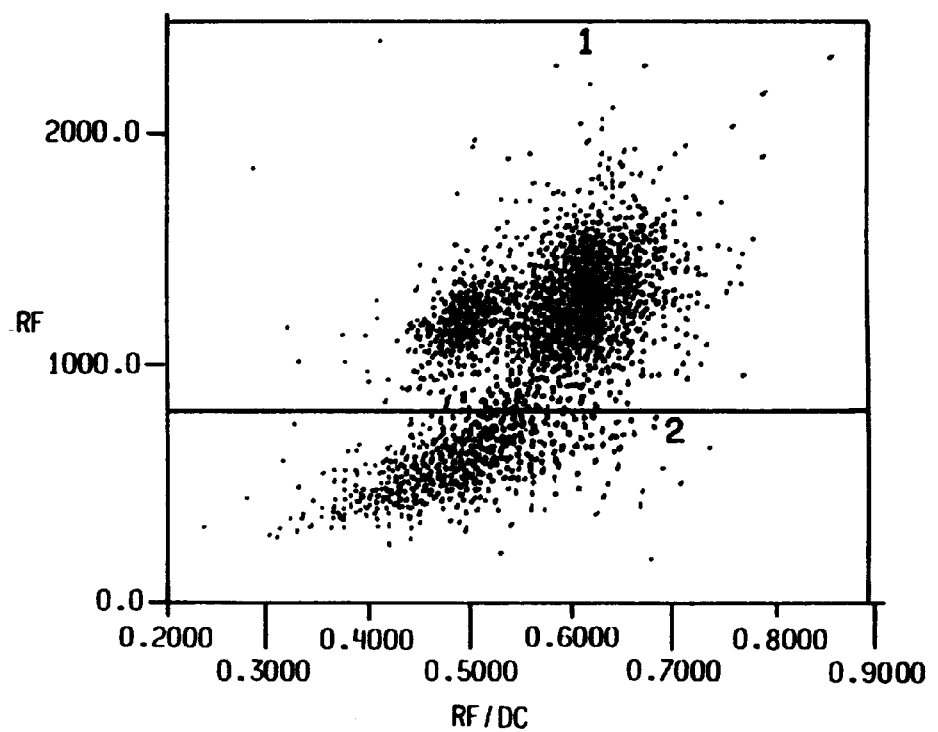
Figure 53A:
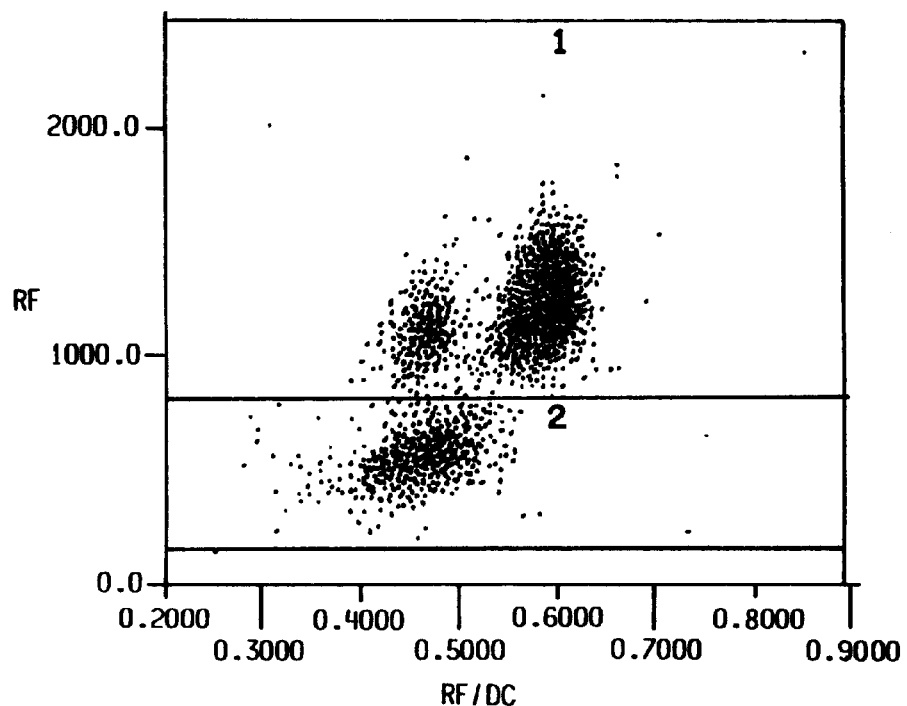
Figure 53B:
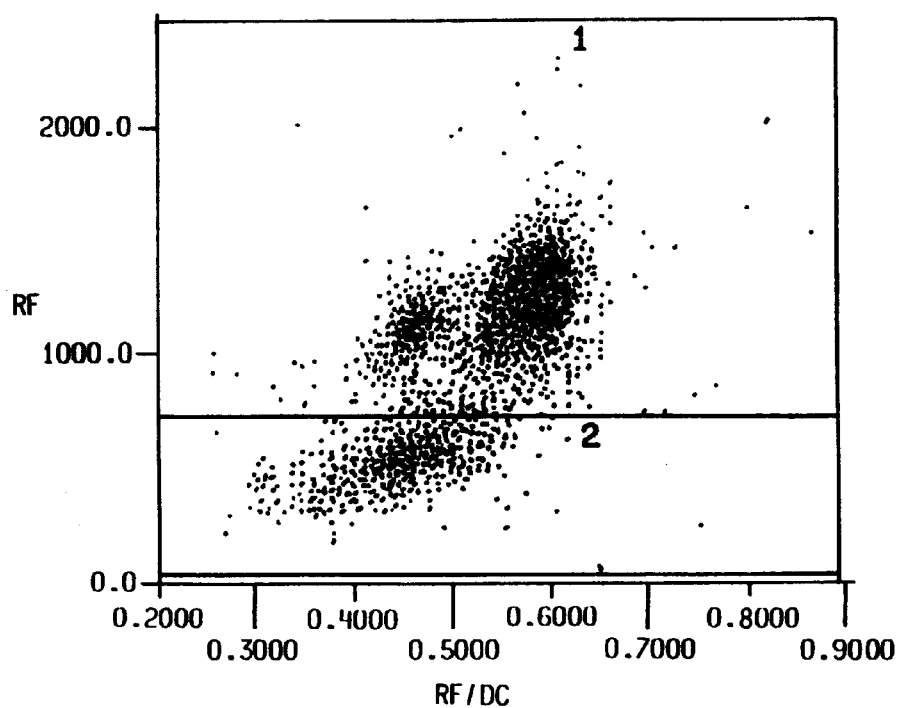

In the same manner, the scattergrams of FIGS. 52A and 52B provided first and second L counts of 1393 and 930 and first and second white blood cell counts of 9864 and 4861. The CD8 percentage obtained was 33.2, which compared to the flow cytometry percentage of 31.3. The scattergrams of FIGS. 53A and 53B provided first and second L counts of 1031 and 778 and first and second white blood cell counts of 4862 and 4860. The CD8 percentage obtained was 24.5, which compared to the flow cytometry percentage of 21.7.

Figure 54A:
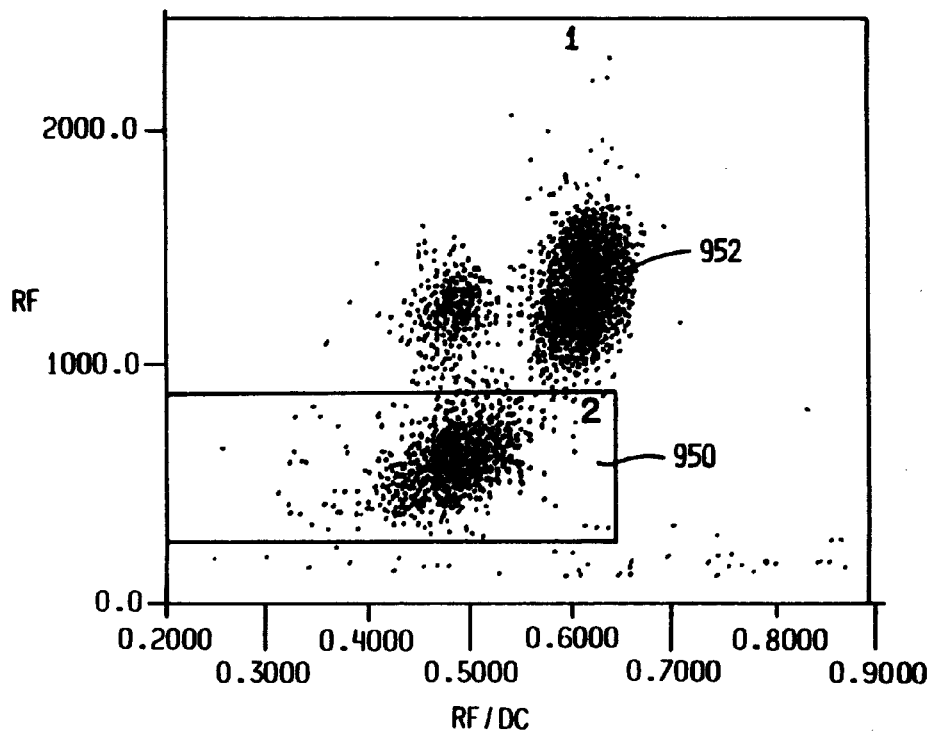
Figure 54B:
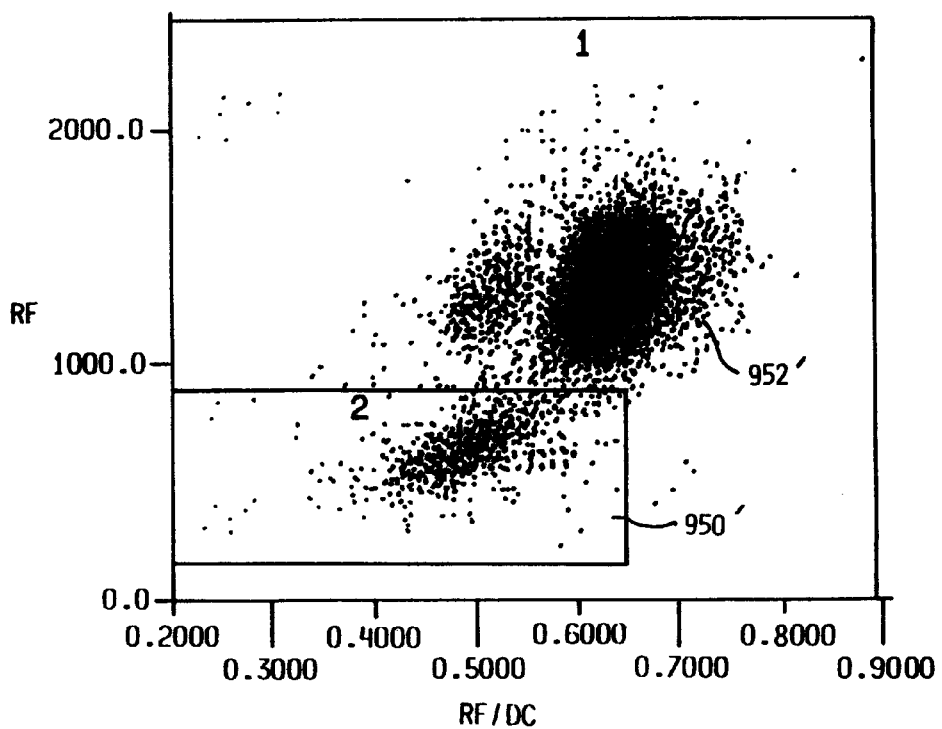

Three additional examples of the CD4 percentage obtained from different samples are depicted in FIGS. 54–56. In FIG. 54A, a first L count of 1372 was obtained in a block 950, while a first total white blood cell count of 4764 was obtained counting the L's in the block 950 and the remaining cells and cell groups in a block 952. The second shifted L count of 670 was obtained in the block 950' in FIG. 54B, while the second total white blood cell count of 4855 was obtained including the cells in blocks 950' and 952'. The CD4 percentage obtained was 52.1, while the flow cytometry provided a percentage of 54.4.

Figure 55A:
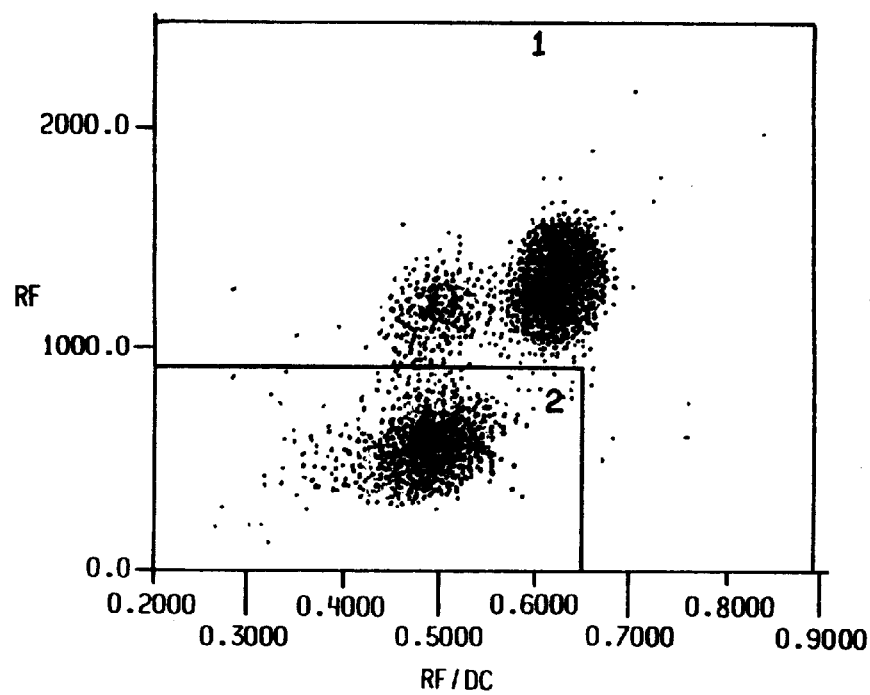
Figure 55B:
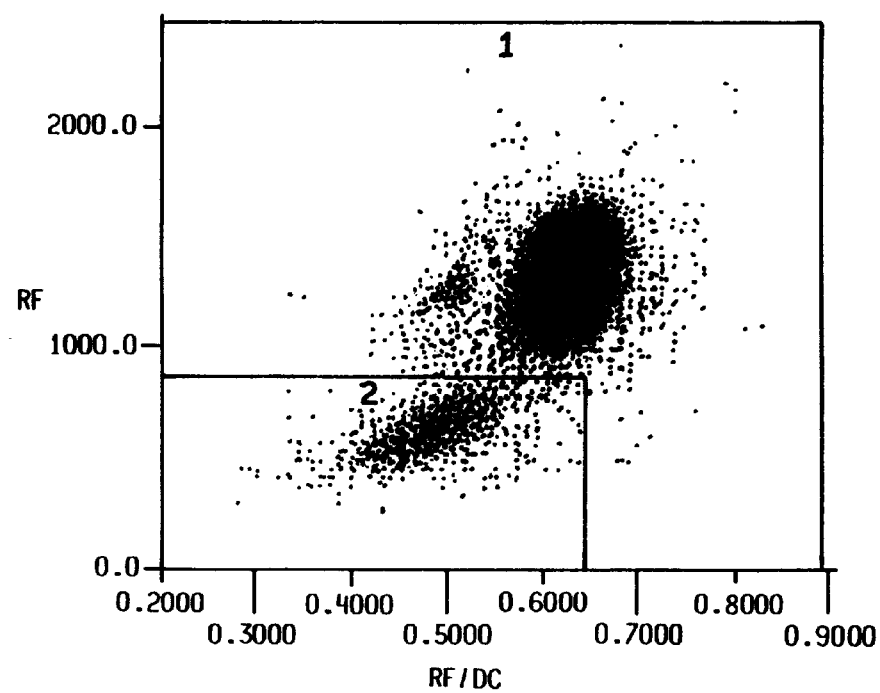
Figure 56A:
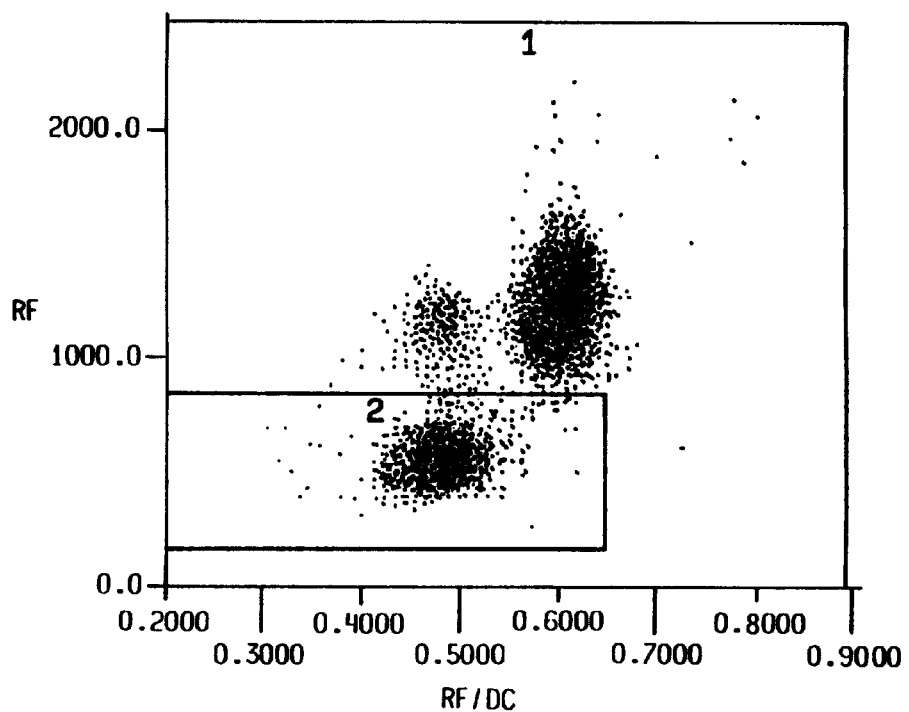
Figure 56B:
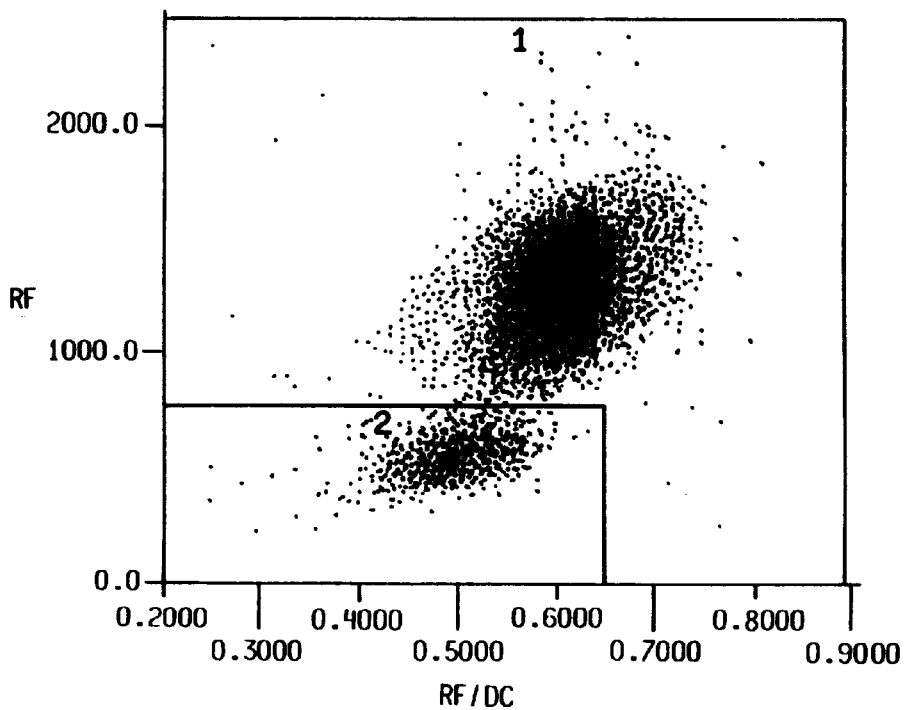
Figure 57A:
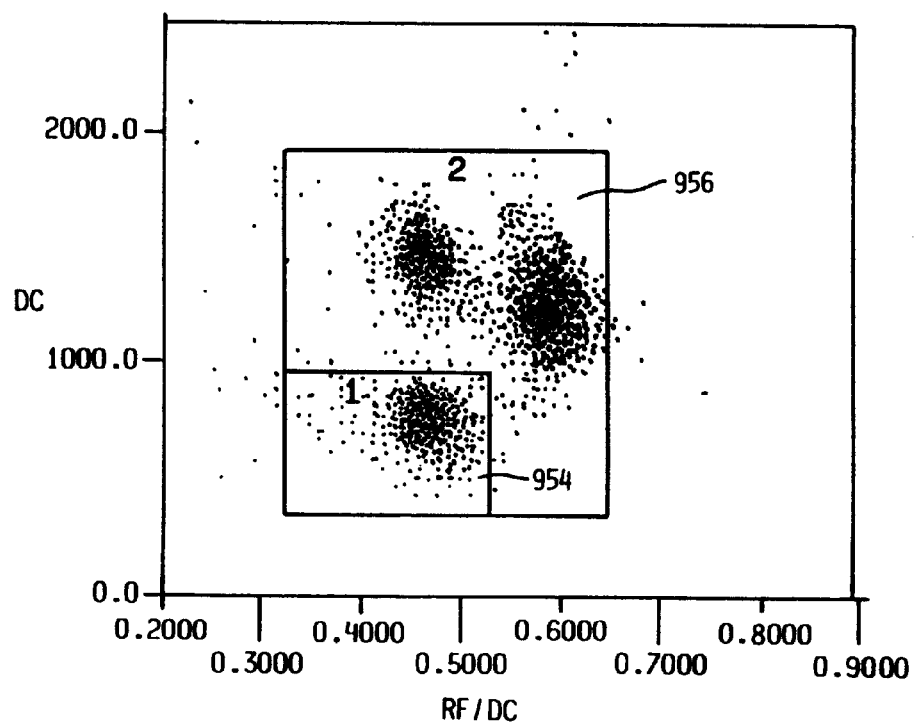
Figure 57B:
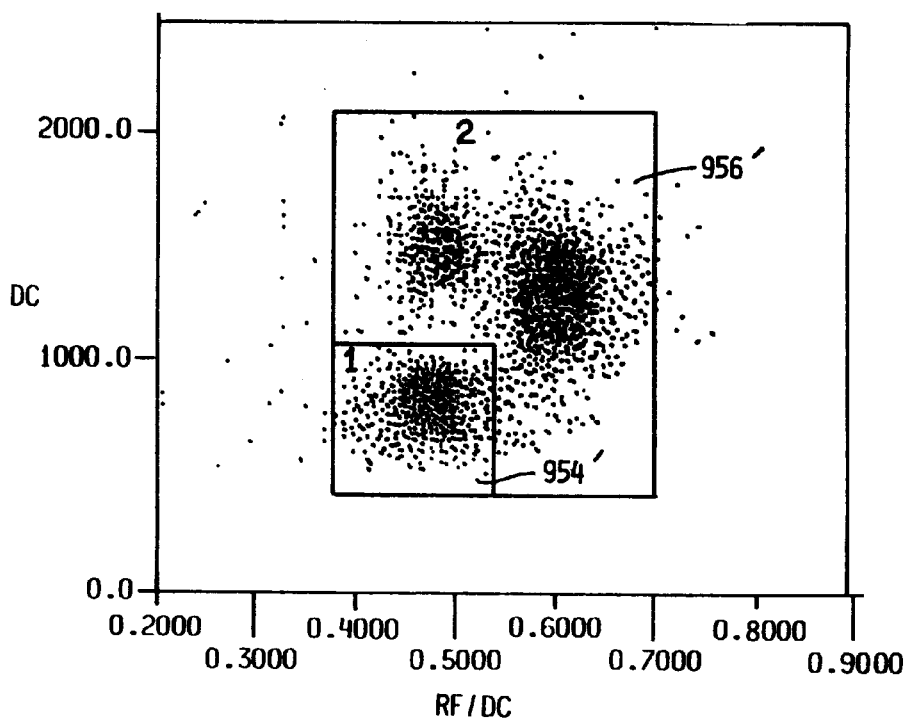

In the same manner, the scattergrams of FIGS. 55A and 55B, provided first and second L counts of 1684 and 956 and first and second white blood cell counts of 4863 and 4862. The CD4 percentage obtained was 43.2, which compared to the flow cytometry percentage of 45.3. The scattergrams of FIGS. 56A and 56B provided first and second L counts of 1234 and 542 and first and second white blood cell counts of 4859 and 4857. The CD4 percentage obtained was 56.1, which compared to the flow cytometry percentage of 56.3.

FIGS. 57–60 illustrate other combinations of electronic sensing parameters to form the scattergrams. In FIGS. 57A and B, the scattergram utilizes DC and opacity for the illustration. A first L count of 868 was obtained in a block 954, while a first total white blood cell count of 4827 was obtained counting the L's in the block 954 and the remaining cells and cell groups in a block 956. The second shifted L count of 664 was obtained in a block 954' of FIG. 57B, while the second total white blood cell count of 4813 was obtained including the cells in blocks 954' and 956'. The CD8 percentage obtained was 23.2.

Figure 58A:
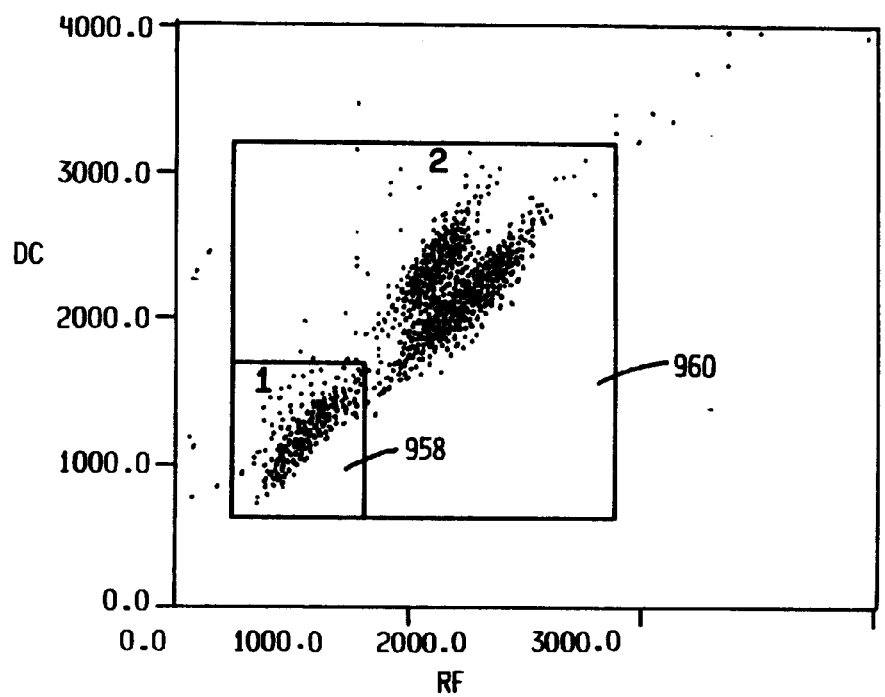
Figure 58B:
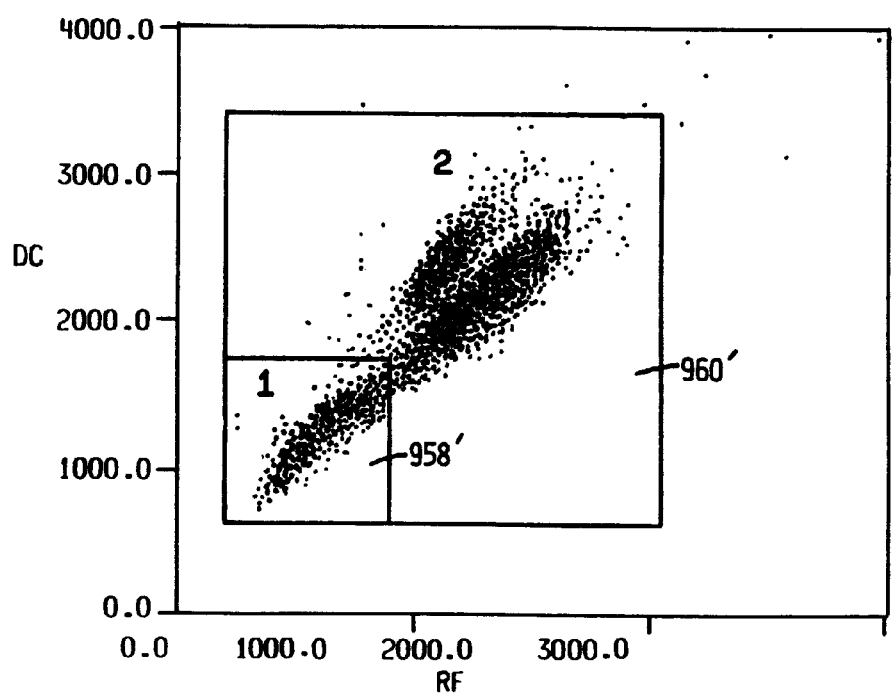

The scattergrams of FIGS. 58A and 58B are illustrated utilizing DC and RF as the sensing parameters. In FIG. 58A, a first L count of 926 was obtained in a block 958, while a first total white blood cell count of 4848 was obtained counting the L's in the block 958 and the remaining cells and cell groups in a block 960. The second shifted L count of 776 was obtained in a block 958' of FIG. 58B, while the second total white blood cell count of 4855 was obtained including the cells in blocks 958' and 960'. The CD8 percentage obtained was 16.3.

Figure 59A:
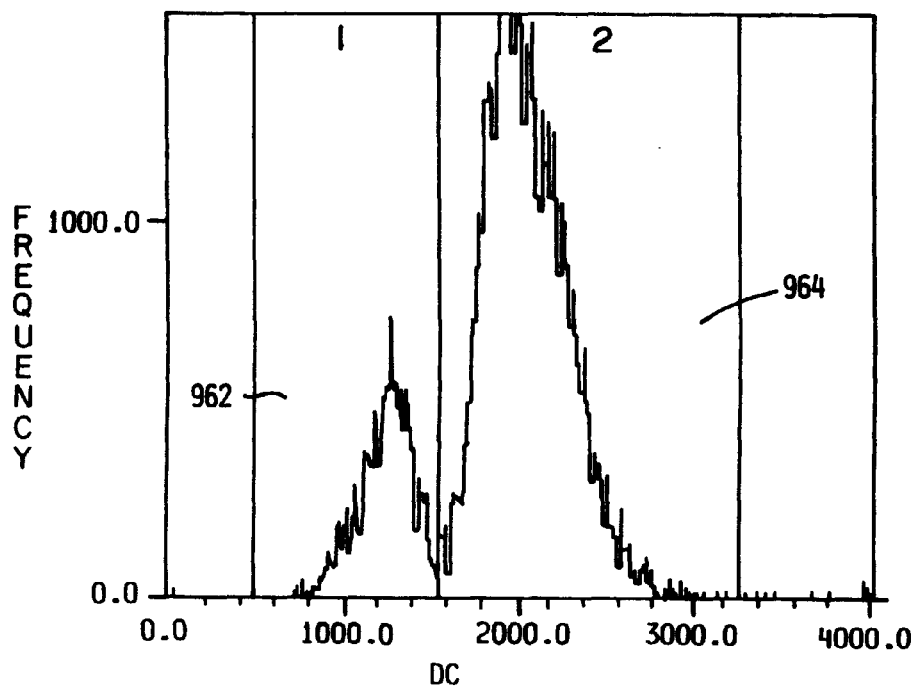
Figure 59B:
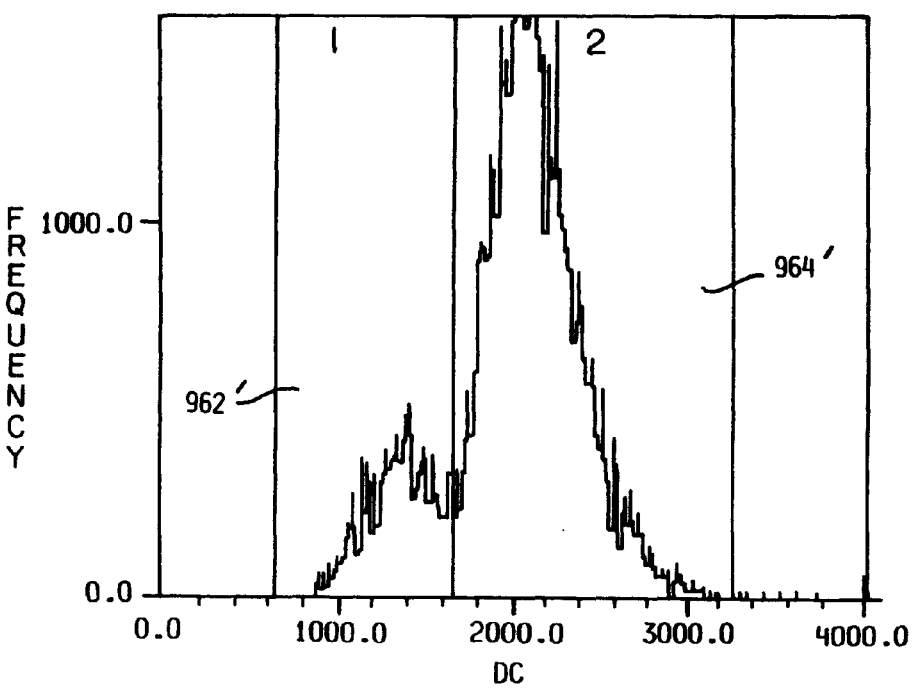

The scattergrams of FIGS. 59A and 59B are illustrated utilizing only a single, DC, sensing parameter. In FIG. 59A a first L count of 935 was obtained in a block 962, while a first total white blood cell count of 3918 was obtained counting the L's in the block 962 and the remaining cells and cell groups in a block 964. The second shifted L count of 825 was obtained in a block 962' of FIG. 59B, while the second total white blood cell count of 4029 was obtained including the cells in blocks 962' and 964'. The CD8 percentage obtained was 11.8.

Figure 60A:
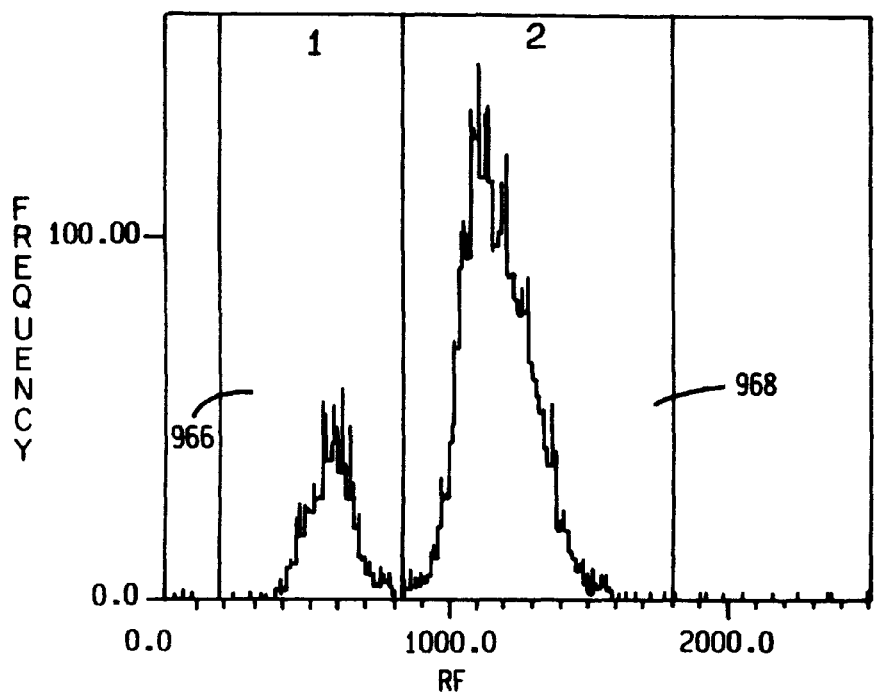
Figure 60B:
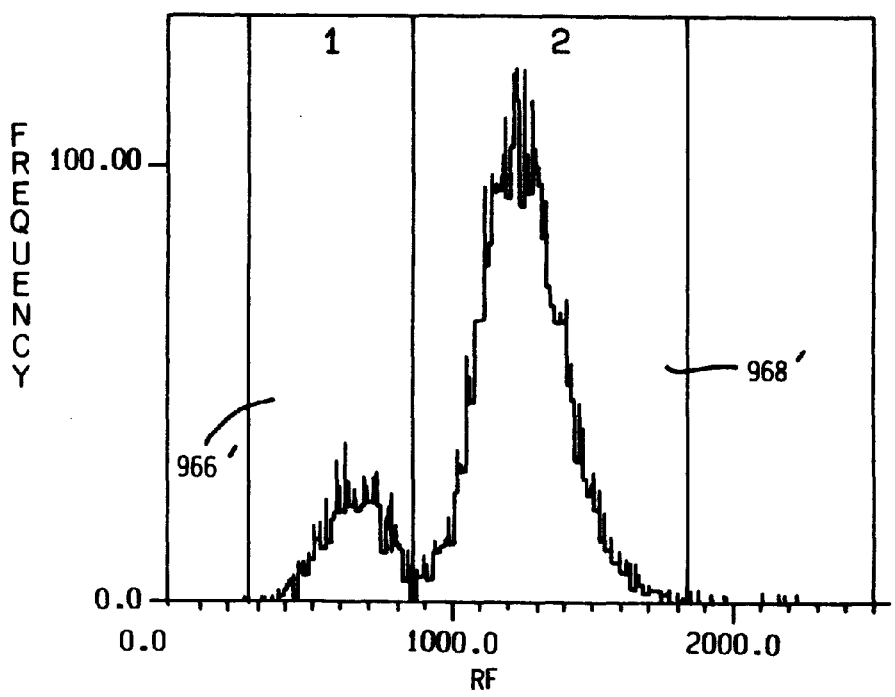

The scattergram of FIGS. 60A and 60B are illustrated utilizing only a single, RF, sensing parameter. In FIG. 60A a first L count of 969 was obtained in a block 966, while a first total white blood cell count of 3880 was obtained counting the L's in the block 966 and the remaining cells and cell groups in a block 968. The second shifted L count of 779 was obtained in a block 966' of FIG. 60B, while the second total white blood cell count of 4069 was obtained including the cells in blocks 966' and 968'. The CD8 percentage obtained was 19.6.

The scattergrams of FIGS. 57–60 are not optimized and the data as depicted is not clearly separated. This can be seen especially from the one-dimensional sensing of FIGS. 59A and B and FIGS. 60A and B since each of the Figures are derived from the same data. This is especially pronounced in FIGS. 60A and B, since a result was obtained of 11.8, which is far from the result of 23.2 obtained in FIGS. 57A and B. Also, although 2.2 diameter micron microspheres were utilized for example purposes, other sizes also can be utilized.

In the above described examples, the standard population utilized is the total count of the total white blood cell populations, since the total count should remain constant. The standard population also can be the non-interfering white blood count 924 or artificial population 930 (FIG. 48), which is unaffected or non-obscured by the white blood population subset of interest, before or after it is shifted. Since the white blood cell population is unaffected, the first and second counts thereof should be the same except for cell fragments, errant microspheres or other aberrations. The artificial population can be formed by a set of microspheres, which also are unobscured.

Also, although the method and the apparatus of the present invention have been described utilizing whole blood samples, there can be instances where it is desired to utilize a portion of a sample with the RBC's and/or some of the WBC populations removed. Clearly, the RBC's are still removed, but arguably externally and not within the apparatus of the present invention. Such removal or preprepration can be carried out in numerous conventional ways, such as utilizing a lysing reagent, density or centrifugation techniques, such as ficoll, dextran, "buffycoat", etc. In an automated analyzer utilizing the present invention, it would be preferable to utilize a whole blood sample for speed and integrity in the analysis of the sample.

Many modifications and variations of the present invention are possible in light of the above teachings. The samples 12, 42, 150, 180, 294, 322, 342 and 902 can include whole blood, human body fluids containing cells, or other fluids containing formed bodies, such as bacteria, viruses and fungi. The volumes of microspheres specified are stated in weight of microspheres per volume of diluent. Although volumes on the order of about 20 microliters of sample, such as a whole blood sample, have been utilized for example purposes herein, smaller or larger sample volumes also can be utilized as desired. For example, as small as about 2 microliters of a sample up to whatever volume of sample is practical for the particular instrument or technique can be utilized. Although some of the examples were performed in sequential steps, the steps can also be performed simultaneously. A simultaneous analysis allows the least complex instrument module to be utilized. It is therefore, to be understood that within the scope of the appended claims, the invention may be practiced otherwise than as specifically described.

What is claimed and desired to be secured by Letters Patent of the United States is:

1. A method of obtaining at least one obscured or partially obscured population analysis from at least a portion of a sample having at least a first cell population including at least one population subset of interest and a second cell population, comprising:
   electronically sensing and counting a first population including at least the first cell population and subsets thereof to form a first count;
   shifting the cell population subset of interest out of said first cell population and at least partially into a second cell population by binding microspheres having a reactant bonded thereto specific to said cell population subset of interest to said cell population subset;
   electronically sensing and counting the remaining first population including at least the first cell population without the shifted subset and with remaining subsets thereof to form a second count; and
   comparing said first and second counts to obtain the percentage contribution of the cell population subset of interest.

2. The method as defined in claim 1 including electronically sensing and counting said populations utilizing two different electronic parameters.

3. The method as defined in claim 1 including electronically sensing and counting said populations utilizing a single electronic parameter.

4. The method as defined in claim 1 including shifting said cell population subset of interest by mixing said microspheres with said sample to bind to said cell population subset of interest and shift at least one sensed characteristic of said cell population subset of interest.

5. The method as defined in claim 4 including providing monoclonal antibodies forming said reactants with antigens on said cell population subset of interest forming said specific molecule.

6. The method as defined in claim 1 including providing a whole blood sample having at least a first white blood cell population forming said first cell population and a second white blood cell population forming said second cell population.

7. The method as defined in claim 6 including said first white blood cell population including a CD4 white blood cell Dopulation subset and shifting the CD4 white blood cell population subset by providing microspheres having a monoclonal antibody bonded thereto which is specific to said CD4 white blood cell population subset and mixing said microspheres with said sample to bind to said CD4 subset population to shift at least one sensed characteristic of said CD4 subset population.

8. The method as defined in claim 6 including said first white blood cell population including a CD8 white blood cell population subset and shifting the CD8 white blood cell population subset by providing microspheres having a monoclonal antibody bonded thereto which is specific to said CD8 white blood cell population subset and mixing said microspheres with said sample to bind to said CD8 subset population to shift at least one sensed characteristic of said CD8 subset population.

9. The method as defined in claim 6 wherein said whole blood sample includes a red blood cell population and including removing said red blood cell population from said sample without significantly adversely affecting relevant qualities and/or quantities of said white blood cell populations.

10. The method as defined in claim 6 including sensing and counting at least the first white blood cell population and subsets thereof and the second white blood cell population to form a third count prior to said shifting of the white blood cell population subset of interest and sensing and counting at least the remaining first white blood cell population and subsets thereof and the second white blood cell population including said shifted white blood cell subset of interest to form a fourth count following said shifting of the white blood cell population subset of interest and comparing said first and second counts to at least one of said third and fourth counts to obtain the percentage contribution of the white blood cell population subset of interest, said microspheres being of a smaller size than said cells sufficient to shift cells to an area on a scattergram where they can be separately identified and counted from the other cells which have not been shifted.

11. The method as defined in claim 10 including comparing said first and second counts to both of said third and fourth counts to normalize the percentage contribution.

12. The method as defined in claim 10 including sensing and counting all of the white blood cell populations and subsets thereof to form said third and fourth counts.

13. The method as defined in claim 6 including sensing and counting a standard population to form a third count prior to said shifting of the white blood cell population subset of interest and sensing and counting said standard population following said shifting of the white blood cell population subset of interest to form a fourth count and comparing said third and fourth counts to normalize the percentage contribution.

14. The method as defined in claim 13 wherein said standard population is an artificial population formed by non-interfering microspheres.

15. The method as defined in claim 13 where said standard population is a non-interfering white blood cell population.

16. The method as defined in claim 13 wherein said microspheres are of a smaller size than said cells sufficient to shift cells to an area on a scattergram where they can be separately identified and counted from the other cells which have not been shifted, and said standard population is a total of all the white blood cell populations.

17. An apparatus for obtaining at least one obscured or partially obscured population analysis from at least a portion of a sample having at least a first cell population including at least one population subset of interest and a second cell population comprising:

means for electronically sensing and counting a first population including at least the first cell population and subsets thereof to form a first count;

means for shifting the cell population subset of interest out of said first cell population and at least partially into a second cell population by binding microspheres having a reactant bonded thereto specific to said cell population subset of interest to said cell population subset;

means for electronically sensing and counting the remaining first population including at least the first cell population without the shifted subset and with remaining subsets thereof to form a second count; and means for comparing said first and second counts to obtain the percentage contribution of the cell population subset of interest.

18. The apparatus as defined in claim 17 including means for electronically sensing and counting said populations utilizing two different electronic parameters.

19. The apparatus as defined in claim 17 including means for electronically sensing and counting said populations utilizing a single electronic parameter.

20. The apparatus as defined in claim 17 including means for shifting said cell population subset of interest by mixing said microspheres with said sample to bind to said cell population subset of interest and shift at least one sensed characteristic of said cell population subset of interest.

21. The apparatus as defined in claim 20 including means for providing monoclonal antibodies forming said reactants with antigens on said cell population subset of interest forming said specific molecule.

22. The apparatus as defined in claim 17 including a whole blood sample having at least a first white blood cell population forming said first cell population and a second white blood cell population forming said second cell population.

23. The apparatus as defined in claim 22 including said first white blood cell population including a CD4 white blood cell population subset and means for shifting the CD4 white blood cell population subset including means for providing microspheres having a monoclonal antibody bonded thereto which is specific to said CD4 white blood cell population subset and means for mixing said microspheres with said sample to bind to said CD4 subset population to shift at least one sensed characteristic of said CD4 subset population.

24. The apparatus as defined in claim 22 said first white blood cell population including a CD8 white blood cell population subset and including means for shifting the CD8 white blood cell population subset including means for providing microspheres having a monoclonal antibody bonded thereto which is specific to said CD8 white blood cell population subset and means for mixing said microspheres with said sample to bind to said CD8 subset population to shift at least one sensed characteristic of said CD8 subset population.

25. The apparatus as defined in claim 22 wherein said whole blood sample includes a red blood cell population and including means for removing said red blood cell population from said sample without significantly adversely affecting relevant qualities and/or quantities of said white blood cell populations.

26. The apparatus as defined in claim 22 including means for sensing and counting at least the first white blood cell population and subsets thereof and the second white blood cell population to form a third count prior to said shifting of the white blood cell population subset of interest and means for sensing and counting at least the remaining first white blood cell population and subsets thereof and the second white blood cell population including said shifted white blood cell subset of interest to form a fourth count following said shifting of the white blood cell population subset of interest and means for comparing said first and second counts to at least one of said third and fourth counts to obtain the percentage contribution of the white blood cell population subset of interest, said microspheres being of a smaller size than said cells sufficient to shift cells to an area on a scattergram where they can be separately identified and counted from the other cells which have not been shifted.

27. The apparatus as defined in claim 26 including means for comparing said first and second counts to both of said third and fourth counts to normalize the percentage contribution.

28. The apparatus as defined in claim 26 including means for sensing and counting all of the white blood cell populations and subsets thereof to form said third and fourth counts.

29. The apparatus as defined in claim 22 including means for sensing and counting a standard population to form a third count prior to said shifting of the white blood cell population subset of interest and means for sensing and counting said standard population following said shifting of the white blood cell population subset of interest to form a fourth count and means for comparing said third and fourth counts to normalize the percentage contribution.

30. The apparatus as defined in claim 29 wherein said standard population is an artificial population formed by non-interfering microspheres.

31. The apparatus as defined in claim 29 where said standard population is a non-interfering white blood cell population.

32. The apparatus as defined in claim 29 wherein said microspheres are of a smaller size than said cells sufficient to shift cells to an area on a scattergram where they can be separately identified and counted from the other cells which have not been shifted, and said standard population is a total of all the white blood cell populations.

\* \* \* \* \*